United States Patent
Steiniger et al.

(12)

(10) Patent No.: US 12,049,509 B2
(45) Date of Patent: *Jul. 30, 2024

(54) NUCLEIC ACIDS ENCODING A CANINE ANTIBODY WHICH BINDS NERVE GROWTH FACTOR AND VECTORS AND HOST CELLS THEREOF

(71) Applicant: Zoetis Services LLC, Parsippany, NJ (US)

(72) Inventors: Sebastian C. J. Steiniger, Kalamazoo, MI (US); William Dunkle, Kalamazoo, MI (US); Catherine Rugg, Cronulla (AU); Steven A. Dunham, Kalamazoo, MI (US)

(73) Assignee: Zoetis Services LLC, Parsippany, NJ (US)

(*) Notice: Subject to any disclaimer, the term of this patent is extended or adjusted under 35 U.S.C. 154(b) by 411 days.

This patent is subject to a terminal disclaimer.

(21) Appl. No.: 17/196,135

(22) Filed: Mar. 9, 2021

(65) Prior Publication Data

US 2021/0188988 A1 Jun. 24, 2021

Related U.S. Application Data

(63) Continuation of application No. 16/251,293, filed on Jan. 18, 2019, now Pat. No. 10,982,002.

(60) Provisional application No. 62/641,538, filed on Mar. 12, 2018.

(51) Int. Cl.
| | | |
|---|---|---|
| *C12N 15/13* | (2006.01) | |
| *A61K 31/713* | (2006.01) | |
| *A61K 39/395* | (2006.01) | |
| *A61P 3/04* | (2006.01) | |
| *A61P 3/10* | (2006.01) | |
| *A61P 9/10* | (2006.01) | |
| *A61P 29/02* | (2006.01) | |
| *C07K 16/22* | (2006.01) | |
| *C07K 16/28* | (2006.01) | |
| *C12N 15/11* | (2006.01) | |
| *C12N 15/63* | (2006.01) | |
| *A61K 38/00* | (2006.01) | |
| *A61K 39/00* | (2006.01) | |

(52) U.S. Cl.
CPC ........ *C07K 16/2875* (2013.01); *A61K 31/713* (2013.01); *A61K 39/39533* (2013.01); *A61P 3/04* (2018.01); *A61P 3/10* (2018.01); *A61P 9/10* (2018.01); *A61P 29/02* (2018.01); *C07K 16/22* (2013.01); *C12N 15/11* (2013.01); *C12N 15/63* (2013.01); *A61K 38/00* (2013.01); *A61K 2039/505* (2013.01); *C07K 2317/21* (2013.01); *C07K 2317/24* (2013.01); *C07K 2317/30* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,230,691 A | 10/1980 | Young |
| 4,526,938 A | 7/1985 | Churchill et al. |
| 4,554,101 A | 11/1985 | Hopp |
| 4,676,980 A | 6/1987 | Segal et al. |
| 4,816,567 A | 3/1989 | Cabilly et al. |
| 4,946,778 A | 8/1990 | Ladner et al. |
| 4,980,286 A | 12/1990 | Morgan et al. |
| 5,128,326 A | 7/1992 | Balasz et al. |
| 5,130,311 A | 7/1992 | Guillaumet et al. |
| 5,147,294 A | 9/1992 | Smith et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,342,942 A | 8/1994 | Jaen et al. |
| 5,350,576 A | 9/1994 | Payne et al. |
| 5,403,484 A | 4/1995 | Ladner et al. |
| 5,409,944 A | 4/1995 | Black et al. |
| 5,427,908 A | 6/1995 | Dower et al. |
| 5,436,265 A | 7/1995 | Black et al. |
| 5,500,362 A | 3/1996 | Robinson et al. |
| 5,510,368 A | 4/1996 | Lau et al. |
| 5,516,637 A | 5/1996 | Huang et al. |
| 5,530,101 A | 6/1996 | Queen et al. |
| 5,536,752 A | 7/1996 | Ducharme et al. |
| 5,545,806 A | 8/1996 | Lonberg et al. |
| 5,545,807 A | 8/1996 | Surani et al. |

(Continued)

FOREIGN PATENT DOCUMENTS

| | | |
|---|---|---|
| WO | WO 1989/09225 A1 | 10/1989 |
| WO | WO 1990/02809 A1 | 3/1990 |

(Continued)

OTHER PUBLICATIONS

Edwards et al. (J. Mol. Biol. 334: 103-118, 2003).*
Torres et al. (Trends in Immunol. 29(2): 91-97, 2008).*
Khan et al. (J. Immunol. 192: 5398-5405, 2014).*
Poosarla et al. (Biotech. Bioengineer. 124(6): 1331-1342, 2017).*
Paul, Fundamental Immunology, 3rd Edition, 1993, pp. 292-295, under the heading "Fv Structure and Diversity in Three Dimensions").*

(Continued)

*Primary Examiner* — Christine J Saoud
(74) *Attorney, Agent, or Firm* — Kelly M. Sullivan

(57) ABSTRACT

The present disclosure encompasses novel anti-NGF antibodies, antigen binding proteins and polynucleotides encoding the same. The disclosure further provides use of the novel antibodies, antigen binding proteins and/or nucleotide of the invention for the treatment of NGF related disorders, particularly in for the management of pain.

5 Claims, 16 Drawing Sheets

Specification includes a Sequence Listing.

(56) References Cited

U.S. PATENT DOCUMENTS

| | | |
|---|---|---|
| 5,550,142 A | 8/1996 | Ducharme et al. |
| 5,552,422 A | 9/1996 | Gauthier et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,639,780 A | 6/1997 | Lau et al. |
| 5,648,260 A | 7/1997 | Winter et al. |
| 5,656,435 A | 8/1997 | Nakahama et al. |
| 5,658,727 A | 8/1997 | Barbas et al. |
| 5,679,377 A | 10/1997 | Bernstein et al. |
| 5,693,761 A | 12/1997 | Queen et al. |
| 5,693,762 A | 12/1997 | Queen et al. |
| 5,698,426 A | 12/1997 | Huse |
| 5,712,100 A | 1/1998 | Nakahama et al. |
| 5,714,352 A | 2/1998 | Jakobovits |
| 5,723,323 A | 3/1998 | Kauffman et al. |
| 5,733,743 A | 3/1998 | Johnson et al. |
| 5,750,373 A | 5/1998 | Garrard et al. |
| 5,763,192 A | 6/1998 | Kauffman et al. |
| 5,766,886 A | 6/1998 | Studnicka et al. |
| 5,780,225 A | 7/1998 | Wigler et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,821,337 A | 10/1998 | Carter et al. |
| 5,824,514 A | 10/1998 | Kauffman et al. |
| 5,843,942 A | 12/1998 | Breault et al. |
| 5,844,092 A | 12/1998 | Presta et al. |
| 5,852,183 A | 12/1998 | Maeda |
| 5,855,913 A | 1/1999 | Hanes |
| 5,866,692 A | 2/1999 | Shitara et al. |
| 5,874,064 A | 2/1999 | Edwards et al. |
| 5,877,016 A | 3/1999 | Presta et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jakobovits et al. |
| 6,017,878 A | 1/2000 | Saragovi et al. |
| 6,019,968 A | 2/2000 | Platz et al. |
| 6,027,927 A | 2/2000 | Presta et al. |
| 6,054,297 A | 4/2000 | Carter et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,153,189 A | 11/2000 | Presta et al. |
| 6,180,370 B1 | 1/2001 | Queen et al. |
| 6,180,377 B1 | 1/2001 | Morgan et al. |
| 6,194,167 B1 | 2/2001 | Browse et al. |
| 6,204,023 B1 | 3/2001 | Robinson et al. |
| 6,265,150 B1 | 7/2001 | Terstappen et al. |
| 6,291,247 B1 | 9/2001 | Riopelle et al. |
| 6,350,861 B1 | 2/2002 | Co et al. |
| 6,399,780 B1 | 6/2002 | Hudkins |
| 6,492,380 B1 | 12/2002 | Ross et al. |
| 6,548,062 B2 | 4/2003 | Buchkovich et al. |
| 6,548,640 B1 | 4/2003 | Winter |
| 6,649,605 B2 | 11/2003 | Olesen et al. |
| 6,656,465 B2 | 12/2003 | Clary et al. |
| 6,699,658 B1 | 3/2004 | Wittrup et al. |
| 6,774,107 B1 | 8/2004 | Strittmatter et al. |
| 6,790,639 B2 | 9/2004 | Brown et al. |
| 6,797,492 B2 | 9/2004 | Daugherty et al. |
| 6,919,426 B2 | 7/2005 | Boone et al. |
| 7,022,484 B2 | 4/2006 | High et al. |
| 7,029,872 B2 | 4/2006 | Gerngross |
| 7,117,096 B2 | 10/2006 | Luo et al. |
| 7,220,840 B2 | 5/2007 | Ruben et al. |
| 7,252,822 B2 | 8/2007 | Shelton et al. |
| 7,255,860 B2 | 8/2007 | Shelton et al. |
| 7,261,890 B2 | 8/2007 | Krah, III et al. |
| 7,393,648 B2 | 7/2008 | Rother et al. |
| 7,425,329 B2 | 9/2008 | Shelton et al. |
| 7,449,308 B2 | 11/2008 | Gerngross et al. |
| 7,449,616 B2 | 11/2008 | Pons et al. |
| 7,569,364 B2 | 8/2009 | Rosenthal et al. |
| 7,601,352 B1 | 10/2009 | Novak |
| 7,612,181 B2 | 11/2009 | Wu et al. |
| 7,655,231 B2 | 2/2010 | Shelton et al. |
| 7,655,232 B2 | 2/2010 | Pons et al. |
| 7,727,527 B2 | 6/2010 | Shelton |
| 2003/0031671 A1 | 2/2003 | Welt et al. |

FOREIGN PATENT DOCUMENTS

| | | |
|---|---|---|
| WO | WO 1990/10700 A1 | 9/1990 |
| WO | WO 1990/14424 A1 | 11/1990 |
| WO | WO 1990/14443 A1 | 11/1990 |
| WO | WO 1991/05548 A1 | 5/1991 |
| WO | WO 1991/09966 A1 | 7/1991 |
| WO | WO 1991/09967 A1 | 7/1991 |
| WO | WO 1991/10737 A1 | 7/1991 |
| WO | WO 1991/10741 A1 | 7/1991 |
| WO | WO 1992/02551 A1 | 8/1991 |
| WO | WO 1991/14430 A1 | 10/1991 |
| WO | WO 1991/17271 A1 | 11/1991 |
| WO | WO 1992/01047 A1 | 1/1992 |
| WO | WO 1992/03461 A1 | 3/1992 |
| WO | WO 1992/09631 A1 | 6/1992 |
| WO | WO 1992/09690 A2 | 6/1992 |
| WO | WO 1995/15982 A1 | 6/1992 |
| WO | WO 1992/11272 A1 | 7/1992 |
| WO | WO 1992/15679 A1 | 9/1992 |
| WO | WO 1992/18619 A1 | 10/1992 |
| WO | WO 1992/19244 A1 | 11/1992 |
| WO | WO 1992/20791 A1 | 11/1992 |
| WO | WO 1992/22324 A1 | 12/1992 |
| WO | WO 1993/01288 A1 | 1/1993 |
| WO | WO 1993/06213 A1 | 4/1993 |
| WO | WO 1993/11236 A1 | 6/1993 |
| WO | WO 1994/02602 A1 | 2/1994 |
| WO | WO 1994/18219 A1 | 8/1994 |
| WO | WO 1995/20401 A1 | 8/1995 |
| WO | WO 1995/25795 A1 | 9/1995 |
| WO | WO 1996/20698 A1 | 7/1996 |
| WO | WO 1996/33735 A1 | 10/1996 |
| WO | WO 1996/34096 A1 | 10/1996 |
| WO | WO 1997/15593 A1 | 5/1997 |
| WO | WO 1997/20032 A1 | 6/1997 |
| WO | WO 1997/21732 A1 | 6/1997 |
| WO | WO 1997/29131 A1 | 8/1997 |
| WO | WO 1997/32572 A1 | 9/1997 |
| WO | WO 1997/44013 A1 | 11/1997 |
| WO | WO 1998/06048 A2 | 2/1998 |
| WO | WO 1998/16654 A1 | 4/1998 |
| WO | WO 1998/17278 A1 | 4/1998 |
| WO | WO 1998/24893 A2 | 6/1998 |
| WO | WO 1998/31346 A1 | 7/1998 |
| WO | WO 1998/31700 A1 | 7/1998 |
| WO | WO 1998/50433 A2 | 11/1998 |
| WO | WO 1999/06834 A2 | 2/1999 |
| WO | WO 1999/15154 A1 | 4/1999 |
| WO | WO 1999/20253 A1 | 4/1999 |
| WO | WO 1999/45031 A1 | 9/1999 |
| WO | WO 1999/53049 A1 | 10/1999 |
| WO | WO 1999/53055 A2 | 10/1999 |

(56) References Cited

FOREIGN PATENT DOCUMENTS

| | | |
|---|---|---|
| WO | WO 1999/58572 A1 | 11/1999 |
| WO | WO 1999/66903 A2 | 12/1999 |
| WO | WO 2000/37504 A2 | 12/1999 |
| WO | WO 2000/09560 A2 | 2/2000 |
| WO | WO 2000/56772 A1 | 9/2000 |
| WO | WO 2000/69828 A1 | 11/2000 |
| WO | WO 2000/073344 A2 | 12/2000 |
| WO | WO 2001/64247 A2 | 9/2001 |
| WO | WO 2001/77332 A2 | 10/2001 |
| WO | WO 2001/78698 A2 | 10/2001 |
| WO | WO 2001/83525 A2 | 11/2001 |
| WO | WO 2002/072636 A2 | 9/2002 |
| WO | WO 2002/096458 A1 | 12/2002 |
| WO | WO 2002/102232 A2 | 12/2002 |
| WO | WO 2003/022261 A1 | 3/2003 |
| WO | WO 2003/029456 A1 | 4/2003 |
| WO | WO 2003/060080 A2 | 7/2003 |
| WO | WO 2004/026329 A1 | 4/2004 |
| WO | WO 2004/032852 A2 | 4/2004 |
| WO | WO 2004/032870 A2 | 4/2004 |
| WO | WO 2004/058184 A1 | 7/2004 |
| WO | WO 2004/256385 A2 | 7/2004 |
| WO | WO 2004/065560 A2 | 8/2004 |
| WO | WO 2004/073653 A2 | 9/2004 |
| WO | WO 2004/096122 A2 | 11/2004 |
| WO | WO 2005/ 00194 A2 | 1/2005 |
| WO | WO 2005/019266 A2 | 3/2005 |
| WO | WO 2005/061540 A2 | 7/2005 |
| WO | WO 2005/111077 A2 | 11/2005 |
| WO | WO 2005/035575 A3 | 4/2006 |
| WO | WO 2006/077441 A1 | 7/2006 |
| WO | WO 2006/110883 A2 | 10/2006 |
| WO | WO 2006/121558 A2 | 11/2006 |
| WO | WO 2006/131951 A2 | 12/2006 |
| WO | WO 2006/131952 A2 | 12/2006 |
| WO | WO 2008/046033 A2 | 8/2008 |
| WO | WO 2009/023540 A1 | 2/2009 |
| WO | WO 2009/077993 A2 | 6/2009 |
| WO | WO 2009/091972 A2 | 7/2009 |
| WO | WO 2009/150623 A2 | 12/2009 |
| WO | WO 2010/027488 A2 | 3/2010 |
| WO | WO 2012/024650 A2 | 2/2012 |
| WO | WO 2012/153121 A1 | 11/2012 |
| WO | WO 2012/153122 A1 * | 11/2012 |
| WO | WO 2013/034900 A1 | 3/2013 |
| WO | WO 2013/184871 A1 | 12/2013 |

OTHER PUBLICATIONS

Rudikoff et al. (PNAS 79: 1979-1983, 1982).*
MacCallum, et al. (J. Mol. Biol. 262: 732-745, 1996).*
De Pacalis et al. (J. Immunol. 169: 3076-3084, 2002).*
Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
Adey et al. Phage Display of Peptides and Proteins: 277-291 (1996).
Aley et al., Neuroscience 71: 1083-1090 (1996).
Al-Lazikani et al., 273-927-948 (1997).
Aloe et al., Growth Factors 9: 149-155 (1993).
Aloe et al., Int. J. Tiss. Reac XV(4) 139-143 (1993).
Aloe et al., Rheumatol. Int. 14: 249-252 (1995).
Aloe, Clin and Exp Rheum 10: 203-204 (1992).
Aloe, Clin Exp Theumatol 17: 632-633 (1999).
Aloe, et al., Arch. Rheum. 35:351-355 (1992).
Amann et al., Pain 64: 323-329 (1995).
Andreev et al., Pain 63: 109-115 (1995).
Apfel et al., Mol and Cell. Neuro 7: 134-142 (1996).
Apfel, S.C. et al., Neurology, 51: 695-702 (1998).
Armour et al., Eur J Immunol 29: 2613-2624 (1999).
Azzazy et al., Clin. Biochem., 35: 425-445 (2002).
Balint et al., Gene, 137: 109-118 (1993).
Bellamy et al., J. Rheumatol., 15: 1833-1840 (1988).

Bellamy, N., Semin Arthritis Rheum, 18: 14-17 (1989).
Bellini and Viola, Intern J Neuroscience, 51: 329-330 (1990).
Berrera et al., Biophys J, 91: 2063-2071 (2006).
Bibel et al., Genes Dev, 14(23): 2919-2937 (2000).
Bird et al., Science, 242: 423-426 (1988).
Bischoff et al., Blood 79: 2662-2669 (1992).
BLAST Manual, Altschul et al. NCB/NLM/NIH Bethesda, Md. 20894; Altschul et al., (1990).
Boerner et al., J Immuno 147: 86-95 (1991).
Borsani et al., Nucleic Acids Research 18(13) 4020 (1990).
Bracci-Laudiero, et al, Neurosci. Lett. 147:9-12 (1992).
Bracci-Laudiero, et al., Neuroreport 4:563-565 (1993).
Braun, et al., Eur. J Immunol., 28:3240-3251 (1998).
Brennan et al., Anesthesiology Clin N Am 23: 1-20 (2005).
Brennan et al., ILAR Journal 40(3): 129-136 (1999).
Brennan, Soc Neurosci Abstract 349.4 (1998).
Brosseau et al., The Cochrane Database of Systematic Reviews 4: Art No. CD004522 (2003).
Brown et al., Cancer Res 47: 3577-3583 (1987).
Buchman et al., Development 118: 989-1001 (1993).
Calissano et al., Cell Death and Differentiation, 17: 1126-1133 (2010).
Capel et al., , Immunomethods, 4:25-34 (1994).
Caraceni J Pain Symptom Management 23: 239-255 (2002).
Chao, et al., Science 232:518-521 (1986).
Chaplan et al., J Neuro Methods 53: 55-63 (1994).
Choi et al., Life Sciences 73: 471-485 (2003).
Chothia and Lesk J. Mol. Biol. 196:901-917 (1987).
Chothia et al. Nature 342:877-883 (1989).
Chothia et al., J. Mol. Biol., 227:799 (1992).
Christensen and Hulsebosch, Experimental Neurology147(2) :463-475 (1997).
Chun et al., J Cell Biol 75: 705-711 (1977).
Clackson et al., Nature 352:624 628 (1991).
Clohisy et al., Clin Ortho and Rel Res 415S: S279-S288 (2003).
Clynes et al., 1998, PNAS (USA), 95:652-656 (1998).
Computational Molecular Biology, (Lesk, A. M., ed.), 1988, Oxford University Press, New York.
Computer Analysis of Sequence Data, Part 1, (Griffin, A. M., and Griffin, H. G., eds.), 1994, Humana Press, New Jersey.
Covaceuzach et al., J Mol Bio 4: 881-896 (2008).
Covaceuzach et al., PLoS One 7: 1-12 (2012).
Cromartie et al., J Exp Med 146: 1585-1602 (1977).
Crowley et al. Cell 76:1001-1011 (1994).
Daughtery, Nucleic Acids Research 19: 2471-2476 (1991).
De Haas et al., J. Lab. Clin. Med., 126:330-41 (1995).
Dekock et al., Pain 92:373-380 (2001).
Devereux et al., Nucl Acid. Res., 12:387 (1984).
Dicou et al., Autoimmunity 24: 1-9 (1996).
Dicou et al., J Neuroimmun 47(159-167 (1993).
Dicou et al., J. Neuroimmun 75: 200-203 (1997).
Dicou et al., NeuroReport 5: 321-324 (1993).
Dimarco et al., J Biol Chem 268(30) 22838-22846 (1993).
Donnerer et al., Neuroscience 49(3): 693-698 (1992).
Durbin et al., Biological Sequence Analysis, Cambridge University Press. (1998).
Eide et al., J. Neuroscience 16(10) 3123-3129 (1996).
Falcini et al., Ann Rheum Dis 55: 745-748 (1996).
Felson et al., Arthritis Rheumatism 36: 729-740 (1993).
Fjell et al., J. Neurophysiol 81: 803-810 (1999).
Foote and Winter, J Mol Biol 224: 487-499 (1992).
Foster et al., J. Pathol 197: 245-255 (2002).
Fries, J.Rheumatol 9:789-793 (1982).
Garaci et al., PNAS 96(24) 14013-14018 (1999).
Garcia-Castellano et al., Iowa Orthop J 20: 49-58 (2000).
Garrett et al., Neurosci Lett 230: 5-8 (1997).
Gavilondo and Larrick, BioTechniques 29: 128-145 (2000).
Giege, R. and Ducruix, A. Barrett, Crystallization of Nucleic Acids and Proteins, a Practical Approach, 2nd ea., pp. 20 1-16, Oxford University Press, New York, New York, (1999).
Gould et al., Brain Research 854: 19-29 (2000).
Griffiths et al., EMBO 12(2): 725-734 (1993).
Grosschedl et al., 41 Cell 885 (1985).

(56) References Cited

OTHER PUBLICATIONS

Gwak et al., Neurosci Lett 336: 117-120 (2003).
Halvorson et al., Cancer Res 65: 9426-9435 (2005).
Haynes et al., Clinical Immunology 105(3): 315-325 (2002).
Hefti et al., Trends in Pharmacological Sciences 27(2): 85-91 (2006).
Hein, J., Meth Enzymol 183: 626-645 (1990).
Higgins and Sharp, CABIOS Comm 5: 151-153 (1989).
Hill et al., Trends Pharmacol Sci 21(7): 244-246 (2000).
Holliger et al., PNAS 90:6444-6448 (1993).
Hongo et al., Hybridoma 19(3): 215-227 (2000).
Honore et al., Nature med 6: 521-528 (2000).
Honore et al., Neuroscience 98(3): 585-598 (2000).
Honore et al., Prog Brain Res 129: 389-397 (2000).
Hoogenboom and Winter, J Mol Biol 227: 381-388 (1992).
Hoogenboom et al., Immunology Today, 21: 371-378 (2000).
Hoogenboom, TIB Tech., 15: 62-70 (1997).
Horigome, et al., J. Bioi. Chem. 268:14881-14887 (1993).
Huang and Reichardt, Ann Rev. Neurosci 24: 677-736 (2001).
Huse et al.,Intern Rev Immunol 10: 129-137 (1993).
Iannone et al., Rheumatology 41: 1413-1418 (2002).
Informatics and Genome Projects, (Smith, D. W., ed.), Academic Press, New York (1993).
Jefferis, Chem Immunol 65: 111-128 (1997).
Johnson and Chiswell, Curr Opin Structural Biol 3: 564-571 (1993).
Jones et al., Nature 321: 522-525 (1986).
Jones et al., Pain 79: 21-29 (1999).
Jonsson, et al. Ann. Biol. Clin. 51: 19-26 (1993).
Kabat et al., Ann. NY Acad, Sci., 190:382-391 (1971).
Kassel, et al., Clin, Exp. Allergy, 31 : 1432-40 (2001).
Katz and Melzack, Surg Clin North Am 79: 231-252 (1999).
Kawamoto et al., J Immunol 168: 6412-6419 (2002).
Kazemier et al., J Immunol Methods 194: 201-209 (1996).
Kellermann et al., Current Opinion in Biotechnology, 13: 593-597 (2002).
Kidd et al, Br J Anaesthesia 87 (1) 3-11 (2001).
Kim et al., Eur J. Immunol 24: 2429-2434 (1994).
Kipriyanov, et al., Mol. Immunol., 31: 1047-1058 (1994).
Kipriyanov, S.M., et al., Human Antibodies and Hybridomas, 6: 93-101 (1995).
Klein et al., Cell 61: 647-656 (1990).
Knusel et al., J Neurochem 57: 955-962 (1990).
Knusel et al., J Neurochem 59: 715-721 (1992).
Koizumi et al., J.Neurosci 8: 715-721 (1988).
Kontermann and Dubel eds., Antibody Engineering, Springer-Verlag. New York. 790 pp. (ISBN 3-540- 41354-5) (2001).
Kryger, et al., J. Hand Surg. (Am.), 26: 635-644 (2001).
Kuzuna and Kawai, Chem Pharm Bulletin 23: 1184-1191 (1975).
Lamballe et al., EMBO J 12(8): 3083-3094 (1993).
Lane et al., New England Journal of Medicine 363: 1521-1531 (2010).
Lane, N., Osteoarthritis and Cartilage Abstracts 20: S1-S9(2012).
Lefranc et al., Nucleic Acids Res, 27:209-212 (1999).
Leon et al., PNAS 81: 3739-3743 (1994).
Levi-Montalcini and Angeletti, Physiol Rev 48; 534-569 (1968).
Levi-Montalcini, Science 187: 113 (1975).
Lewin et al Eur J Neuroscience 6: 1903-1912 (1994).
Lewin et al., J Neuroscience 13: 2136-2148 (1993).
Li et al., PNAS 95: 10884-10889 (1998).
Linday, R., J Neuroscience 8(7): 2394-2405 (1988).
Lindsholm, et al., Eur. J. Neurosci. 2:795-801 (1990).
Lindsay, et al., Nature 337:362-364 (1989).
Little et al., Immunology Today, 21 : 364-370 (2000).
LoBuglio et al., PNAS 86: 4220-4224 (1989).
Lonberg et al., In Rev Immunol 13:65-93 (1995).
Luger et al. Cancer Research 61: 4038-4047 (2001).
MacCallum (J Mol Biol 262(5):732-45 (1996).
Mach et al., Neuroscience 113(1): 155-166 (2002).
Manni et al., Rheumatol Int 18: 97-102 (1998).
Mantyh et al., Nature Reviews Cancer 2(3): 201-209 (2002).

Marchalonis et al., Adv Exp MedBiol. 484: 13-30 (2001).
Marks et al., Bio Technol 10:779-783 (1992).
Marks et al., J. Mol. Biol. 222:581 597 (1991).
Martin, et al., Proc. Natl. Acad. Sci. USA, 86:9268-9272 (1989).
Matsuda et al., PNAS 85(17):6508-6512 (1988).
Mccafferty et al., Nature 348:552-554 (1990).
McDonald et al., Nature 354:411-414 (1991).
McMahon et al., Nature Medicine 1:774-780 (1995).
McMahon et al., Phil. Trans R. Soc. Land B 351(1338):431-440 (1996).
Meenan et al., Arthritis Rheumatism 25: 1048-1053 (1982).
Milstein, Nature 305: 537-540 (1983).
Moiniche et al., Anesthesiology 96: 725-741 (2002).
Molander and Grant, J Comp Neuro 260: 246-255 (1987).
Molnar et al., Eur J Neuro 10:3127-3140 (1998).
Morrison et al., PNAS 81: 6851-6855 (1984).
Muyldermans Rev Mol Biotech 74: 277-302 (2001).
Myers and Miller, CABIOS 4: 11-17 (1988).
Nanduri et al., J Neuro Res 37: 433-444 (1994).
Niissalo et al., Ann NY Acad Sci 966:384-399 (2002).
Okragly, et al., J. Urology 6: 438-441 (1999).
Otten et al., Eur J Pharm 106(1): 199-201 (1985).
Otten et al., PNAS 86: 10059-10063 (1989).
Owens et al J Immunol Methods 168(2):149-165 (1994).
Padlan Faseb J. 9: 133-139 (1995).
Paulus et al., Arthritis and Rheumatism 33(4) : 477-485 (1990).
Pearce, et al., J. Physiol, 372:379-393 (1986).
Pearson Arthritis-Rheum 2: 440-459 (1959).
Pelat et al., mAbs 1: 377-381 (2009).
Petersen et al., Neuroscience 83: 161-168 (1998).
Petty et al., Annals Neuro 36: 244-246 (1994).
Pluckthun in The Pharmacology of Monoclonal Antibodies, vol. 113, Rosenburg and Moore eds. Springer-Verlag, New York, pp. 269-315 (1994).
Poljak RJ, Structure 15(2): 1121-1123 (1994).
Pollack J Immunol Meth 231: 147-157 (1999).
Pons et al., Protein Science 8: 958-968 (1999).
Pozza et al., J Rheumatol 27(5): 1121-1127 (2000).
Presta, Current Opin Immunol 5-6: 640-656 (2006).
Prodromou and Pearl, Protein Engineering 5(8) 827-829) (1992).
Puigdellivol-Sanchez et al., Neuro Lett 251(3): 169-172 (1998).
Ramer and Bisby, Eur J Neuro 11:837-846 (1999).
Ravetch and Kinet, 1991, Ann. Rev. Immunol., 9:457-92 (1991).
Raychaudhuri Acta Derm Venereol 78: 84-86 (1998).
Riechmann et al., nature 332: 323-327 (1988).
Ro et al., Neuro Letters 218:87-90 (1996).
Ro et al., Pain 79: 265-274 (1999).
Rosak et al., J Biol Chem 271:22611-22618 (1996).
Roubenoff et al., J Clin Inves 93: 2379-2386 (1994).
Roubenoff et al.,Arthritis Rheum 40(3): 534-539 (1997).
Ruberti et al. (1993) Cell. Molec. Neurobiol. 13(5): 559-568 (1993).
Rudikoff et al., PNAS 79: 1979-1963 (1982).
Sambrook et al. Molecular Cloning: A Laboratory Manual (2d ed., Cold Spring Harbor Laboratory Press, Cold Spring Harbor, N.Y. (1989).
Saragovi, et al., Trends Pharmacol Sci. 21 : 93-98 (2000).
Schwartz, et al., J Photochem. Photobiol., B66: 195-200 (2002).
Schwei et al., J Neuro 19(24): 10886-10897 (1999).
Sequence Analysis Primer, (Gribskov, M. and Devereux, J., eds.), 1991, M. Stockton Press, New York; Carillo et al., (1988).
Sevcik et al., Pain 115: 128-141 (2005).
Shapiro et al., Crit. Rev. Immunol. 22(3): 183-200 (2002).
Shaw et al., J Immunol 138(12): 4534-4538 (1987).
Sheets et al., PNAS 95: 6157-6162 (1998).
Shelton and Reichardt, PNAS 81: 7951-7955 (1984).
Shelton et al., Rest Neurol and Neuro 8 : 99-100 (1995).
Shih et al., J Biol Chem 269: 27679-27686 (1994).
Smeyne, et al, Nature 368:246-249 (1994).
Stanisz., Annals of NY Acad Sci 917(1): 268-272 (2000).
Steiner, et al., Am. J. Physiol., 261 :F792-798 (1991).
Szekanecz et al., Arth Rheum 43 (6): 1266-1277 (2000).
Taglialatela et al., J Neurochem 66: 1826-1835 (1996).
Taylor, L. D., et al. (1992) Nucl. Acids Res. 20:6287-6295 (1992).

(56) References Cited

OTHER PUBLICATIONS

Torcia, et al, Cell 85:345-356 (1996).
Ueyama, et al, J Hypertens. 11: 1061-1065 (1993).
Ullrich et al., Nature 303: 821-825 (1983).
Umana etl al Nature Biotech 17:176-180 (1999).
Urfer et al., Biochemisry 36: 4775-4781 (1997).
Vajdos et al., J Mol Biol 320: 415-428 (2002).
Vanderah et al., pain 92: 5-9 (2001).
Vaughn et al., Nat Biotech 14: 309-314 (1996).
Verhoeyen et al., Science 239: 1534-1536 (1988).
Vigneti et al., Year Immunol 7: 146-149 (2000).
Von Heinje, G., Sequence Analysis in Molecular Biology, Academic Press (1987).
Waterhouse et al., Nucleic Acids Res 21: 2265-2266 (1993).
Wiesmann et al., Nature 401: 184-188 (1999).
Wilbur and Lipman PNAS 80: 726-730 (1983).
Winnaker, From Genes to Clones (Verlagsgesellschaft, Weinheim, Germany (1987).
Winter and Milstein, Nature 349: 293-299 (1991).
Winter et al., Ann Rev Immunol 12: 433-455 (1994).
Winter et al., Arth Rheum 9: 394-404 (1966).
Woolf et al., J Neurosci 16(8): 2716-2723 (1996).
Woolf et al., J Neurosci 21(3): 1047-1055 (2001).
Woolf et al, Neuroscience 62: 327-331 (1994).
Wright and Morrison, TibTech 15: 26-32(1997).
Wyss and Wagner, Curr Opin Biotech 7: 409-416 (1996).
Yamamoto et al., Brain Res 909: 138-144 (2001).
Yan et al., Clinical Science 80: 565-569 (1991).
Yelton et al., JImmunol 155: 1994-2004 (1995).
Yu et al., J Neurosci Meth 115: 107-113 (2002).
Zahn et al., J Pain 5(3): 157-163 (2004).
Zahn et al., Reg Anesth Pain Med 27: 514-516 (2002).
Zhu, Z et al., J Clin. Oncol., 17: 241-228 (1999).
Gearing, D. P. et al. "A fully caninised anti-NGF monoclonal antibody for pain relief in dogs", BMC Veterinary Research, 2013, vol. 9, p. 226.
Lascelles, B. D. X. et al. "A canine-specific anti-nerve growth factor antibody alleviates pain and improves mobility and function in dogs with degenerative joint disease-associated pain", BMC Veterinary Research, 2015, vol. 11, p. 101.
Gruen, M. E. et al. "A Feline-Specific Anti-Nerve Growth Factor Antibody Improves Mobility in Cats with Degenerative Joint Disease-Associated Pain: A Pilot Proof of Concept Study", 2016, Journal of Veterinary Internal Medicine, 2016, vol. 30, pp. 1138-1148.
Gearing, D. P. et al. "In Vitro and In Vivo Characterization of a Fully Felinized Therapeutic Anti-Nerve Growth Factor Monoclonal Antibody for the Treatment of Pain in Cats", 2016, Journal of Veterinary Internal Medicine, vol. 30, pp. 1129-1137.
Panka, D. et al. "Defining the Structural Correlates Responsible for Loss of Arsonate Affinity in an $Id^{CR}$ Antibody Isolated from an Autoimmune Mouse", Molecular Immunology, 1993, vol. 30, pp. 1013-1020.
Kobrin, B. J. et al. "A V region mutation in a phosphocholine-binding monoclonal antibody results in loss of antigen binding", The Journal of Immunology, 1991, vol. 146, pp. 2017-2020.
Chien, N. C. et al. "Significant structural and functional change of an antigen-binding site by a distant amino acid substitution: Proposal of a structural mechanism", Proceedings of the National Academy of Science USA, 1989, vol. 86, pp. 5532-5536.
Rudikoff, S. et al. "Single amino acid substitution altering antigen-binding specificity", Proceedings of the National Academy of Science USA., 1982, vol. 79, pp. 1979-1983.
Winkler, K. et al. "Changing the Antigen Binding Specificity by Single Point Mutations of an Anti-p24 (HIV-1) Antibody", Journal of Immunology, 2000, vol. 165, pp. 4505-4514.
Kobayashi, I. et al. "Tryptophan H33 plays an important role in pyrimidine (6-4) pyrimidone photoproduct binding by a high-affinity antibody", Protein Engineering, 1999, vol. 12, pp. 879-884.
Casipit, C. L. et al. "Improving the binding affinity of an antibody using molecular modeling and site-directed mutagenesis", Protein Science, 1998, vol. 7, pp. 1671-1680.
Schildbach, J. F. et al. "Modulation of antibody affinity by a non-contact residue", Protein Science, 1993, vol. 2, pp. 206-214.
Betts, M. J. et al. "Amino Acid Properties and Consequences of substitutions", Bioinformatics for Geneticists, 2003, Chapter 14, pp. 289-316.

\* cited by examiner

SEQUENCE LISTING

<160> NUMBER OF SEQ ID NOS: 92

<210> SEQ ID NO 1
<211> LENGTH: 8
<212> TYPE: PRT
<213> ORGANISM: Canis familiaris

<400> SEQUENCE: 1

Thr Asn Asn Ile Gly Ile Leu Gly
1               5

<210> SEQ ID NO 2
<211> LENGTH: 3
<212> TYPE: PRT
<213> ORGANISM: Canis familiaris

<400> SEQUENCE: 2

Gly Asn Gly
1

<210> SEQ ID NO 3
<211> LENGTH: 11
<212> TYPE: PRT
<213> ORGANISM: Canis familiaris

<400> SEQUENCE: 3

Gln Ser Phe Asp Thr Thr Leu Gly Ala His Val
1               5                   10

<210> SEQ ID NO 4
<211> LENGTH: 8
<212> TYPE: PRT
<213> ORGANISM: Canis familiaris

<400> SEQUENCE: 4

Gly Phe Thr Phe Ser Ser His Gly
1               5

<210> SEQ ID NO 5
<211> LENGTH: 8
<212> TYPE: PRT
<213> ORGANISM: Canis familiaris

<400> SEQUENCE: 5

Ile Asn Ser Gly Gly Ser Ser Thr
1               5

<210> SEQ ID NO 6
<211> LENGTH: 18
<212> TYPE: PRT
<213> ORGANISM: Canis familiaris

<400> SEQUENCE: 6

Ala Lys Glu Ser Val Gly Gly Trp Glu Gln Leu Val Gly Pro His Phe
1               5                   10                  15

Asp Tyr

<210> SEQ ID NO 7
<211> LENGTH: 110
<212> TYPE: PRT
<213> ORGANISM: Canis familiaris

```
<400> SEQUENCE: 7

Gln Ser Val Leu Thr Gln Pro Thr Ser Val Ser Gly Ser Leu Gly Gln
1               5                   10                  15

Arg Val Thr Ile Ser Cys Ser Gly Ser Thr Asn Asn Ile Gly Ile Leu
            20                  25                  30

Gly Ala Ser Trp Tyr Gln Leu Phe Pro Gly Lys Ala Pro Lys Leu Leu
        35                  40                  45

Val Tyr Gly Asn Gly Asn Arg Pro Ser Gly Val Pro Asp Arg Phe Ser
    50                  55                  60

Gly Ala Asp Ser Gly Asp Ser Val Thr Leu Thr Ile Thr Gly Leu Gln
65                  70                  75                  80

Ala Glu Asp Glu Ala Asp Tyr Tyr Cys Gln Ser Phe Asp Thr Thr Leu
                85                  90                  95

Gly Ala His Val Phe Gly Gly Gly Thr His Leu Thr Val Leu
            100                 105                 110

<210> SEQ ID NO 8
<211> LENGTH: 125
<212> TYPE: PRT
<213> ORGANISM: Canis familiaris

<400> SEQUENCE: 8

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser His
            20                  25                  30

Gly Met His Trp Val Arg Gln Ser Pro Gly Lys Gly Leu Gln Trp Val
        35                  40                  45

Ala Val Ile Asn Ser Gly Gly Ser Thr Tyr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Met Tyr Tyr Cys
                85                  90                  95

Ala Lys Glu Ser Val Gly Gly Trp Glu Gln Leu Val Gly Pro His Phe
            100                 105                 110

Asp Tyr Trp Gly Gln Gly Thr Leu Val Ile Val Ser Ser
        115                 120                 125

<210> SEQ ID NO 9
<211> LENGTH: 110
<212> TYPE: PRT
<213> ORGANISM: Canis familiaris

<400> SEQUENCE: 9

Gln Ser Val Leu Thr Gln Pro Thr Ser Val Ser Gly Ser Leu Gly Gln
1               5                   10                  15

Arg Val Thr Ile Ser Cys Ser Gly Ser Thr Asn Asn Ile Gly Ile Leu
            20                  25                  30

Gly Ala Ser Trp Tyr Gln Leu Phe Pro Gly Lys Ala Pro Lys Leu Leu
        35                  40                  45

Val Tyr Gly Asn Gly Asn Arg Pro Ser Gly Val Pro Asp Arg Phe Ser
    50                  55                  60

Gly Ala Asp Ser Gly Asp Ser Val Thr Leu Thr Ile Thr Gly Leu Gln
65                  70                  75                  80
```

Ala Glu Asp Glu Ala Asp Tyr Tyr Cys Gln Ser Phe Asp Thr Thr Leu
            85                  90                  95

Gly Ala His Val Phe Gly Gly Gly Thr His Leu Thr Val Leu
        100                 105                 110

<210> SEQ ID NO 10
<211> LENGTH: 125
<212> TYPE: PRT
<213> ORGANISM: Canis familiaris

<400> SEQUENCE: 10

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser His
            20                  25                  30

Gly Met His Trp Val Arg Gln Ser Pro Gly Lys Gly Leu Gln Trp Val
        35                  40                  45

Ala Val Ile Asn Ser Gly Gly Ser Ser Thr Tyr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Met Tyr Tyr Cys
                85                  90                  95

Ala Lys Glu Ser Val Gly Gly Trp Glu Gln Leu Val Gly Pro His Phe
            100                 105                 110

Asp Tyr Trp Gly Gln Gly Thr Leu Val Ile Val Ser Ser
        115                 120                 125

<210> SEQ ID NO 11
<211> LENGTH: 24
<212> TYPE: DNA
<213> ORGANISM: Canis familiaris

<400> SEQUENCE: 11
acgaacaaca tcggtattct tggt                                          24

<210> SEQ ID NO 12
<211> LENGTH: 9
<212> TYPE: DNA
<213> ORGANISM: Canis familiaris

<400> SEQUENCE: 12 ggtaatggg                                                            9

<210> SEQ ID NO 13
<211> LENGTH: 36
<212> TYPE: DNA
<213> ORGANISM: Canis familiaris

<400> SEQUENCE: 13
cagtcctttg ataccacgct tggtgctcat gtgttc                             36

<210> SEQ ID NO 14
<211> LENGTH: 24
<212> TYPE: DNA
<213> ORGANISM: Canis familiaris

<400> SEQUENCE: 14
ggattcacct tcagtagcca cggc                                          24

```
<210> SEQ ID NO 15
<211> LENGTH: 24
<212> TYPE: DNA
<213> ORGANISM: Canis familiaris

<400> SEQUENCE: 15
attaacagcg gtggaagtag caca                                              24

<210> SEQ ID NO 16
<211> LENGTH: 54
<212> TYPE: DNA
<213> ORGANISM: Canis familiaris

<400> SEQUENCE: 16
gcaaaggagt ccgtcggggg gtgggagcaa ctggtcggac ctcattttga ctac             54

<210> SEQ ID NO 17
<211> LENGTH: 330
<212> TYPE: DNA
<213> ORGANISM: Canis familiaris

<400> SEQUENCE: 17
cagtctgtgc tgactcagcc gacctcagtg tcagggtccc ttggccagag ggtcaccatc       60
tcctgctctg gaagcacgaa caacatcggt attcttggtg cgagctggta ccaactgttc      120
ccaggaaagg cccctaaaact cctcgtgtac ggtaatggga atcgaccgtc aggggtccct     180
gaccggtttt ccggcgccga ctctggcgac tcagtcaccc tgaccatcac tgggcttcag     240
gctgaggacg aggctgatta ttactgccag tcctttgata ccacgcttgg tgctcatgtg     300
ttcggcggag gcacccacct gaccgtcctt                                       330

<210> SEQ ID NO 18
<211> LENGTH: 375
<212> TYPE: DNA
<213> ORGANISM: Canis familiaris

<400> SEQUENCE: 18
gaggtgcagc tggtggagtc tgggggagat ttggtgaagc ctgggggggtc cttgagactg      60 tcctgtgtgg cctctggatt caccttcagt agccacggca tgcactgggt ccgtcagtct     120
ccagggaagg gactgcagtg ggtcgcagtt attaacagcg gtggaagtag cacatactac     180
acagacgctg tgaagggccg attcaccatc tccagagaca cgccaagaa cacagtgtat      240 ctacagatga acagcctgag agccgaggac acggccatgt attactgtgc aaaggagtcc    300 gtcgggggt gggagcaact ggtcggacct cattttgact actggggcca gggaaccctg     360
gtcatcgtct cgagc                                                       375

<210> SEQ ID NO 19
<211> LENGTH: 333
<212> TYPE: DNA
<213> ORGANISM: Canis familiaris

<400> SEQUENCE: 19
caggcggtgc tgaaccagcc ggcgagcgtg agcggcgcgc tgggccagaa agtgaccatt       60
agctgcagcg gcagcaccat ggatattgat attttggcg tgagctggta tcagcagctg      120
ccgggcaaag cgccgaaact gctggtggat agcgatggc atcgcccgag cggcattccg      180
gatcgcttta gcggcagccg cagcggcaac agcggcaccc tgaccattac cggcctgcag     240
```

```
gcggaagatg aagcggatta tcattgccag agcggcgata gcaccctggg cgcgctggcg    300 attttttggcg gcggcaccca tgtgaccgtg ctg                                333
```

<210> SEQ ID NO 20
<211> LENGTH: 375
<212> TYPE: DNA
<213> ORGANISM: Canis familiaris

<400> SEQUENCE: 20

```
gaagtgcagc tggtggaaag cggcggcgat ctggtgaaac cgggcggcag cctgcgcctg     60
agctgcgtgg cgagcggctt tacctttagc agccatggca tgcattgggt gcgccagagc    120
ccgggcaaag gcctgcagtg ggtggcggtg attaacagcg gcggcagcag cacctattat    180
accgatgcgg tgaaaggccg ctttaccatt agccgcgata cgcgaaaaa caccgtgtat    240 ctgcagatga acagcctgcg cgcggaagat accgcgatgt attattgcgc gaaagaaagc    300
gtgggcggct gggaacagct ggtgggcccg cattttgatt attggggcca gggcaccctg    360
gtgattgtct cgagc                                                     375
```

<210> SEQ ID NO 21
<211> LENGTH: 8
<212> TYPE: PRT
<213> ORGANISM: Canis familiaris

<400> SEQUENCE: 21

```
Thr Met Asp Ile Asp Ile Phe Gly
1               5
```

<210> SEQ ID NO 22
<211> LENGTH: 3
<212> TYPE: PRT
<213> ORGANISM: Canis familiaris

<400> SEQUENCE: 22

```
Ser Asp Gly
1
```

<210> SEQ ID NO 23
<211> LENGTH: 12
<212> TYPE: PRT
<213> ORGANISM: Canis familiaris

<400> SEQUENCE: 23

```
Gln Ser Gly Asp Ser Thr Leu Gly Ala Leu Ala Ile
1               5                   10
```

<210> SEQ ID NO 24
<211> LENGTH: 8
<212> TYPE: PRT
<213> ORGANISM: Canis familiaris

<400> SEQUENCE: 24

```
Gly Phe Thr Phe Ser Thr Tyr Gly
1               5
```

<210> SEQ ID NO 25
<211> LENGTH: 8
<212> TYPE: PRT
<213> ORGANISM: Canis familiaris

<400> SEQUENCE: 25

Ile Ser Ser Gly Gly Ser Ser Thr
1               5

<210> SEQ ID NO 26
<211> LENGTH: 17
<212> TYPE: PRT
<213> ORGANISM: Canis familiaris

<400> SEQUENCE: 26

Ala Gly Ser Arg Tyr Thr Tyr Ala Tyr Gly Gly Gly Tyr Glu Phe His
1               5                   10                  15

Phe

<210> SEQ ID NO 27
<211> LENGTH: 111
<212> TYPE: PRT
<213> ORGANISM: Canis familiaris

<400> SEQUENCE: 27

Gln Ala Val Leu Asn Gln Pro Ala Ser Val Ser Gly Ala Leu Gly Gln
1               5                   10                  15

Lys Val Thr Ile Ser Cys Ser Gly Ser Thr Met Asp Ile Asp Ile Phe
            20                  25                  30

Gly Val Ser Trp Tyr Gln Leu Pro Gly Lys Ala Pro Lys Leu Leu
        35                  40                  45

Val Asp Ser Asp Gly Asp Arg Pro Ser Gly Ile Pro Asp Arg Phe Ser
50                  55                  60

Gly Ser Arg Ser Gly Asn Ser Gly Thr Leu Thr Ile Thr Gly Leu Gln
65                  70                  75                  80

Ala Glu Asp Glu Ala Asp Tyr His Cys Gln Ser Gly Asp Ser Thr Leu
                85                  90                  95

Gly Ala Leu Ala Ile Phe Gly Gly Thr His Val Thr Val Leu
            100                 105                 110

<210> SEQ ID NO 28
<211> LENGTH: 124
<212> TYPE: PRT
<213> ORGANISM: Canis familiaris

<400> SEQUENCE: 28

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Thr Tyr
            20                  25                  30

Gly Ile Asn Trp Val Arg Gln Ala Pro Gly Lys Gly Leu Gln Trp Val
        35                  40                  45

Ala Tyr Ile Ser Ser Gly Ser Ser Thr Tyr Ala Asp Pro Val
    50                  55                  60

Lys Gly Arg Phe Thr Ile Ser Arg Asp Asp Ala Lys Asn Met Leu Tyr
65                  70                  75                  80

Leu Gln Met Asn Ser Leu Arg Ala Glu Asp Thr Ala Ile Tyr Tyr Cys
                85                  90                  95

Ala Gly Ser Arg Tyr Thr Tyr Ala Tyr Gly Gly Gly Tyr Glu Phe His
            100                 105                 110

Phe Trp Gly Gln Gly Thr Leu Val Thr Val Ser Ser
        115                 120

<210> SEQ ID NO 29
<211> LENGTH: 110
<212> TYPE: PRT
<213> ORGANISM: Canis familiaris

<400> SEQUENCE: 29

Gln Ser Val Leu Thr Gln Pro Thr Ser Val Ser Gly Ser Leu Gly Gln
1               5                   10                  15

Arg Val Thr Ile Ser Cys Ser Gly Ser Thr Asn Asn Ile Gly Ile Leu
            20                  25                  30

Gly Ala Ser Trp Tyr Gln Leu Phe Pro Gly Lys Ala Pro Lys Leu Leu
        35                  40                  45

Val Tyr Gly Asn Gly Asn Arg Pro Ser Gly Val Pro Asp Arg Phe Ser
    50                  55                  60

Gly Ala Asp Ser Gly Asp Ser Val Thr Leu Thr Ile Thr Gly Leu Gln
65                  70                  75                  80

Ala Glu Asp Glu Ala Asp Tyr Tyr Cys Gln Ser Phe Asp Thr Thr Leu
                85                  90                  95

Gly Ala His Val Phe Gly Gly Gly Thr His Leu Thr Val Leu
            100                 105                 110

<210> SEQ ID NO 30
<211> LENGTH: 124
<212> TYPE: PRT
<213> ORGANISM: Canis familiaris

<400> SEQUENCE: 30

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Thr Tyr
            20                  25                  30

Gly Ile Asn Trp Val Arg Gln Ala Pro Gly Lys Gly Leu Gln Trp Val
        35                  40                  45

Ala Tyr Ile Ser Ser Gly Gly Ser Ser Thr Tyr Tyr Ala Asp Pro Val
    50                  55                  60

Lys Gly Arg Phe Thr Ile Ser Arg Asp Asp Ala Lys Asn Met Leu Tyr
65                  70                  75                  80

Leu Gln Met Asn Ser Leu Arg Ala Glu Asp Thr Ala Ile Tyr Tyr Cys
                85                  90                  95

Ala Gly Ser Arg Tyr Thr Tyr Ala Tyr Gly Gly Gly Tyr Glu Phe His
            100                 105                 110

Phe Trp Gly Gln Gly Thr Leu Val Thr Val Ser Ser
        115                 120

<210> SEQ ID NO 31
<211> LENGTH: 24
<212> TYPE: DNA
<213> ORGANISM: Canis familiaris

<400> SEQUENCE: 31
acaatggaca ttgatatatt tggt                                          24

<210> SEQ ID NO 32
<211> LENGTH: 9
<212> TYPE: DNA
<213> ORGANISM: Canis familiaris

```
<400> SEQUENCE: 32 agtgatggg                                                            9

<210> SEQ ID NO 33
<211> LENGTH: 36
<212> TYPE: DNA
<213> ORGANISM: Canis familiaris

<400> SEQUENCE: 33
cagtctggtg attccacgct tggtgccctt gctatt                             36

<210> SEQ ID NO 34
<211> LENGTH: 24
<212> TYPE: DNA
<213> ORGANISM: Canis familiaris

<400> SEQUENCE: 34
ggattcacct tcagtaccta tggc                                          24

<210> SEQ ID NO 35
<211> LENGTH: 24
<212> TYPE: DNA
<213> ORGANISM: Canis familiaris

<400> SEQUENCE: 35
attagtagtg gtggaagtag caca                                          24

<210> SEQ ID NO 36
<211> LENGTH: 51
<212> TYPE: DNA
<213> ORGANISM: Canis familiaris

<400> SEQUENCE: 36
gcgggtagta gatatacata tgcatacgga ggaggatatg agtttcactt c            51

<210> SEQ ID NO 37
<211> LENGTH: 333
<212> TYPE: DNA
<213> ORGANISM: Canis familiaris

<400> SEQUENCE: 37
caggctgtgc tgaatcagcc ggcctcagtg tctggggccc tgggccagaa ggtcaccatc    60
tcctgctctg gaagcacaat ggacattgat atatttggtg tgagctggta ccaacagctc   120
ccaggaaagg cccctaaact cctcgtggac agtgatgggg atcgaccctc agggatccct   180
gacagatttt ctggctccag gtctggcaac tcaggcaccc tgaccatcac tgggctccag   240
gctgaggacg aggctgatta tcactgtcag tctggtgatt ccacgcttgg tgcccttgct   300
attttcggcg gaggcaccca tgtgaccgtc ctt                                333

<210> SEQ ID NO 38
<211> LENGTH: 372
<212> TYPE: DNA
<213> ORGANISM: Canis familiaris

<400> SEQUENCE: 38
gaggtacaac tggtggaatc tgggggagac ctggtgaagc tgggggatc cctgagactc     60 tcctgtgtgg cctctggatt caccttcagt acctatggca tcaactgggt ccgccaggct   120
ccagggaagg ggctgcagtg ggtcgcatac attagtagtg gtggaagtag cacatactat   180
```

```
gcagatcctg tgaagggccg gttcaccatc tccagagacg acgccaagaa catgctgtat        240
cttcagatga acagcctgag agccgaggac acggccatat attactgtgc gggtagtaga        300
tatacatatg catacggagg aggatatgag tttcacttct ggggccaggg aaccctggtc        360
accgtctcga gc                                                            372
```

<210> SEQ ID NO 39
<211> LENGTH: 333
<212> TYPE: DNA
<213> ORGANISM: Canis familiaris

<400> SEQUENCE: 39

```
caggcggtgc tgaaccagcc ggcgagcgtg agcggcgcgc tgggccagaa agtgaccatt        60
agctgcagcg gcagcaccat ggatattgat atttttggcg tgagctggta tcagcagctg       120
ccgggcaaag cgccgaaact gctggtggat agcgatggca tcgcccgag cggcattccg        180 gatcgcttta gcggcagccg cagcggcaac agcggcaccc tgaccattac cggcctgcag       240
gcggaagatg aagcggatta tcattgccag agcggcgata gcaccctggg cgcgctggcg       300 attttggcg gcggcacccc tgtgaccgtg ctg                                     333
```

<210> SEQ ID NO 40
<211> LENGTH: 372
<212> TYPE: DNA
<213> ORGANISM: Canis familiaris

<400> SEQUENCE: 40

```
gaagtgcagc tggtggaaag cggcggcgat ctggtgaaaac cgggcggcag cctgcgcctg        60
agctgcgtgg cgagcggctt tacctttagc acctatggca ttaactgggt gcgccaggcg       120
ccgggcaaag gcctgcagtg gtggcgtat attagcagcg gcggcagcag cacctattat       180
gcggatccgg tgaaaggccg ctttaccatt agccgcgatg atgcgaaaaa catgctgtat       240
ctgcagatga acagcctgcg cgcggaagat accgcgattt attattgcgc gggcagccgc       300 tataccctatg cgtatggcgg cggctatgaa tttcattttt ggggccaggg caccctggtg       360
accgtctcga gc                                                            372
```

<210> SEQ ID NO 41
<211> LENGTH: 335
<212> TYPE: PRT
<213> ORGANISM: Canis familiaris

<400> SEQUENCE: 41

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110
```

```
Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
        290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335

<210> SEQ ID NO 42
<211> LENGTH: 1005
<212> TYPE: DNA
<213> ORGANISM: Canis familiaris

<400> SEQUENCE: 42
gcctcaacaa ctgctcctag cgtgtttccc ctggccccta gctgcggaag tacctcaggc    60
agcacagtgg ccctggcttg tctggtgtct ggatatttcc ctgagccagt gaccgtgagt   120
tggaacagcg gctctctgac ctccggggtg cacacatttc catctgtgct gcagtctagt   180
ggcctgtact ccctgtcaag catggtgact gtgccttcct ctaggtggcc atcagaaact   240
ttcacctgca acgtggccca tcccgccagc aagaccaaag tggacaagcc cgtgcctaaa   300
agggagaatg gaagggtgcc aagaccacct gattgcccta gtgtccagct ccagaaatg    360 ctgggaggac caagcgtgtt catctttcca cccaagccca agacacact gctgattgct    420 agaactcccg aggtgacctg cgtggtggtg gacctggatc cagaggaccc cgaagtgcag   480
atctcctggt tcgtggatgg aagcagatg cagacagcca aaactcagcc tcgggaggaa    540
cagtttaacg gaacctatag agtggtgtct gtgctgccaa ttggacacca ggactggctg   600
aagggcaaac agtttacatg caaggtgaac aacaaggccc tgcctagtcc aatcgagagg   660
actatttcaa agctaggggg acaggctcat cagccttccg tgtatgtgct gcctccatcc   720
cgggaggaac tgtctaagaa cacagtgagt ctgacttgtc tgatcaaaga tttctttccc   780
cctgacattg atgtggagtg gcagagcaat gggcagcagg agccagaatc caagtacaga   840
accacaccac cccagctgga cgaagatggc tcctatttcc tgtacagtaa gctgtcagtg   900
```

```
gacaaatcta ggtggcagcg cggggatacc tttatctgcg ccgtgatgca cgaggctctg    960
cacaatcatt acacacaaga aagtctgtca catagccccg gcaag                  1005
```

<210> SEQ ID NO 43
<211> LENGTH: 335
<212> TYPE: PRT
<213> ORGANISM: Canis familiaris

<400> SEQUENCE: 43

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Ala Ala Gly Ala Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335
```

<210> SEQ ID NO 44
<211> LENGTH: 1005

```
<212> TYPE: DNA
<213> ORGANISM: Canis familiaris

<400> SEQUENCE: 44
gcctcaacaa ctgctcctag cgtgtttccc ctggccccta gctgcggaag tacctcaggc      60
agcacagtgg ccctggcttg tctggtgtct ggatatttcc ctgagccagt gaccgtgagt     120
tggaacagcg gctctctgac ctccggggtg cacacatttc catctgtgct gcagtctagt     180
ggcctgtact ccctgtcaag catggtgact gtgccttcct ctaggtggcc atcagaaact     240
ttcacctgca acgtggccca tcccgccagc aagaccaaag tggacaagcc cgtgcctaaa     300
agggagaatg gaagggtgcc aagaccacct gattgcccta gtgtccagc tccagaagcg      360
gcgggagcac caagcgtgtt catctttcca cccaagccca agacacact gctgattgct      420
agaactcccg aggtgacctg cgtggtggtg gacctggatc cagaggaccc cgaagtgcag     480
atctcctggt tcgtggatgg gaagcagatg cagacagcca aaactcagcc tcgggaggaa     540
cagtttaacg gaacctatag agtggtgtct gtgctgccaa ttggacacca ggactggctg     600
aagggcaaac agtttacatg caaggtgaac aacaaggccc tgcctagtcc aatcgagagg     660
actatttcaa aagctagggg acaggctcat cagccttccg tgtatgtgct gcctccatcc     720
cgggaggaac tgtctaagaa cacagtgagt ctgacttgtc tgatcaaaga tttctttccc     780
cctgacattg atgtggagtg gcagagcaat gggcagcagg agccagaatc caagtacaga     840
accacaccac cccagctgga cgaagatggc tcctatttcc tgtacagtaa gctgtcagtg     900
gacaaatcta ggtggcagcg cggggatacc tttatctgcg ccgtgatgca cgaggctctg     960
cacaatcatt acacacaaga aagtctgtca catagccccg gcaag                    1005

<210> SEQ ID NO 45
<211> LENGTH: 6
<212> TYPE: PRT
<213> ORGANISM: Canis familiaris

<400> SEQUENCE: 45

Asn Ile Gly Ser Lys Asp
1               5

<210> SEQ ID NO 46
<211> LENGTH: 3
<212> TYPE: PRT
<213> ORGANISM: Canis familiaris

<400> SEQUENCE: 46

Ser Asp Ser
1

<210> SEQ ID NO 47
<211> LENGTH: 11
<212> TYPE: PRT
<213> ORGANISM: Canis familiaris

<400> SEQUENCE: 47

Gln Val Trp Asp Ile Ser Ala Asp Ala Ile Val
1               5                   10

<210> SEQ ID NO 48
<211> LENGTH: 8
<212> TYPE: PRT
<213> ORGANISM: Canis familiaris
```

<400> SEQUENCE: 48

Gly Tyr Thr Phe Thr Asp Tyr Tyr
1               5

<210> SEQ ID NO 49
<211> LENGTH: 8
<212> TYPE: PRT
<213> ORGANISM: Canis familiaris

<400> SEQUENCE: 49

Ile Asp Pro Gly Asn Gly Ala Thr
1               5

<210> SEQ ID NO 50
<211> LENGTH: 13
<212> TYPE: PRT
<213> ORGANISM: Canis familiaris

<400> SEQUENCE: 50

Ala Pro Leu Gly Tyr Val Pro Ala Ser Thr Ser Glu Tyr
1               5                   10

<210> SEQ ID NO 51
<211> LENGTH: 108
<212> TYPE: PRT
<213> ORGANISM: Canis familiaris

<400> SEQUENCE: 51

Ser Tyr Val Leu Thr Gln Pro Pro Ser Val Thr Val Thr Leu Arg Gln
1               5                   10                  15

Thr Ala His Ile Thr Cys Gly Gly Asp Asn Ile Gly Ser Lys Asp Val
            20                  25                  30

Tyr Trp Tyr Gln Gln Lys Pro Gly Gln Ala Pro Val Leu Ile Ile Tyr
        35                  40                  45

Ser Asp Ser Lys Arg Pro Thr Gly Ile Pro Glu Arg Phe Ser Gly Ser
    50                  55                  60

Asn Ser Gly Asn Met Ala Thr Leu Thr Ile Ser Gly Ala Leu Ala Glu
65                  70                  75                  80

Asp Glu Ala Asp Tyr Tyr Cys Gln Val Trp Asp Ile Ser Ala Asp Ala
                85                  90                  95

Ile Val Phe Gly Gly Gly Thr His Leu Thr Val Leu
            100                 105

<210> SEQ ID NO 52
<211> LENGTH: 120
<212> TYPE: PRT
<213> ORGANISM: Canis familiaris

<400> SEQUENCE: 52

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Thr Phe Thr Asp Tyr
            20                  25                  30

Tyr Met His Trp Val Gln Gln Ala Pro Gly Ala Gly Leu Asn Trp Met
        35                  40                  45

Gly Arg Ile Asp Pro Gly Asn Gly Ala Thr Arg Tyr Ala Gln Lys Phe
    50                  55                  60

Gln Gly Arg Leu Thr Leu Thr Ala Asp Thr Ser Thr Ser Thr Ala Tyr
65                  70                  75                  80

```
Met Glu Leu Ser Gly Leu Arg Ala Glu Asp Thr Ala Val Tyr Tyr Cys
                85                  90                  95

Ala Pro Leu Gly Tyr Val Pro Ala Ser Thr Ser Glu Tyr Trp Gly Gln
            100                 105                 110

Gly Thr Leu Val Ser Val Ser Ser
        115                 120

<210> SEQ ID NO 53
<211> LENGTH: 324
<212> TYPE: DNA
<213> ORGANISM: Canis familiaris

<400> SEQUENCE: 53
tcctatgtgc tgacccagcc accatcagtg actgtgaccc tgaggcagac ggcccacatc      60
acctgtgggg agacaacat tggaagtaaa gatgtttatt ggtaccagca gaagccgggc     120
caggcccccg tgttgattat ctatagtgat agcaagaggc cgacagggat ccctgagcga     180
ttctccggct ccaactcggg gaacatggcc accctgacca tcagtggggc cttggcggag     240
gatgaggctg actattactg ccaggtatgg gacatcagtg ctgatgctat tgtgttcggc     300
ggaggcaccc atctgaccgt cctt                                           324

<210> SEQ ID NO 54
<211> LENGTH: 360
<212> TYPE: DNA
<213> ORGANISM: Canis familiaris

<400> SEQUENCE: 54
gaggtccagc tggtgcagtc tgcagctgag gttaagaagc caggggcatc tgtaaaggtc      60
tcctgcaaga cctctggata caccttcact gactactata tgcactgggt acaacaggct     120
ccaggagcag ggctcaattg gatgggacgg attgatcctg aaatggtgca caaggtat      180 gcacagaagt tccagggcag actcaccctg acggcagaca tccacaagac acagcctac      240 atggagctga gcggtctgag agctgaggac acagctgtgt actactgtgc cccctaggg     300 tacgtgcctg catcaacatc tgagtactgg ggccagggca ccctggtcag cgtctcgagc     360

<210> SEQ ID NO 55
<211> LENGTH: 111
<212> TYPE: PRT
<213> ORGANISM: Felis catus

<400> SEQUENCE: 55

Gln Ala Val Leu Asn Gln Pro Ser Ser Val Ser Gly Ala Leu Gly Gln
1               5                   10                  15

Arg Val Thr Ile Ser Cys Ser Gly Ser Thr Met Asp Ile Asp Ile Phe
            20                  25                  30

Gly Val Ser Trp Tyr Gln Gln Ile Pro Gly Met Ala Pro Lys Thr Ile
        35                  40                  45

Ile Asp Ser Asp Gly Asp Arg Pro Ser Gly Val Pro Asp Arg Phe Ser
    50                  55                  60

Gly Ser Lys Ser Gly Ser Thr Gly Thr Leu Thr Ile Thr Gly Leu Gln
65                  70                  75                  80

Ala Glu Asp Glu Ala Asp Tyr Tyr Cys Gln Ser Gly Asp Ser Thr Leu
                85                  90                  95

Gly Ala Leu Ala Ile Phe Gly Gly Gly Thr His Val Thr Val Leu
            100                 105                 110
```

<210> SEQ ID NO 56
<211> LENGTH: 124
<212> TYPE: PRT
<213> ORGANISM: Felis catus

<400> SEQUENCE: 56

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Phe Ser Thr Tyr
            20                  25                  30

Gly Ile Asn Trp Val Arg Gln Ala Pro Gly Lys Gly Leu Gln Trp Val
        35                  40                  45

Ala Tyr Ile Ser Ser Gly Gly Ser Ser Thr Tyr Tyr Ala Asp Pro Val
    50                  55                  60

Lys Gly Arg Phe Thr Ile Ser Arg Asp Asn Ala Lys Asn Met Leu Tyr
65                  70                  75                  80

Leu Gln Met Asn Asn Leu Lys Thr Glu Asp Thr Ala Thr Tyr Tyr Cys
                85                  90                  95

Ala Gly Ser Arg Tyr Thr Tyr Ala Tyr Gly Gly Tyr Glu Phe His
            100                 105                 110

Phe Trp Gly Gln Gly Thr Leu Val Thr Val Ser Ser
        115                 120

<210> SEQ ID NO 57
<211> LENGTH: 333
<212> TYPE: DNA
<213> ORGANISM: Felis catus

<400> SEQUENCE: 57
caggcggtgc tgaaccagcc gagcagcgtg agcggcgcgc tgggccagcg cgtgaccatt      60
agctgcagcg gcagcaccat ggatattgat attttggcg tgagctggta tcagcagatt     120
ccgggcatgc cgccgaaaac cattattgat agcgatggcg atcgcccgag cggcgtgccg     180
gatcgcttta gcggcagcaa agcggcagc accggcaccc tgaccattac cggcctgcag     240
gcggaagatg aagcggatta ttattgccag agcggcgata gcaccctggg cgcgctggcg     300
atttttggcg gcggcaccca tgtgaccgtg ctg                                  333

<210> SEQ ID NO 58
<211> LENGTH: 372
<212> TYPE: DNA
<213> ORGANISM: Felis catus

<400> SEQUENCE: 58
gaggtacaac tggtggaatc tgggggagac ctggtgaagc tggggggatc cctgagactc      60
tcctgtgtgg cctctggatt caccttcagt acctatggca tcaactgggt ccgccaggct     120
ccagggaagg gctgcagtg gtcgcatac attagtagtg gtggaagtag cacatactat     180
gcagatcctg tgaagggccg gttcaccatc tccagagacg acgccaagaa catgctgtat     240
cttcagatga acagcctgag agccgaggac acggccatat attactgtgc gggtagtaga     300
tatacatatg catacggagg aggatatgag tttcacttct ggggccaggg aaccctggtc     360
accgtctcga gc                                                         372

<210> SEQ ID NO 59
<211> LENGTH: 201
<212> TYPE: PRT
<213> ORGANISM: Canis familiaris -continued

<400> SEQUENCE: 59

```
Gln His Ser Leu Asp Thr Ala Leu Arg Arg Ala Arg Ser Ala Pro Ala
1               5                   10                  15

Gly Ala Ile Ala Ala Arg Val Thr Gly Gln Thr Arg Asn Ile Thr Val
            20                  25                  30

Asp Pro Lys Leu Phe Lys Lys Arg Leu Arg Ser Pro Arg Val Leu
        35                  40                  45

Phe Ser Thr His Pro Pro Val Ala Asp Ala Gln Asp Leu Asp
    50                  55                  60

Leu Glu Ala Gly Ser Thr Ala Ser Val Asn Arg Thr His Arg Ser Lys
65                  70                  75                  80

Arg Ser Ser Pro His Pro Val Phe His Arg Gly Glu Phe Ser Val Cys
                85                  90                  95

Asp Ser Val Ser Val Trp Val Gly Asp Lys Thr Thr Ala Thr Asp Ile
            100                 105                 110

Lys Gly Lys Glu Val Met Val Leu Gly Glu Val Asn Ile Asn Asn Ser
        115                 120                 125

Val Phe Lys Gln Tyr Phe Phe Glu Thr Lys Cys Arg Asp Pro Thr Pro
130                 135                 140

Val Asp Ser Gly Cys Arg Gly Ile Asp Ser Lys His Trp Asn Ser Tyr
145                 150                 155                 160

Cys Thr Thr Thr His Thr Phe Val Lys Ala Leu Thr Met Asp Gly Lys
                165                 170                 175

Gln Ala Ala Trp Arg Phe Ile Arg Ile Asp Thr Ala Cys Val Cys Val
            180                 185                 190

Leu Ser Arg Lys Ala Gly Arg Arg Ala
        195                 200
```

<210> SEQ ID NO 60
<211> LENGTH: 106
<212> TYPE: PRT
<213> ORGANISM: Canis familiaris

<400> SEQUENCE: 60

```
Gly Gln Pro Lys Ala Ser Pro Ser Val Thr Leu Phe Pro Pro Ser Ser
1               5                   10                  15

Glu Glu Leu Gly Ala Asn Lys Ala Thr Leu Val Cys Leu Ile Ser Asp
            20                  25                  30

Phe Tyr Pro Ser Gly Val Thr Val Ala Trp Lys Ala Asp Gly Ser Pro
        35                  40                  45

Val Thr Gln Gly Val Glu Thr Thr Lys Pro Ser Lys Gln Ser Asn Asn
    50                  55                  60

Lys Tyr Ala Ala Ser Ser Tyr Leu Ser Leu Thr Pro Asp Lys Trp Lys
65                  70                  75                  80

Ser His Ser Ser Phe Ser Cys Leu Val Thr His Glu Gly Ser Thr Val
                85                  90                  95

Glu Lys Lys Val Ala Pro Ala Glu Cys Ser
            100                 105
```

<210> SEQ ID NO 61
<211> LENGTH: 318
<212> TYPE: DNA
<213> ORGANISM: Canis familiaris

<400> SEQUENCE: 61

```
ggacaaccga aggcctcccc ctcggtcaca ctcttcccgc cctcctctga ggagctcggc    60
gccaacaagg ccaccctggt gtgcctcatc agcgacttct accccagcgg cgtgacggtg   120
gcctggaagg cagacggcag ccccgtcacc cagggcgtgg agaccaccaa gccctccaag   180
cagagcaaca acaagtacgc ggccagcagc tacctgagcc tgacgcctga caagtggaaa   240
tctcacagca gcttcagctg cctggtcacg cacgagggga gcaccgtgga agaaggtg    300
gcccccgcag agtgctct                                                 318
```

<210> SEQ ID NO 62
<211> LENGTH: 335
<212> TYPE: PRT
<213> ORGANISM: Felis catus

<400> SEQUENCE: 62

```
Ala Ser Thr Thr Ala Pro Ser Val Phe Pro Leu Ala Pro Ser Cys Gly
 1               5                  10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300
```

```
Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335
```

<210> SEQ ID NO 63
<211> LENGTH: 1005
<212> TYPE: DNA
<213> ORGANISM: Felis catus

<400> SEQUENCE: 63

```
gcctccacca cggcccccatc ggtgttccca ctggccccca gctgcgggac cacatctggc    60
gccaccgtgg ccctggcctg cctggtgtta ggctacttcc ctgagccggt gaccgtgtcc   120
tggaactccg gcgccctgac cagcggtgtg cacaccttcc cggccgtcct gcaggcctcg   180
gggctgtact ctctcagcag catggtgaca gtgccctcca gcaggtggct cagtgacacc   240
ttcacctgca acgtggccca cccgcccagc aacaccaagg tggacaagac cgtgcgcaaa   300
acagaccacc caccgggacc caaaccctgc gactgtccca atgcccaccc cctgagatg    360
cttggaggac cgtccatctt catcttcccc ccaaaaccca aggacaccct ctcgatttcc   420
cggacgcccg aggtcacatg cttggtggtg gacttgggcc agatgactc cgatgtccag    480
atcacatggt ttgtggataa cacccaggtg tacacagcca agacgagtcc gcgtgaggag   540
cagttcaaca gcacctaccg tgtggtcagt gtcctcccca tcctacacca ggactggctc   600
aaggggaagg agttcaagtg caaggtcaac agcaaatccc tccctcccc catcgagagg   660
accatctcca aggccaaagg acagccccac gagcccagg tgtacgtcct gcctccagcc   720
caggaggagc tcagcaggaa caaagtcagt gtgacctgcc tgatcaaatc cttccacccg   780
cctgacattg ccgtcgagtg ggagatcacc ggacagccgg agccagagaa caactaccgg   840
acgaccccgc cccagctgga cagcgacggg acctacttcg tgtacagcaa gctctcggtg   900
gacaggtccc actggcagag gggaaacacc tacacctgct cggtgtcaca cgaagctctg   960
cacagccacc acacacagaa atccctcacc cagtctccgg gtaaa             1005
```

<210> SEQ ID NO 64
<211> LENGTH: 106
<212> TYPE: PRT
<213> ORGANISM: Felis catus

<400> SEQUENCE: 64

```
Gly Gln Pro Lys Ser Ala Pro Ser Val Thr Leu Phe Pro Pro Ser Asn
1               5                   10                  15

Glu Glu Leu Ser Ala Asn Lys Ala Thr Leu Val Cys Leu Ile Ser Asp
                20                  25                  30

Phe Tyr Pro Ser Gly Leu Thr Val Ala Trp Lys Ala Asp Gly Thr Pro
            35                  40                  45

Ile Thr Gln Gly Val Glu Thr Thr Lys Pro Ser Lys Gln Ser Asn Asn
        50                  55                  60

Lys Tyr Ala Ala Ser Ser Tyr Leu Ser Leu Ser Pro Asn Glu Trp Lys
65                  70                  75                  80

Ser Arg Ser Arg Phe Thr Cys Gln Val Thr His Glu Gly Ser Thr Val
                85                  90                  95

Glu Lys Asn Val Val Pro Ala Glu Cys Ser
            100                 105
```

<210> SEQ ID NO 65
<211> LENGTH: 318
<212> TYPE: DNA
<213> ORGANISM: Felis catus

<400> SEQUENCE: 65

```
ggccagccca agagcgctcc ctccgtgacc ctgttccccc caagcaacga ggaactgagc    60
gccaacaagg ccaccctggt gtgcctgatc agcgacttct accccagcgg cctgaccgtg   120
gcctggaagg ccgatggcac ccctatcacc cagggcgtgg aaaccaccaa gcccagcaag   180
cagagcaaca acaaatacgc cgccagcagc tacctgagcc tgagccccaa cgagtggaag   240
tcccggtccc ggttcacatg ccaggtgaca cacgagggca gcaccgtgga aaagaacgtg   300
gtgcccgccg agtgcagc                                                  318
```

<210> SEQ ID NO 66
<211> LENGTH: 240
<212> TYPE: PRT
<213> ORGANISM: Homo sapiens

<400> SEQUENCE: 66

```
Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Ala His Trp Thr Lys Leu Gln His Ser Leu Asp Thr Ala Leu
        35                  40                  45

Arg Arg Ala Arg Ser Ala Pro Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
130                 135                 140

Asp Lys Thr Thr Ala Thr Asp Ile Lys Gly Lys Glu Val Met Val Leu
145                 150                 155                 160

Gly Glu Val Ser Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Cys Thr Thr His Thr Phe Val Lys
        195                 200                 205

Ala Leu Thr Met Asp Gly Lys Gln Ala Ala Trp Arg Phe Ile Arg Ile
    210                 215                 220

Asp Thr Ala Cys Met Cys Val Leu Ser Arg Lys Ala Val Arg Arg Ala
225                 230                 235                 240
```

<210> SEQ ID NO 67
<211> LENGTH: 125
<212> TYPE: PRT
<213> ORGANISM: Homo sapiens

<400> SEQUENCE: 67

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Gly Met Ser Trp Val Arg Gln Ala Pro Gly Lys Gly Leu Glu Trp Val
        35                  40                  45

Ser Val Ile Asn Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Val Gly Gly Trp Glu Gln Leu Val Gly Pro His Phe
            100                 105                 110

Asp Tyr Trp Gly Gln Gly Thr Leu Val Ile Val Ser Ser
        115                 120                 125

<210> SEQ ID NO 68
<211> LENGTH: 375
<212> TYPE: DNA
<213> ORGANISM: Homo sapiens

<400> SEQUENCE: 68
gaagtgcagc tggtggaaag cggcggcggc ctggtgcagc cgggcggcag cctgcgcctg      60
agctgcgcgg cgagcggctt tacctttagc agccatggca tgagctgggt gcgccaggcg     120
ccgggcaaag gcctggaatg gtgagcgtg attaacagcg gcggcagcag cacctattat      180
gcggatagcg tgaaaggccg ctttaccatt agccgcgata acagcaaaaa cacccctgtat    240
ctgcagatga acagcctgcg cgcggaagat accgcggtgt attattgcgc gaaagaaagc     300
gtgggcggct gggaacagct ggtgggcccg catttgatt attggggcca gggcacccctg     360
gtgattgtct cgagc                                                      375

<210> SEQ ID NO 69
<211> LENGTH: 125
<212> TYPE: PRT
<213> ORGANISM: Homo sapiens

<400> SEQUENCE: 69

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ser Val Ile Asn Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Val Gly Gly Trp Glu Gln Leu Val Gly Pro His Phe
            100                 105                 110

Asp Tyr Trp Gly Gln Gly Thr Leu Val Ile Val Ser Ser
            115                 120                 125

<210> SEQ ID NO 70
<211> LENGTH: 375
<212> TYPE: DNA
<213> ORGANISM: Homo sapiens

<400> SEQUENCE: 70
caggtgcagc tggtggaaag cggcggcggc gtggtgcagc cgggcggcag cctgcgcctg      60
agctgcgcgg cgagcggctt tacctttagc agccatggca tgcattgggt gcgccaggcg     120
ccgggcaaag gcctggaatg ggtgagcgtg attaacagcg cggcagcag cacctattat      180 gcggatagcg tgaaaggccg ctttaccatt agccgcgata cagcaaaaa caccctgtat      240 ctgcagatga acagcctgcg cgcggaagat accgcggtgt attattgcgc gaaagaaagc     300
gtgggcggct gggaacagct ggtgggcccg cattttgatt attggggcca gggcaccctg     360
gtgattgtct cgagc                                                      375

<210> SEQ ID NO 71
<211> LENGTH: 110
<212> TYPE: PRT
<213> ORGANISM: Homo sapiens

<400> SEQUENCE: 71

Gln Ser Val Leu Thr Gln Pro Pro Ser Val Ser Gly Ala Pro Gly Gln
1               5                   10                  15

Arg Val Thr Ile Ser Cys Thr Gly Ser Thr Asn Asn Ile Gly Ile Leu
            20                  25                  30

Gly Val His Trp Tyr Gln Gln Leu Pro Gly Thr Ala Pro Lys Leu Leu
        35                  40                  45

Ile Tyr Gly Asn Gly Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Phe Asp Thr Thr Leu
                85                  90                  95

Gly Ala His Val Phe Gly Gly Gly Thr His Leu Thr Val Leu
            100                 105                 110

<210> SEQ ID NO 72
<211> LENGTH: 330
<212> TYPE: DNA
<213> ORGANISM: Homo sapiens

<400> SEQUENCE: 72
cagagcgtgc tgacccagcc gccgagcgtg agcggcgcgc cgggccagcg cgtgaccatt      60
agctgcaccg gcagcaccaa caacattggc attctgggcg tgcattggta tcagcagctg     120
ccgggcaccg cgccgaaact gctgatttat ggcaacggca accgcccgag cggcgtgccg     180
gatcgcttta gcggcagcaa aagcggcacc agcgcgagcc tggcgattac cggcctgcag     240
gcggaagatg aagcggatta ttattgccag agctttgata ccaccctggg cgcgcatgtg     300
tttggcggcg gcacccatct gaccgtgctg                                      330

<210> SEQ ID NO 73
<211> LENGTH: 110
<212> TYPE: PRT

<213> ORGANISM: Homo sapiens

<400> SEQUENCE: 73

Gln Ser Val Leu Thr Gln Pro Thr Ser Val Ser Gly Ala Pro Gly Gln
1               5                   10                  15

Arg Val Thr Ile Ser Cys Thr Gly Ser Thr Asn Asn Ile Gly Ile Leu
            20                  25                  30

Gly Val His Trp Tyr Gln Gln Leu Pro Gly Thr Ala Pro Lys Leu Leu
        35                  40                  45

Ile Tyr Gly Asn Gly Asn Arg Pro Ser Gly Val Pro Asp Arg Phe Ser
    50                  55                  60

Gly Ala Asp Ser Gly Asp Ser Val Ser Leu Ala Ile Thr Gly Leu Gln
65                  70                  75                  80

Ala Glu Asp Glu Ala Asp Tyr Tyr Cys Gln Ser Phe Asp Thr Thr Leu
                85                  90                  95

Gly Ala His Val Phe Gly Gly Gly Thr His Leu Thr Val Leu
            100                 105                 110

<210> SEQ ID NO 74
<211> LENGTH: 330
<212> TYPE: DNA
<213> ORGANISM: Homo sapiens

<400> SEQUENCE: 74
cagagcgtgc tgacccagcc gaccagcgtg agcggcgcgc cgggccagcg cgtgaccatt      60
agctgcaccg gcagcaccaa caacattggc attctgggcg tgcattggta tcagcagctg     120
ccgggcaccg cgccgaaact gctgatttat ggcaacggca accgcccgag cggcgtgccg     180 gatcgctttta gcggcgcgga tagcggcgat agcgtgagcc tggcgattac cggcctgcag     240
gcggaagatg aagcggatta ttattgccag agctttgata ccaccctggg cgcgcatgtg     300
tttggcggcg gcacccatct gaccgtgctg                                      330

<210> SEQ ID NO 75
<211> LENGTH: 124
<212> TYPE: PRT
<213> ORGANISM: Homo sapiens

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Asn Trp Val Arg Gln Ala Pro Gly Lys Gly Leu Glu Trp Val
        35                  40                  45

Ser Tyr Ile Ser Ser Gly Gly Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Ser Arg Tyr Thr Tyr Ala Tyr Gly Gly Gly Tyr Glu Phe His
            100                 105                 110

Phe Trp Gly Gln Gly Thr Leu Val Thr Val Ser Ser
        115                 120

<210> SEQ ID NO 76

```
<211> LENGTH: 372
<212> TYPE: DNA
<213> ORGANISM: Homo sapiens

<400> SEQUENCE: 76
gaagtgcagc tggtggaaag cggcggcggc ctggtgcagc cgggcggcag cctgcgcctg      60
agctgcgcgg cgagcggctt tacctttagc acctatggca tgaactgggt gcgccaggcg     120
ccgggcaaag gcctggaatg ggtgagctat attagcagcg gcggcagcag catttattat     180
gcggatagcg tgaaaggccg ctttaccatt agccgcgata cgcgaaaaa cagcctgtat      240 ctgcagatga acagcctgcg cgcggaagat accgcggtgt attattgcgc gggcagccgc     300
tataccctat gcgtatggcgg cggctatgaa tttcattttt ggggccaggg caccctggtg    360
attgtctcga gc                                                          372

<210> SEQ ID NO 77
<211> LENGTH: 124
<212> TYPE: PRT
<213> ORGANISM: Homo sapiens

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Asn Trp Val Arg Gln Ala Pro Gly Lys Gly Leu Gln Trp Val
        35                  40                  45

Ser Tyr Ile Ser Ser Gly Gly Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Gly Ser Arg Tyr Thr Tyr Ala Tyr Gly Gly Tyr Glu Phe His
            100                 105                 110

Phe Trp Gly Gln Gly Thr Leu Val Thr Val Ser Ser
        115                 120

<210> SEQ ID NO 78
<211> LENGTH: 372
<212> TYPE: DNA
<213> ORGANISM: Homo sapiens

<400> SEQUENCE: 78
gaagtgcagc tggtggaaag cggcggcggc ctggtgcagc cgggcggcag cctgcgcctg      60
agctgcgcgg cgagcggctt tacctttagc acctatggca tgaactgggt gcgccaggcg     120
ccgggcaaag gcctgcagtg ggtgagctat attagcagcg gcggcagcag catttattat     180
gcggatagcg tgaaaggccg ctttaccatt agccgcgata cgcgaaaaa cagcctgtat      240 ctgcagatga acagcctgcg cgcggaagat accgcggtgt attattgcgc gggcagccgc     300
tataccctat gcgtatggcgg cggctatgaa tttcattttt ggggccaggg caccctggtg    360
attgtctcga gc                                                          372

<210> SEQ ID NO 79
<211> LENGTH: 124
<212> TYPE: PRT
<213> ORGANISM: Homo sapiens
```

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Ile Asn Trp Val Arg Gln Ala Pro Gly Lys Gly Leu Glu Trp Val
        35                  40                  45

Ser Tyr Ile Ser Ser Gly Gly Ser Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Ser Arg Tyr Thr Tyr Ala Tyr Gly Gly Tyr Glu Phe His
            100                 105                 110

Phe Trp Gly Gln Gly Thr Leu Val Thr Val Ser Ser
        115                 120

<210> SEQ ID NO 80
<211> LENGTH: 372
<212> TYPE: DNA
<213> ORGANISM: Homo sapiens

<400> SEQUENCE: 80

```
gaagtgcagc tggtggaaag cggcggcggc ctggtgaaac cgggcggcag cctgcgcctg     60
agctgcgcgg cgagcggctt tacctttagc acctatggca ttaactgggt gcgccaggcg    120
ccgggcaaag gcctggaatg ggtgagctat attagcagcg gcggcagcag cacctattat    180
gcggatagcg tgaaaggccg ctttaccatt agccgcgata cgcgaaaaaa cagcctgtat    240
ctgcagatga acagcctgcg cgcggaagat accgcggtgt attattgcgc gggcagccgc    300
tataccctatg cgtatggcgg cggctatgaa tttcattttt ggggccaggg caccctggtg    360
attgtctcga gc                                                        372
```

<210> SEQ ID NO 81
<211> LENGTH: 124
<212> TYPE: PRT
<213> ORGANISM: Homo sapiens

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Ile Asn Trp Val Arg Gln Ala Pro Gly Lys Gly Leu Gln Trp Val
        35                  40                  45

Ser Tyr Ile Ser Ser Gly Gly Ser Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Ser Arg Tyr Thr Tyr Ala Tyr Gly Gly Tyr Glu Phe His
            100                 105                 110

Phe Trp Gly Gln Gly Thr Leu Val Thr Val Ser Ser
        115                 120

<210> SEQ ID NO 82
<211> LENGTH: 372
<212> TYPE: DNA
<213> ORGANISM: Homo sapiens

<400> SEQUENCE: 82
gaagtgcagc tggtggaaag cggcggcggc ctggtgaaac cgggcggcag cctgcgcctg      60
agctgcgcgg cgagcggctt tacctttagc acctatggca ttaactgggt gcgccaggcg     120
ccgggcaaag gcctgcagtg ggtgagctat attagcagcg gcggcagcag cacctattat     180
gcggatagcg tgaaaggccg ctttaccatt agccgcgata cgcgaaaaaa cagcctgtat     240
ctgcagatga acagcctgcg cgcggaagat accgcggtgt attattgcgc gggcagccgc     300 tataccctatg cgtatggcgg cggctatgaa tttcattttt ggggccaggg caccctggtg     360
attgtctcga gc                                                          372

<210> SEQ ID NO 83
<211> LENGTH: 110
<212> TYPE: PRT
<213> ORGANISM: Homo sapiens

<400> SEQUENCE: 83

Gln Ser Val Leu Thr Gln Pro Ala Ser Ala Ser Gly Thr Pro Gly Gln
1               5                   10                  15

Arg Val Thr Ile Ser Cys Ser Gly Ser Thr Met Asp Ile Asp Ile Phe
            20                  25                  30

Gly Val Asn Trp Tyr Gln Gln Leu Pro Gly Thr Ala Pro Lys Leu Leu
        35                  40                  45

Ile Tyr Ser Asp Gly Asp Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr His Cys Gln Ser Gly Asp Ser Thr Leu
                85                  90                  95

Gly Ala Leu Ala Ile Phe Gly Gly Gly Thr His Val Thr Val
            100                 105                 110

<210> SEQ ID NO 84
<211> LENGTH: 333
<212> TYPE: DNA
<213> ORGANISM: Homo sapiens

<400> SEQUENCE: 84
cagagcgtgc tgacccagcc ggcgagcgcg agcggcaccc cgggccagcg cgtgaccatt      60
agctgcagcg gcagcaccat ggatattgat atttttggcg tgaactggta tcagcagctg     120
ccgggcaccg cgccgaaact gctgatttat agcgatggcg atcgcccgag cggcgtgccg     180
gatcgcttta gcggcagcaa aagcggcacc agcgcgagcc tggcgattag cggcctgcag     240
agcgaagatg aagcggatta tcattgccag agcggcgata gcaccctggg cgcgctggcg     300 attttttggcg gcggcacccca tgtgaccgtg ctg                                 333

<210> SEQ ID NO 85
<211> LENGTH: 111
<212> TYPE: PRT

<213> ORGANISM: Homo sapiens

<400> SEQUENCE: 85

Gln Ser Val Leu Thr Gln Pro Pro Ser Ala Ser Gly Thr Leu Gly Gln
1               5                   10                  15

Arg Val Thr Ile Ser Cys Ser Gly Ser Thr Met Asp Ile Asp Ile Phe
            20                  25                  30

Gly Val Asn Trp Tyr Gln Gln Leu Pro Gly Thr Ala Pro Lys Leu Leu
        35                  40                  45

Ile Tyr Ser Asp Gly Asp Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr His Cys Gln Ser Gly Asp Ser Thr Leu
                85                  90                  95

Gly Ala Leu Ala Ile Phe Gly Gly Gly Thr His Val Thr Val Leu
                100                 105                 110

<210> SEQ ID NO 86
<211> LENGTH: 333
<212> TYPE: DNA
<213> ORGANISM: Homo sapiens

<400> SEQUENCE: 86
cagagcgtgc tgacccagcc gccgagcgcg agcggcaccc tgggccagcg cgtgaccatt      60
agctgcagcg gcagcaccat ggatattgat atttttggcg tgaactggta tcagcagctg     120
ccgggcaccg cgccgaaact gctgatttat agcgatggcg atcgcccgag cggcgtgccg     180
gatcgcttta gcggcagcaa aagcggcacc agcgcgagcc tggcgattag cggcctgcag     240
agcgaagatg aagcggatta tcattgccag agcggcgata gcaccctggg cgcgctggcg     300
atttttggcg gcggcaccca tgtgaccgtg ctg                                  333

<210> SEQ ID NO 87
<211> LENGTH: 111
<212> TYPE: PRT
<213> ORGANISM: Homo sapiens

<400> SEQUENCE: 87

Gln Ser Val Val Thr Gln Pro Ala Ser Val Ser Gly Ala Pro Gly Gln
1               5                   10                  15

Arg Val Thr Ile Ser Cys Thr Gly Ser Thr Met Asp Ile Asp Ile Phe
            20                  25                  30

Gly Val Ser Trp Tyr Gln Gln Leu Pro Gly Thr Ala Pro Lys Leu Leu
        35                  40                  45

Ile Tyr Gly Asp Gly Asp Arg Pro Ser Gly Val Pro Asp Arg Phe Ser
    50                  55                  60

Gly Ser Lys Ser Gly Ala Ser Ala Ser Leu Ala Ile Thr Gly Leu Gln
65                  70                  75                  80

Ala Glu Asp Glu Ala Asp Tyr His Cys Gln Ser Gly Asp Ser Thr Leu
                85                  90                  95

Gly Ala Leu Ala Ile Phe Gly Gly Gly Thr His Val Thr Val Leu
                100                 105                 110

<210> SEQ ID NO 88
<211> LENGTH: 333
<212> TYPE: DNA
<213> ORGANISM: Homo sapiens

<400> SEQUENCE: 88

```
cagagcgtgg tgacccagcc ggcgagcgtg agcggcgcgc cgggccagcg cgtgaccatt        60
agctgcaccg gcagcaccat ggatattgat attttggcg tgagctggta tcagcagctg       120
ccgggcaccg cgccgaaact gctgatttat ggcgatggcg atcgcccgag cggcgtgccg       180
gatcgcttta gcggcagcaa agcggcgcg agcgcgagcc tggcgattac cggcctgcag       240
gcggaagatg aagcggatta tcattgccag agcggcgata gcaccctggg cgcgctggcg       300 attttggcg gcggcaccca tgtgaccgtg ctg                                    333
```

<210> SEQ ID NO 89
<211> LENGTH: 111
<212> TYPE: PRT
<213> ORGANISM: Homo sapiens

<400> SEQUENCE: 89

Gln Ser Val Val Thr Gln Pro Pro Ser Val Gly Ala Leu Gly Gln
1               5                   10                  15

Arg Val Thr Ile Ser Cys Thr Gly Ser Thr Met Asp Ile Asp Ile Phe
            20                  25                  30

Gly Val Ser Trp Tyr Gln Gln Leu Pro Gly Thr Ala Pro Lys Leu Leu
        35                  40                  45

Ile Tyr Gly Asp Gly Asp Arg Pro Ser Gly Val Pro Asp Arg Phe Ser
    50                  55                  60

Gly Ser Lys Ser Gly Ala Ser Ala Ser Leu Ala Ile Thr Gly Leu Gln
65                  70                  75                  80

Ala Glu Asp Glu Ala Asp Tyr His Cys Gln Ser Gly Asp Ser Thr Leu
                85                  90                  95

Gly Ala Leu Ala Ile Phe Gly Gly Gly Thr His Val Thr Val Leu
            100                 105                 110

<210> SEQ ID NO 90
<211> LENGTH: 333
<212> TYPE: DNA
<213> ORGANISM: Homo sapiens

<400> SEQUENCE: 90

```
cagagcgtgg tgacccagcc gccgagcgtg agcggcgcgc tgggccagcg cgtgaccatt        60
agctgcaccg gcagcaccat ggatattgat attttggcg tgagctggta tcagcagctg       120
ccgggcaccg cgccgaaact gctgatttat ggcgatggcg atcgcccgag cggcgtgccg       180
gatcgcttta gcggcagcaa agcggcgcg agcgcgagcc tggcgattac cggcctgcag       240
gcggaagatg aagcggatta tcattgccag agcggcgata gcaccctggg cgcgctggcg       300 attttggcg gcggcaccca tgtgaccgtg ctg                                    333
```

<210> SEQ ID NO 91
<211> LENGTH: 111
<212> TYPE: PRT
<213> ORGANISM: Canis familiaris

<400> SEQUENCE: 91

Gln Ser Val Val Thr Gln Pro Pro Ser Val Ser Gly Ala Pro Gly Gln
1               5                   10                  15

Arg Val Thr Ile Ser Cys Thr Gly Ser Thr Met Asp Ile Asp Ile Phe
            20                  25                  30

```
Gly Val Ser Trp Tyr Gln Gln Leu Pro Gly Thr Ala Pro Lys Leu Leu
        35                  40                  45

Ile Tyr Gly Asp Gly Asp Arg Pro Ser Gly Val Pro Asp Arg Phe Ser
    50                  55                  60

Gly Ser Lys Ser Gly Ala Ser Ala Ser Leu Ala Ile Thr Gly Leu Gln
65                  70                  75                  80

Ala Glu Asp Glu Ala Asp Tyr His Cys Gln Ser Gly Asp Ser Thr Leu
                85                  90                  95

Gly Ala Leu Ala Ile Phe Gly Gly Gly Thr His Val Thr Val Leu
                100                 105                 110

<210> SEQ ID NO 92
<211> LENGTH: 333
<212> TYPE: DNA
<213> ORGANISM: Canis familiaris

<400> SEQUENCE: 92
cagagcgtgg tgacccagcc gccgagcgtg agcggcgcgc cgggccagcg cgtgaccatt      60
agctgcaccg gcagcaccat ggatattgat attttggcg tgagctggta tcagcagctg     120
ccgggcaccg cgccgaaact gctgatttat ggcgatggca tcgcccgag cggcgtgccg     180 gatcgcttta gcggcagcaa aagcggcgcg agcgcgagcc tggcgattac cggcctgcag     240
gcggaagatg aagcggatta tcattgccag agcggcgata gcaccctggg cgcgctggcg     300 attttggcg gcggcaccca tgtgaccgtg ctg                                   333
```

NUCLEIC ACIDS ENCODING A CANINE ANTIBODY WHICH BINDS NERVE GROWTH FACTOR AND VECTORS AND HOST CELLS THEREOF

This application is a continuation of U.S. application Ser. No. 16/251,293, filed Jan. 18, 2019, which claims priority to the U.S. Provisional Application No. 62/641,538, filed Mar. 12, 2018, the contents of which are incorporated by reference in their entirety.

FIELD OF THE INVENTION

The present invention relates to the field of immunology. More specifically, the present invention relates to anti-NGF antigen binding proteins that specifically bind to NGF that have been modified to become non-immunogenic in species of interest. The invention further concerns use of such antigen binding proteins in the treatment and/or prevention of NGF related disorders, particularly pain.

BACKGROUND OF THE INVENTION

Nerve growth factor (NGF) was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne, et al., Nature 368:246-249 (1994) and Crowley, et al., Cell 76: 1001-101 I (1994)). NGF upregulates expression of neuropeptides in sensory neurons (Lindsay, et al, Nature 337:362-364 (1989)), and its activity is mediated through two different membrane-bound receptors, the TrkA tyrosine kinase receptor and the p75 common neurotrophin receptor (sometimes termed "high affinity" and "low affinity" NGF receptors, respectively) which is structurally related to other members of the tumor necrosis factor receptor family (Chao, et al., Science 232: 518-521 (1986)).

In addition to its effects in the nervous system, NGF has been increasingly implicated in processes outside of the nervous system. For example, NGF has been shown to enhance vascular permeability (Otten, et al., Eur J Pharmacol. 106: 199-201 (1984)), enhance T- and B-cell immune responses (Otten, et al., Proc. Nat. Acad. Sci. USA 86:10059-10063 (1989)), induce lymphocyte differentiation and mast cell proliferation and cause the release of soluble biological signals from mast cells (Matsuda, et al., Proc. Nat. Acad. Sci. USA 85:6508-6512 (1988); Pearce, et al., J. Physiol. 372:379-393 (1986); Bischoff, et al., Blood 79:2662-2669 (1992); Horigome, et al., J. Biol. Chem. 268:14881-14887 (1993)).

NGF is produced by several cell types including mast cells (Leon, et al., Proc. Natl. Acad. Sci. USA 91:3739-3743 (1994)), B-lymphocytes (Torcia, et al., Cell 85:345-356 (1996), keratinocytes (Di Marco, et al., J. Biol. Chem. 268:22838-22846)), smooth muscle cells (Ueyama, et al., J. Hypertens. 11: 1061-1065 (1993)), fibroblasts (Lindholm, et al., Eur. J. Neurosci. 2:795-801 (1990)), bronchial epithelial cells (Kassel, et al., Clin, Exp. Allergy 31:1432-40 (2001)), renal mesangial cells (Steiner, et al., Am. J. Physiol. 261: F792-798 (1991)) and skeletal muscle myotubes (Schwartz, et al., J Photochem. Photobiol. B66: 195-200 (2002)). NGF receptors have been found on a variety of cell types outside of the nervous system. For example, TrkA has been found on human monocytes, T- and B-lymphocytes and mast cells.

An association between increased NGF levels and a variety of inflammatory conditions has been observed in human patients as well as in several animal models. These include systemic lupus erythematosus (Bracci-Laudiero, et al., Neuroreport 4:563-565 (1993)), multiple sclerosis (BracciLaudiero, et al, Neurosci. Lett. 147:9-12 (1992)), psoriasis (Raychaudhuri, et al., Acta Derm. I'enereol. 78:84-86 (1998)), arthritis (Falcim, et al., Ann. Rheum. Dis. 55:745-748 (1996)), interstitial cystitis (Okragly, et al., J. Urology 161: 438-441 (1999)) and asthma (Braun, et al., Eur. J Immunol. 28:3240-3251 (1998)). A consistently elevated level of NGF in peripheral tissues is associated with hyperalgesia and inflammation and has been observed in several forms of arthritis. The synovium of patients affected by rheumatoid arthritis expresses high levels of NGF while in non-inflamed synovium NGF has been reported to be undetectable (Aloe, et al., Arch. Rheum. 35:351-355 (1992)). Similar results were seen in rats with experimentally induced rheumatoid arthritis (Aloe, et al., Clin. Exp. Rheumatol. 10:203-204 (1992)). Elevated levels of NGF have been reported in transgenic arthritic mice along with an increase in the number of mast cells (Aloe, et al., Int. J. Tissue Reactions-Exp. Clin. Aspects 15:139-143 (1993)).

Osteoarthritis (OA) is one of the most common chronic musculoskeletal diseases in dogs, affecting 20% of the canine population over one year of age. The development of OA is mainly secondary to trauma, joint instability, and diseases such as hip dysplasia. Osteoarthritis is a disease condition of the entire joint, and both inflammatory and degenerative changes of all articular structures result in disability and clinical signs of lameness and pain. Pain is the most important clinical manifestation of canine OA and it is the result of a complex interplay between structural joint changes, biochemical and molecular alterations, as well as peripheral and central pain-processing mechanisms. Within this network, the activation and sensitization of peripheral nociceptors by inflammatory and hyperalgesic mediators (e.g. cytokines, prostaglandins and neuromediators) is one of the main peripheral mechanisms responsible for the joint pain. Treatment of canine pain by a non-pharmaceutical medicament that would provide relief for longer periods of time than would classic pain treatment in canines is clearly an unmet need.

Within the United States alone approximately 14.5 million dogs suffer from OA (2010 market research). Non-steroidal anti-inflammatory drugs (NSAIDs) are the most common drug category prescribed by veterinarians, but are limited by their efficacy and tolerability. Market research indicates that approximately 9 million dogs are treated with NSAIDs within the US. Corticosteroids are used rarely and typically for a short period of time and as a last resort. There clearly remains an unmet need for a convenient, safe product that effectively treats dogs with OA.

In felines, OA is a pathological change of a diarthrodial synovial articulation, characterized by the deterioration of articular cartilage, osteophyte formation, bone remodeling, soft tissue changes and a low-grade non-purulent inflammation. Even though radiographic features of feline OA have been well described, clinical signs of disease are poorly documented and can go undiagnosed. The difficulty in assessing lameness in cats results for their small size and natural agility which allows them to compensate. It is believed, however, that clinical signs of feline OA include weight loss, anorexia, depression, abnormal elimination habits, poor grooming, aggressive behavior and a gradual reduction in the ability to jump to overt lameness. Based on misdiagnosis feline OA remains generally untreated and is an unmet veterinary medicine need.

SUMMARY OF THE INVENTION

The invention provides a novel anti-NGF antigen binding protein (antibody, antibody fragment, antigen binding fragment, antigen binding portion, antagonist antibody, etc. as defined and used interchangeably herein), and polynucleotides encoding the same. The invention further provides methods of making and using of said antigen binding proteins and/or nucleotides in the treatment and/or prevention of NGF related disorders, particularly pain, in a subject. The invention further provides pharmaceutical compositions and uses for treatment of NGF related disorders, particularly pain, in a subject.

In one aspect the present invention provides a recombinant antigen binding protein that specifically binds to Nerve Growth Factor (NGF) comprising a variable light chain (VL) comprising a Complementary Determining Region 1 (CDR1) comprising amino acid sequences having at least 90% sequence identity to SEQ ID. NO. 1 or SEQ ID NO. 21; a Complementary Determining Region 1 (CDR2) comprising amino acid sequences having at least 90% sequence identity to SEQ ID. NO. 2 or SEQ ID NO. 22; a Complementary Determining Region 1 (CDR3) comprising amino acid sequences having at least 90% sequence identity to SEQ ID. NO. 3 or SEQ ID NO. 23; and a variable heavy chain (VH) comprising: a Complementary Determining Region 1 (CDR1) comprising amino acid sequences having at least 90% sequence identity to SEQ ID. NO. 4 or SEQ ID NO. 24; a Complementary Determining Region 1 (CDR2) comprising amino acid sequences having at least 90% sequence identity to SEQ ID. NO. 5 or SEQ ID NO. 25; and a Complementary Determining Region 1 (CDR3) comprising amino acid sequences having at least 90% sequence identity to SEQ ID. NO. 6 or SEQ ID NO. 26; and any variants thereof having one or more conservative amino acid substitutions in at least one of CDR1, CDR2 or CDR3 within any of the variable light or variable heavy chain regions of said antigen binding protein.

In one embodiment the present invention provides that the antigen binding protein comprises a light chain variable region (VL) comprising a Complimentary Determining Region 1 (CDR1) comprising an amino acid sequence having at least about 90% sequence identity to the amino acid sequence comprising SEQ ID NO. 1; a Complimentary Determining Region 2 (CDR2) comprising an amino acid sequence having at least about 90% sequence identity to the amino acid sequence comprising SEQ ID NO. 2; a Complimentary Determining Region 3 (CDR3) comprising an amino acid sequence having at least about 90% sequence identity to the amino acid sequence comprising SEQ ID NO. 3; and a heavy chain variable region (VH) comprising: a Complimentary Determining Region 1 (CDR1) comprising an amino acid sequence having at least about 90% sequence identity to the amino acid sequence comprising SEQ ID NO. 4; a Complimentary Determining Region 2 (CDR2) comprising an amino acid sequence having at least about 90% sequence identity to the amino acid sequence comprising SEQ ID NO. 5; a Complimentary Determining Region 3 (CDR3) comprising an amino acid sequence having at least about 90% sequence identity to the amino acid sequence comprising SEQ ID NO. 6 and any variants thereof having one or more conservative amino acid substitutions in at least one of CDR1, CDR2 or CDR3 within any of the variable light or variable heavy chain regions of said antigen binding protein.

In one embodiment the present invention provides that the antigen binding protein of invention comprises a light chain variable region (VL) comprising a Complimentary Determining Region 1 (CDR1) comprising an amino acid sequence having at least about 90% sequence identity to the amino acid sequence comprising SEQ ID NO. 21; a Complimentary Determining Region 2 (CDR2) comprising an amino acid sequence having at least about 90% sequence identity to the amino acid sequence comprising SEQ ID NO. 22; a Complimentary Determining Region 3 (CDR3) comprising an amino acid sequence having at least about 90% sequence identity to the amino acid sequence comprising SEQ ID NO. 23 and a heavy chain variable region (VH) comprising: a Complimentary Determining Region 1 (CDR1) comprising an amino acid sequence having at least about 90% sequence identity to the amino acid sequence comprising SEQ ID NO. 24; a Complimentary Determining Region 2 (CDR2) comprising an amino acid sequence having at least about 90% sequence identity to the amino acid sequence comprising SEQ ID NO. 25; a Complimentary Determining Region 3 (CDR3) comprising an amino acid sequence having at least about 90% sequence identity to the amino acid sequence comprising SEQ ID NO. 26 and any variants thereof having one or more conservative amino acid substitutions in at least one of CDR1, CDR2 or CDR3 within any of the variable light or variable heavy chain regions of said antigen binding protein.

In one aspect the present invention provides a recombinant antigen binding protein that specifically binds to Nerve Growth Factor (NGF) comprising a variable light chain comprising an amino acid sequence having at least 90% sequence identity to the amino acid sequences selected from the group consisting of: SEQ ID NO. 7; SEQ ID NO. 9; SEQ ID NO. 27; SEQ ID NO. 29; SEQ ID NO. 55; SEQ ID NO. 71; SEQ ID NO. 73; SEQ ID NO. 83; SEQ ID NO. 85; SEQ ID NO. 87; SEQ ID NO. 89; and SEQ ID NO. 91; and a variable heavy chain comprising an amino acid sequence having at least 90% sequence identity to the amino acid sequences selected from the group consisting of: SEQ ID NO. 8; SEQ ID NO. 10; SEQ ID NO. 28; SEQ ID NO. 30; SEQ ID NO. 56; SEQ ID NO. 67; SEQ ID NO. 69; SEQ ID NO. 75; SEQ ID NO. 77; SEQ ID NO. 79 and SEQ ID NO. 81; and any variants thereof having one or more conservative amino acid substitutions within any of the variable light or variable heavy chain regions of said antigen binding protein.

In one embodiment the invention provides that the recombinant antigen binding protein of the invention comprises the variable light chain comprising an amino acid sequence having at least 90% sequence identity to SEQ ID NO. 7 and the variable heavy chain comprising an amino acid sequence having at least 90% sequence identity to SEQ ID NO. 8, and any variants thereof having one or more conservative amino acid substitutions within any of the variable light or variable heavy chain regions of said antigen binding protein. In one embodiment, the invention provides an antigen binding protein wherein the variable light chain comprises an amino acid sequence having at least 90% sequence identity to SEQ ID NO. 27 and the variable heavy chain comprising an amino acid sequence having at least 90% sequence identity to SEQ ID NO. 28 and any variants thereof having one or more conservative amino acid substitutions within any of the variable light or variable heavy chain regions of said antigen binding protein.

In one embodiment the invention provides that the recombinant antigen binding protein of the invention comprises the variable light chain comprising an amino acid sequence having at least 90% sequence identity to SEQ ID NO. 9 and the variable heavy chain comprising an amino acid sequence having at least 90% sequence identity to SEQ ID NO. 10, and any variants thereof having one or more conservative amino acid substitutions within any of the variable light or variable heavy chain regions of said antigen binding protein. In one embodiment the invention provides that the recombinant antigen binding protein of the invention comprises the variable light chain comprising an amino acid sequence having at least 90% sequence identity to SEQ ID NO. 29 and the variable heavy chain comprising an amino acid sequence having at least 90% sequence identity to SEQ ID NO. 30, and any variants thereof having one or more conservative amino acid substitutions within any of the variable light or variable heavy chain regions of said antigen binding protein.

In one embodiment the invention provides that the recombinant antigen binding protein of the invention comprises the variable light chain comprising an amino acid sequence having at least 90% sequence identity to SEQ ID NO. 55 and the variable heavy chain comprising an amino acid sequence having at least 90% sequence identity to SEQ ID NO. 56, and any variants thereof having one or more conservative amino acid substitutions within any of the variable light or variable heavy chain regions of said antigen binding protein.

In one embodiment the invention provides that the recombinant antigen binding protein of the invention comprises the variable light chain comprising an amino acid sequence having at least 90% sequence identity to SEQ ID NO. 91 and the variable heavy chain comprising an amino acid sequence having at least 90% sequence identity to SEQ ID NO. 79, and any variants thereof having one or more conservative amino acid substitutions within any of the variable light or variable heavy chain regions of said antigen binding protein. In one embodiment the invention provides that the recombinant antigen binding protein of the invention comprises the variable light chain comprising an amino acid sequence having at least 90% sequence identity to SEQ ID NO. 87 and the variable heavy chain comprising an amino acid sequence having at least 90% sequence identity to SEQ ID NO. 79, and any variants thereof having one or more conservative amino acid substitutions within any of the variable light or variable heavy chain regions of said antigen binding protein. In one embodiment the invention provides that the recombinant antigen binding protein of the invention comprises the variable light chain comprising an amino acid sequence having at least 90% sequence identity to SEQ ID NO. 91 and the variable heavy chain comprising an amino acid sequence having at least 90% sequence identity to SEQ ID NO. 75, and any variants thereof having one or more conservative amino acid substitutions within any of the variable light or variable heavy chain regions of said antigen binding protein. In one embodiment the invention provides that the recombinant antigen binding protein of the invention comprises the variable light chain comprising an amino acid sequence having at least 90% sequence identity to SEQ ID NO. 87 and the variable heavy chain comprising an amino acid sequence having at least 90% sequence identity to SEQ ID NO. 89, and any variants thereof having one or more conservative amino acid substitutions within any of the variable light or variable heavy chain regions of said antigen binding protein.

In one embodiment the invention provides that the recombinant antigen binding protein of the invention comprises the variable light chain comprising an amino acid sequence having at least 90% sequence identity to SEQ ID NO. 91 and the variable heavy chain comprising an amino acid sequence having at least 90% sequence identity to SEQ ID NO. 75, and any variants thereof having one or more conservative amino acid substitutions within any of the variable light or variable heavy chain regions of said antigen binding protein. In one embodiment, the present invention provides a recombinant antigen binding protein that specifically binds to Nerve Growth factor (NGF) further comprising a constant region comprising the amino acids selected from either SEQ ID NO. 41 or 43. In one embodiment the present invention provides a nucleotide sequence coding for a constant region selected from a group consisting of SEQ ID NO. 42 or SEQ ID NO. 44. In one embodiment, the constant region of the antigen binding protein of the present invention lacks effector function. In one embodiment alterations to the constant region of the antigen binding protein of the invention prevents degradation of the antigen binding protein.

In one embodiment, the present invention provides a recombinant antigen binding protein that specifically binds to NGF further comprising a constant region comprising the amino acids sequence comprising SEQ ID. NO. 62. In one embodiment, the present invention provides a nucleotide sequence coding for the constant region comprising SEQ ID NO. 63. In one embodiment, the constant region of the antigen binding protein of the present invention lacks effector function. In one embodiment alterations to the constant region of the antigen binding protein of the invention prevents degradation of the antigen binding protein.

In one aspect the present invention provides nucleotide sequences that code for the recombinant antigen binding protein of the invention that specifically binds to Nerve Growth Factor (NGF) comprising a variable light chain (VL) comprising a Complementary Determining Region 1 (CDR1) nucleic acid sequences having at least 90% sequence identity to SEQ ID. NO. 11 or SEQ ID NO. 31; a Complementary Determining Region 1 (CDR2) comprising nucleotide sequences having at least 90% sequence identity to SEQ ID. NO. 12 or SEQ ID NO. 32; a Complementary Determining Region 1 (CDR3) comprising nucleotide sequences having at least 90% sequence identity to SEQ ID. NO. 13 or SEQ ID NO. 33; and a variable heavy chain (VH) comprising: a Complementary Determining Region 1 (CDR1) comprising nucleotide sequences having at least 90% sequence identity to SEQ ID. NO. 14 or SEQ ID NO. 34; a Complementary Determining Region 1 (CDR2) comprising nucleotide sequences having at least 90% sequence identity to SEQ ID. NO. 15 or SEQ ID NO. 35; and a Complementary Determining Region 1 (CDR3) comprising amino acid sequences having at least 90% sequence identity to SEQ ID. NO. 15 or SEQ ID NO. 36; and any variants thereof having one or more nucleic acid substitutions based on the degeneracy of the genetic code in at least one of CDR1, CDR2 or CDR3 within any of the variable light or variable heavy chain regions of said antigen binding protein.

In one embodiment the present invention provides a nucleotide sequence that codes for the antigen binding protein of the invention that comprises a light chain variable region (VL) comprising a Complimentary Determining Region 1 (CDR1) comprising a nucleotide sequence having at least about 90% sequence identity to the nucleotide sequence comprising SEQ ID NO. 11; a Complimentary Determining Region 2 (CDR2) comprising a nucleotide sequence having at least about 90% sequence identity to the nucleotide sequence comprising SEQ ID NO. 12; a Complimentary Determining Region 3 (CDR3) comprising a nucleotide sequence having at least about 90% sequence identity to the nucleotide sequence comprising SEQ ID NO. 13 and a heavy chain variable region (VH) comprising: a Complimentary Determining Region 1 (CDR1) comprising a nucleotide sequence having at least about 90% sequence identity to the nucleotide sequence comprising SEQ ID NO. 14; a Complimentary Determining Region 2 (CDR2) comprising a nucleotide sequence having at least about 90% sequence identity to the nucleotide sequence comprising SEQ ID NO. 15; a Complimentary Determining Region 3 (CDR3) comprising a nucleotide sequence having at least about 90% sequence identity to the nucleic sequence comprising SEQ ID NO. 16 and any variants thereof having one or more nucleic acid substitutions based on the degeneracy of the genetic code in at least one of CDR1, CDR2 or CDR3 within any of the variable light or variable heavy chain regions of said antigen binding protein.

In one embodiment the present invention provides a nucleotide sequence that codes for the antigen binding protein of the invention and comprises nucleotides that code for a light chain variable region (VL) comprising a Complimentary Determining Region 1 (CDR1) comprising a nucleotide sequence having at least about 90% sequence identity to the nucleotide sequence comprising SEQ ID NO. 31; a Complimentary Determining Region 2 (CDR2) comprising a nucleotide sequence having at least about 90% sequence identity to the nucleotide sequence comprising SEQ ID NO. 32; a Complimentary Determining Region 3 (CDR3) comprising a nucleotide sequence having at least about 90% sequence identity to the nucleotide sequence comprising SEQ ID NO. 33 and nucleotide sequences that code for a heavy chain variable region (VH) comprising: a Complimentary Determining Region 1 (CDR1) comprising a nucleotide sequence having at least about 90% sequence identity to the nucleotide sequence comprising SEQ ID NO. 34; a Complimentary Determining Region 2 (CDR2) comprising a nucleotide sequence having at least about 90% sequence identity to the nucleotide sequence comprising SEQ ID NO. 35; a Complimentary Determining Region 3 (CDR3) comprising a nucleotide sequence having at least about 90% sequence identity to the nucleotide sequence comprising SEQ ID NO. 36 and any variants thereof having one or more nucleic acid substitutions based on the degeneracy of the genetic code in at least one of CDR1, CDR2 or CDR3 within any of the variable light or variable heavy chain regions of said antigen binding protein.

In one aspect the present invention provides a nucleotide sequence coding for a recombinant antigen binding protein of the invention that specifically binds to Nerve Growth Factor (NGF) comprising nucleotides coding for a variable light chain comprising a nucleotide sequence protein having at least 90% sequence identity to the nucleotide sequences selected from the group consisting of: SEQ ID NO. 17; SEQ ID NO. 19; SEQ ID NO. 37; SEQ ID NO. 39; SEQ ID NO. 57; SEQ ID NO. 88; SEQ ID NO. 90; and SEQ ID NO. 92 and nucleotides that code for a variable heavy chain comprising a nucleotide sequence having at least 90% sequence identity to the nucleotide sequences selected from the group consisting of: SEQ ID NO. 18; SEQ ID NO. 20; SEQ ID NO. 38; SEQ ID NO. 40; SEQ ID NO. 58; SEQ ID. 76; and SEQ ID NO. 80. and any variants thereof having one or more nucleic acid substitutions based on the degeneracy of the genetic code within any of the variable light or variable heavy chain regions of said antigen binding protein.

In one embodiment, the invention provides that the nucleotide sequences coding for the recombinant antigen binding protein of the invention comprises nucleotide sequences that code for the variable light chain comprising a nucleotide sequence having at least 90% sequence identity to SEQ ID NO. 17 and nucleotide sequences that code for the variable heavy chain comprising a nucleotide sequence having at least 90% sequence identity to SEQ ID NO. 18, and any variants thereof having one or more nucleic acid substitutions based on the degeneracy of the genetic code within any of the variable light or variable heavy chain regions of said antigen binding protein. In one embodiment the invention provides a nucleotide sequence coding for an antigen binding protein of the invention wherein the nucleotide sequences code for the variable light chain which comprises a nucleotide sequence having at least 90% sequence identity to SEQ ID NO. 37 and nucleotide sequences coding for the variable heavy chain comprising a nucleotide sequence having at least 90% sequence identity to SEQ ID NO. 38 and any variants thereof having one or more nucleic acid substitutions based on the degeneracy of the genetic code within any of the variable light or variable heavy chain regions of said antigen binding protein.

In one embodiment, the invention provides that the nucleotide sequences coding for the recombinant antigen binding protein of the invention comprises nucleotide sequences that code for the variable light chain comprising a nucleotide sequence having at least 90% sequence identity to SEQ ID NO. 19 and nucleotide sequences that code for the variable heavy chain comprising a nucleotide sequence having at least 90% sequence identity to SEQ ID NO. 20, and any variants thereof having one or more nucleic acid substitutions based on the degeneracy of the genetic code within any of the variable light or variable heavy chain regions of said antigen binding protein. In one embodiment the invention provides a nucleotide sequence coding for an antigen binding protein of the invention wherein the nucleotide sequences code for the variable light chain which comprises a nucleotide sequence having at least 90% sequence identity to SEQ ID NO. 39 and nucleotide sequences coding for the variable heavy chain comprising a nucleotide sequence having at least 90% sequence identity to SEQ ID NO. 40 and any variants thereof having one or more nucleic acid substitutions based on the degeneracy of the genetic code within any of the variable light or variable heavy chain regions of said antigen binding protein.

In one embodiment, the invention provides that the nucleotide sequences coding for the recombinant antigen binding protein of the invention comprises nucleotide sequences that code for the variable light chain comprising a nucleotide sequence having at least 90% sequence identity to SEQ ID NO. 57 and nucleotide sequences that code for the variable heavy chain comprising a nucleotide sequence having at least 90% sequence identity to SEQ ID NO. 58, and any variants thereof having one or more nucleic acid substitutions based on the degeneracy of the genetic code within any of the variable light or variable heavy chain regions of said antigen binding protein.

In one embodiment, the invention provides that the nucleotide sequences coding for the recombinant antigen binding protein of the invention comprises nucleotide sequences that code for the variable light chain comprising a nucleotide sequence having at least 90% sequence identity to SEQ ID NO. 92 and nucleotide sequences that code for the variable heavy chain comprising a nucleotide sequence having at least 90% sequence identity to SEQ ID NO. 80, and any variants thereof having one or more nucleic acid substitutions based on the degeneracy of the genetic code within any of the variable light or variable heavy chain regions of said antigen binding protein. In one embodiment the invention provides a nucleotide sequence coding for an antigen binding protein of the invention wherein the nucleotide sequences code for the variable light chain which comprises a nucleotide sequence having at least 90% sequence identity to SEQ ID NO. 88 and nucleotide sequences coding for the variable heavy chain comprising a nucleotide sequence having at least 90% sequence identity to SEQ ID NO. 80 and any variants thereof having one or more nucleic acid substitutions based on the degeneracy of the genetic code within any of the variable light or variable heavy chain regions of said antigen binding protein. In one embodiment, the invention provides that the nucleotide sequences coding for the recombinant antigen binding protein of the invention comprises nucleotide sequences that code for the variable light chain comprising a nucleotide sequence having at least 90% sequence identity to SEQ ID NO. 92 and nucleotide sequences that code for the variable heavy chain comprising a nucleotide sequence having at least 90% sequence identity to SEQ ID NO. 76, and any variants thereof having one or more nucleic acid substitutions based on the degeneracy of the genetic code within any of the variable light or variable heavy chain regions of said antigen binding protein. In one embodiment the invention provides a nucleotide sequence coding for an antigen binding protein of the invention wherein the nucleotide sequences code for the variable light chain which comprises a nucleotide sequence having at least 90% sequence identity to SEQ ID NO. 88 and nucleotide sequences coding for the variable heavy chain comprising a nucleotide sequence having at least 90% sequence identity to SEQ ID NO. 76 and any variants thereof having one or more nucleic acid substitutions based on the degeneracy of the genetic code within any of the variable light or variable heavy chain regions of said antigen binding protein. In one embodiment, the invention provides that the nucleotide sequences coding for the recombinant antigen binding protein of the invention comprises nucleotide sequences that code for the variable light chain comprising a nucleotide sequence having at least 90% sequence identity to SEQ ID NO. 90 and nucleotide sequences that code for the variable heavy chain comprising a nucleotide sequence having at least 90% sequence identity to SEQ ID NO. 76, and any variants thereof having one or more nucleic acid substitutions based on the degeneracy of the genetic code within any of the variable light or variable heavy chain regions of said antigen binding protein.

In one or more embodiments, the antigen binding protein of the invention inhibits the binding of NGF to the TrkA receptor. In one or more embodiments, the antigen binding protein of the invention inhibits the biological function associated with the binding of NGF to the TrkA receptor. In one or more embodiments, the antigen binding protein of the invention inhibits the binding of NGF to both the TrkA receptor. In one or more embodiments, the antigen binding protein inhibits the biological function associated with the binding of NGF to the TrkA with or without the p75 receptors which includes blocking signal transduction and pathways associated with binding of NGF to the TrkA receptor.

In one or more embodiment, the antigen binding protein of the invention reduces or eliminates an NGF related disorder by disrupting the signal associated with the binding of NGF to the TrkA and p75 receptors. In one or more embodiments, the NGF-related disorder is selected from the group consisting of: cardiovascular diseases, atherosclerosis, obesity, type 2 diabetes, metabolic syndrome, pain and inflammation. In one embodiment, the NGF-related disorder is pain. In one embodiment said NGF-related disorder is a pain disorder and is selected from the group consisting of: osteoarthritis pain, rheumatoid arthritis pain, surgical and postsurgical pain, incisional pain, general inflammatory pain, cancer pain, pain from trauma, neuropathic pain, neuralgia, diabetic neuropathy pain, pain associated with rheumatic diseases, pain associated with musculoskeletal diseases, visceral pain, and gastrointestinal pain. In one embodiment, the NGF-related disorder comprises osteoarthritis pain. In one embodiment, the NGF-related disorder comprises surgical and postsurgical pain. In one embodiment, the NGF-related disorder comprises cancer pain.

In one or more aspects the antigen binding protein of the invention is selected from the group consisting of: a monoclonal antibody; a chimeric antibody, a single chain antibody, a tetrameric antibody, a tetravalent antibody, a multi-specific antibody, a domain-specific antibody, a domain-deleted antibody, a fusion protein, an ScFc fusion protein, an Fab fragment, an Fab' fragment, an F(ab')$_2$ fragment, an Fv fragment, an ScFv fragment, an Fd fragment, a single domain antibody, a dAb fragment, a small modular immunopharmaceutical (SMIP) a nanobody, and IgNAR molecule. In one embodiment, the antigen binding protein is a monoclonal antibody. In one embodiment, the antigen binding protein is a chimeric antibody.

In one embodiment, the antigen binding protein of the invention is selected from a canine or caninized monoclonal antibody, a felinized monoclonal antibody, an equinized monoclonal antibody or a humanized monoclonal antibody. In one embodiments, the antigen binding protein is a canine or caninized antibody. In one embodiment, the antigen binding protein of the invention is a felinized antibody. In one embodiments, the antigen binding protein of the invention is an equinized antibody. In one embodiments, the antigen binding protein of the invention is a humanized antibody.

In one or more aspects, the invention provides a pharmaceutical composition comprising a therapeutically effective amount of the antigen binding protein and a pharmaceutically acceptable carrier. In one embodiment, the invention provides a veterinary composition comprising a therapeutically effective amount of the antigen binding protein and a pharmaceutically acceptable carrier. In one embodiment, the invention provides a pharmaceutical or veterinary composition comprising a therapeutically effective amount of the antigen binding protein and a pharmaceutically acceptable carrier. In one embodiment, the pharmaceutical composition of the invention is used in the treatment of an NGF related disorder. In one embodiment, the NGF related disorder is selected from the group consisting of: cardiovascular diseases, atherosclerosis, obesity, type 2 diabetes, metabolic syndrome, pain and inflammation. In one embodiment, the NGF related disorder comprises pain. In one embodiment, the pharmaceutical composition is used in the treatment of pain. In one embodiment, the pharmaceutical composition is used for the treatment of a pain and the type of pain is selected from osteoarthritis pain, rheumatoid arthritis pain, surgical and postsurgical pain, incisional pain, general inflammatory pain, cancer pain, pain from trauma, neuropathic pain, neuralgia, diabetic neuropathy pain, pain associated with rheumatic diseases, pain associated with musculoskeletal diseases, visceral pain, and gastrointestinal pain. In one embodiment, the pain comprises osteoarthritis pain. In one embodiment, the pain comprises surgical and post-surgical pain. In one embodiment, the pain comprises cancer pain. In one or more embodiments, the pharmaceutical composition of the invention is for use in a canine. In one or more embodiments, the pharmaceutical composition of the invention is for use in felines. In one or more embodiments, the pharmaceutical composition of the invention is for use in equine. In one or more embodiments, the pharmaceutical composition of the invention is for use in humans.

In one or more embodiments, the pharmaceutical composition of the invention has no significant adverse effect on the immune system of a canine. In one embodiment, the composition of the invention has no significant adverse effect on the immune system of a feline. In one or more embodiment, the composition of the invention has no significant adverse effect on the immune system of an equine. In one embodiment, the composition of the invention has no significant adverse effect on the immune system of a human. In one embodiment, the pharmaceutical composition is a veterinary composition.

In one or more embodiments, the present invention provides a host cell that produces any one or more of the antigen binding proteins of the present invention.

In one or more embodiments, the invention provides a vector comprising the any one or more of the nucleic acids of the present invention.

In one or more embodiments, the invention provides a host cell comprising the any one or more of the nucleic acids of the present invention.

In one or more embodiments, the invention provides a host cell comprising the vector that comprises any one or more of the nucleic acids of the present invention.

In one or more embodiments, the invention provides a host cell comprising any one or more of the nucleic acids of the present invention.

In one or more aspects, the present invention provides a method of producing the antigen binding protein of the invention by culturing the host cell of the invention under conditions that result in production of the antigen binding protein and subsequently isolating the antigen binding protein from the host cell or culture medium of the host cell.

In one or more aspects, the present invention provides a method of treating a subject for an NGF-related disorder comprising administering to said subject a therapeutically effective amount of the pharmaceutical or veterinary composition the present invention. In one embodiment, the invention provides that the NGF-related disorder is selected from the group consisting of: cardiovascular diseases, atherosclerosis, obesity, type 2 diabetes, metabolic syndrome, pain and inflammation. In one embodiment, the NGF related disorder comprises pain. In one embodiment, the NGF-related disorder is a pain disorder and is selected from the group consisting of: osteoarthritis pain, rheumatoid arthritis pain, surgical and postsurgical pain, incisional pain, general inflammatory pain, cancer pain, pain from trauma, neuropathic pain, neuralgia, diabetic neuropathy pain, pain associated with rheumatic diseases, pain associated with musculoskeletal diseases, visceral pain, and gastrointestinal pain. In one embodiment, the NGF related disorder comprises osteoarthritis pain. In one embodiment, the NGF related disorder comprises surgical and post-surgical pain. In one embodiment, the NGF disorder is cancer pain. In one embodiment, the subject is selected from the group consisting of: canines, felines, humans and equines.

In one embodiment, the subject comprises canines. In one embodiment, the subject comprises felines. In one embodiment, the subject comprises equines. In one embodiment, the subject comprises humans.

In one or more embodiments, the present invention provides a method of detecting or quantitating NGF levels in a biological sample, the method comprising:
(a) incubating a clinical or biological sample containing NGF in the presence of any one of the antigen binding protein of the present invention; and
(b) detecting the antigen binding protein which are bound to NGF in the sample.

In some embodiments, the antigen binding protein of the invention is detectably labeled. In some embodiments, the antigen binding protein is unlabeled is used in combination with a second antigen binding protein or fragments which is detectably labeled. In one embodiment, the invention comprises a kit comprising the antigen binding protein of the invention.

BRIEF DESCRIPTION OF THE SEQUENCES

Figure 1:
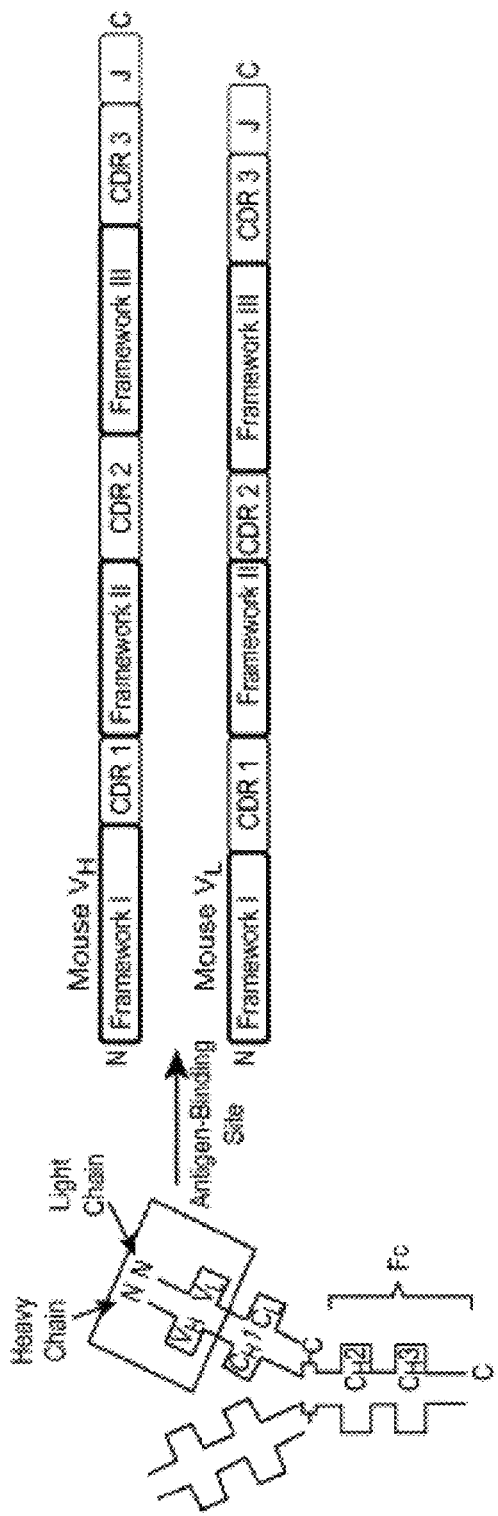
FIG. 1: is a schematic representation of the general structure of a mouse immunoglobulin G (IgG) molecule highlighting the antigen binding site.

| SEQ ID NO. | DESCRIPTION | SEQUENCE |
|---|---|---|
| 1 | Amino acid sequence for ZTS-841 Variable Light Chain CDR1 | TNNIGILG |
| 2 | Amino acid sequence for ZTS-841 Variable Light Chain CDR2 | GNG |
| 3 | Amino acid sequence for ZTS-841 Variable Light Chain CDR3 | QSFDTTLGAHV |
| 4 | Amino acid sequence for ZTS-841 Variable Heavy Chain CDR1 | GFTFSSHG |
| 5 | Amino acid sequence for ZTS-841 Variable Heavy Chain CDR2 | INSGGSST |
| 6 | Amino acid sequence for ZTS-841 Variable Heavy Chain CDR3 | AKESVGGWEQLVGPHFDY |
| 7 | Amino acid sequence for ZTS-841 Variable Light Chain | QSVLTQPTSVSGSLGQRVTISCSGSTNNIGILGASWYQ LFPGKAPKLLVYGNGNRPSGVPDRFSGADSGDSVTLTI TGLQAEDEADYYCQSFDTTLGAHVFGGGTHLTVL |
| 8 | Amino acid sequence for ZTS-841 Variable Heavy Chain | EVQLVESGGDLVKPGGSLRLSCVASGFTFSSHGMHWV RQSPGKGLQWVAVINSGGSSTYYTDAVKGRFTISRDN AKNTVYLQMNSLRAEDTAMYYCAKESVGGWEQLVGP HFDYWGQGTLVIVSS |
| 9 | Amino acid sequence for canfel_chimera 841 variable light chain | QSVLTQPTSVSGSLGQRVTISCSGSTNNIGILGASWYQ LFPGKAPKLLVYGNGNRPSGVPDRFSGADSGDSVTLTI TGLQAEDEADYYCQSFDTTLGAHVFGGGTHLTVL |
| 10 | Amino acid sequence for canfel_chimera 841 variable heavy chain | EVQLVESGGDLVKPGGSLRLSCVASGFTFSSHGMHWV RQSPGKGLQWVAVINSGGSSTYYTDAVKGRFTISRDN AKNTVYLQMNSLRAEDTAMYYCAKESVGGWEQLVGP HFDYWGQGTLVIVSS |
| 11 | Nucleotide sequence for ZTS-841 Variable Light Chain CDR1 | ACGAACAACATCGGTATTCTTGGT |
| 12 | Nucleotide sequence for ZTS-841 Variable Light Chain CDR2 | GGTAATGGG |
| 13 | Nucleotide sequence for ZTS-841 Variable Light Chain CDR3 | CAGTCCTTTGATACCACGCTTGGTGCTCATGTGTTC |
| 14 | Nucleotide sequence for ZTS-841 Variable Heavy Chain CDR1 | GGATTCACCTTCAGTAGCCACGGC |
| 15 | Nucleotide sequence for ZTS-841 Variable Heavy Chain CDR2 | ATTAACAGCGGTGGAAGTAGCACA |
| 16 | Nucleotide sequence for ZTS-841 Variable Heavy Chain CDR3 | GCAAAGGAGTCCGTCGGGGGTGGGAGCAACTGGT CGGACCTCATTTTGACTAC |
| 17 | Nucleotide sequence for ZTS 841 variable light chain | CAGTCTGTGCTGACTCAGCCGACCTCAGTGTCAGGG TCCCTTGGCCAGAGGGTCACCATCTCCTGCTCTGGA AGCACGAACAACATCGGTATTCTTGGTGCGAGCTGG TACCAACTGTTCCCAGGAAAGGCCCCTAAACTCCTC GTGTACGGTAATGGGAATCGACCGTCAGGGGTCCCT GACCGGTTTTCCGGCGCCGACTCTGGCGACTCAGTC ACCCTGACCATCACTGGGCTTCAGGCTGAGGACGAG GCTGATTATTACTGCCAGTCCTTTGATACCACGCTTG GTGCTCATGTGTTCGGCGGAGGCACCCACCTGACCG TCCTT |
| 18 | Nucleotide sequence for ZTS-841 variable heavy chain | GAGGTGCAGCTGGTGGAGTCTGGGGGAGATTTGGT GAAGCCTGGGGGGTCCTTGAGACTGTCCTGTGTGGC CTCTGGATTCACCTTCAGTAGCCACGGCATGCACTG GGTCCGTCAGTCTCCAGGGAAGGGACTGCAGTGGG TCGCAGTTATTAACAGCGGTGGAAGTAGCACATACTA CACAGACGCTGTGAAGGGCCGATTCACCATCTCCAG AGACAACGCCAAGAACACAGTGTATCTACAGATGAA CAGCCTGAGAGCCGAGGACACGGCCATGTATTACTG |

BRIEF DESCRIPTION OF THE SEQUENCES

| SEQ ID NO. | DESCRIPTION | SEQUENCE |
|---|---|---|
| | | TGCAAAGGAGTCCGTCGGGGGGTGGGAGCAACTGG TCGGACCTCATTTTGACTACTGGGGCCAGGGAACCC TGGTCATCGTCTCGAGC |
| 19 | Nucleotide sequence for canfel_chimera 841 variable light chain | CAGGCGGTGCTGAACCAGCCGGCGAGCGTGAGCGG CGCGCTGGGCCAGAAAGTGACCATTAGCTGCAGCG GCAGCACCATGGATATTGATATTTTTGGCGTGAGCTG GTATCAGCAGCTGCCGGGCAAAGCGCCGAAACTGCT GGTGGATAGCGATGGCGATCGCCCGAGCGGCATTC CGGATCGCTTTAGCGGCAGCCGCAGCGGCAACAGC GGCACCCTGACCATTACCGGCCTGCAGGCGGAAGAT GAAGCGGATTATCATTGCCAGAGCGGCGATAGCACC CTGGGCGCGCTGGCGATTTTTGGCGGCGGCACCCA TGTGACCGTGCTG |
| 20 | Nucleotide sequence for canfel_chimera 841 variable heavy chain | GAAGTGCAGCTGGTGGAAAGCGGCGGCGATCTGGT GAAACCGGGCGGCAGCCTGCGCCTGAGCTGCGTGG CGAGCGGCTTTACCTTTAGCAGCCATGGCATGCATT GGGTGCGCCAGAGCCCGGGCAAAGGCCTGCAGTGG GTGGCGGTGATTAACAGCGGCGGCAGCAGCACCTAT TATACCGATGCGGTGAAAGGCCGCTTTACCATTAGC CGCGATAACGCGAAAAACACCGTGTATCTGCAGATG AACAGCCTGCGCGCGGAAGATACCGCGATGTATTAT TGCGCGAAAGAAAGCGTGGGCGGCTGGGAACAGCT GGTGGGCCCGCATTTTGATTATTGGGGCCAGGGCAC CCTGGTGATTGTCTCGAGC |
| 21 | Amino acid sequence for ZTS-842 Variable Light Chain CDR1 | TMDIDIFG |
| 22 | Amino acid sequence for ZTS-842 Variable Light Chain CDR2 | SDG |
| 23 | Amino acid sequence for ZTS-842 Variable Light Chain CDR3 | QSGDSTLGALAI |
| 24 | Amino acid sequence for ZTS-842 Variable Heavy Chain CDR1 | GFTFSTYG |
| 25 | Amino acid sequence for ZTS-842 Variable Heavy Chain CDR2 | ISSGGSST |
| 26 | Amino acid sequence for ZTS-842 Variable Heavy Chain CDR3 | AGSRYTYAYGGGYEFHF |
| 27 | Amino acid sequence for ZTS-842 Variable Light Chain | QAVLNQPASVSGALGQKVTISCSGSTMDIDIFGVSWYQ QLPGKAPKLLVDSDGDRPSGIPDRFSGSRSGNSGTLTI TGLQAEDEADYHCQSGDSTLGALAIFGGGTHVTVL |
| 28 | Amino acid sequence for ZTS-842 Variable Heavy Chain | EVQLVESGGDLVKPGGSLRLSCVASGFTFSTYGINWVR QAPGKGLQWVAYISSGGSSTYYADPVKGRFTISRDDAK NMLYLQMNSLRAEDTAIYYCAGSRYTYAYGGGYEFHF WGQGTLVTVSS |
| 29 | Amino acid sequence for canfel_chimera 842 variable light chain | QSVLTQPTSVSGSLGQRVTISCSGSTNNIGILGASWYQ LFPGKAPKLLVYGNGNRPSGVPDRFSGADSGDSVTLTI TGLQAEDEADYYCQSFDTTLGAHVFGGGTHLTVL |
| 30 | Amino acid sequence for canfel_chimera 842 variable heavy chain | EVQLVESGGDLVKPGGSLRLSCVASGFTFSTYGINWVR QAPGKGLQWVAYISSGGSSTYYADPVKGRFTISRDDAK NMLYLQMNSLRAEDTAIYYCAGSRYTYAYGGGYEFHF WGQGTLVTVSS |
| 31 | Nucleotide sequence for ZTS-842 Variable Light Chain CDR1 | ACAATGGACATTGATATATTTGGT |
| 32 | Nucleotide sequence for ZTS-842 Variable Light Chain CDR2 | AGTGATGGG |
| 33 | Nucleotide sequence for ZTS-842 Variable Light Chain CDR3 | CAGTCTGGTGATTCCACGCTTGGTGCCCTTGCTATT |

BRIEF DESCRIPTION OF THE SEQUENCES

| SEQ ID NO. | DESCRIPTION | SEQUENCE |
| --- | --- | --- |
| 34 | Nucleotide sequence for ZTS-842 Variable Heavy Chain CDR1 | GGATTCACCTTCAGTACCTATGGC |
| 35 | Nucleotide sequence for ZTS-842 Variable Heavy Chain CDR2 | ATTAGTAGTGGTGGAAGTAGCACA |
| 36 | Nucleotide sequence for ZTS-842 Variable Heavy Chain CDR3 | GCGGGTAGTAGATATACATATGCATACGGAGGAGGATATGAGTTTCACTTC |
| 37 | Nucleotide sequence for ZTS 842 variable light chain | CAGGCTGTGCTGAATCAGCCGGCCTCAGTGTCTGGGGCCCTGGGCCAGAAGGTCACCATCTCCTGCTCTGGAAGCACAATGGACATTGATATATTTGGTGTGAGCTGGTACCAACAGCTCCCAGGAAAGGCCCCTAAACTCCTCGTGGACAGTGATGGGGATCGACCCTCAGGGATCCCTGACAGATTTTCTGGCTCCAGGTCTGGCAACTCAGGCACCCTGACCATCACTGGGCTCCAGGCTGAGGACGAGGCTGATTATCACTGTCAGTCTGGTGATTCCACGCTTGGTGCCCTTGCTATTTTCGGCGGAGGCACCCATGTGACCGTCCTT |
| 38 | Nucleotide sequence for ZTS-842 variable heavy chain | GAGGTACAACTGGTGGAATCTGGGGGAGACCTGGTGAAGCCTGGGGGATCCCTGAGACTCTCCTGTGTGGCCTCTGGATTCACCTTCAGTACCTATGCATCAACTGGGTCCGCCAGGCTCCAGGGAAGGGGCTGCAGTGGGTCGCATACATTAGTAGTGGTGGAAGTAGCACATACTATGCAGATCCTGTGAAGGGCCGGTTCACCATCTCCAGAGACGACGCCAAGAACATGCTGTATCTTCAGATGAACAGCCTGAGAGCCGAGGACACGGCCATATATTACTGTGCGGGTAGTAGATATACATATGCATACGGAGGAGGATATGAGTTTCACTTCTGGGGCCAGGGAACCCTGGTCACCGTCTCGAGC |
| 39 | Nucleotide sequence for canfel_chimera 842 variable light chain | CAGGCGGTGCTGAACCAGCCGGCGAGCGTGAGCGGCGCGCTGGGCCAGAAAGTGACCATTAGCTGCAGCGGCAGCACCATGGATATTGATATTTTTGGCGTGAGCTGGTATCAGCAGCTGCCGGGCAAAGCGCCGAAACTGCTGGTGGATAGCGATGGCGATCGCCCGAGCGGCATTCCGGATCGCTTTAGCGGCAGCCGCAGCGGCAACAGCGGCACCCTGACCATTACCGGCCTGCAGGCGGAAGATGAAGCGGATTATCATTGCCAGAGCGGCGATAGCACCCTGGGCGCGCTGGCGATTTTTGGCGGCGGCACCCATGTGACCGTGCTG |
| 40 | Nucleotide sequence for canfel_chimera 842 variable heavy chain | GAAGTGCAGCTGGTGGAAAGCGGCGGCGATCTGGTGAAACCGGGCGGCAGCCTGCGCCTGAGCTGCGTGGCGAGCGGCTTTACCTTTAGCACCTATGGCATTAACTGGGTGCGCCAGGCGCCGGGCAAAGGCCTGCAGTGGGTGGCGTATATTAGCAGCGGCGGCAGCAGCACCTATTATGCGGATCCGGTGAAAGGCCGCTTTACCATTAGCCGCGATGATGCGAAAAACATGCTGTATCTGCAGATGAACAGCCTGCGCGCGGAAGATACCGCGATTTATTATTGCGCGGGCAGCCGCTATACCTATGCGTATGGCGGCGGCTATGAATTTCATTTTTGGGGCCAGGGCACCCTGGTGACCGTCTCGAGC |
| 41 | Amino Acid sequence for HC-65 | ASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENGRVPRPPDCPKCPAPEMLGGPSVFIFPPKPKDTLLIARTPEVTCVVVDLDPEDPEVQISWFVDGKQMQTAKTQPREEQFNGTYRVVSVLPIGHQDWLKGKQFTCKVNNKALPSPIERTISKARGQAHQPSVYVLPPSREELSKNTVSLTCLIKDFFPPDIDVEWQSNGQQEPESKYRTTPPQLDEDGSYFLYSKLSVDKSRWQRGDTFICAVMHEALHNHYTQESLSHSPGK |
| 42 | Nucleic acid sequence for HC-65 | GCCTCAACAACTGCTCCTAGCGTGTTTCCCCTGGCCCCTAGCTGCGGAAGTACCTCAGGCAGCACAGTGGCCCTGGCTTGTCTGGTGTCTGGATATTTCCCTGAGCCAGTGACCGTGAGTTGGAACAGCGGCTCTCTGACCTCCGGGGTGCACACATTTCCATCTGTGCTGCAGTCTAGTGGCCTGTACTCCCTGTCAAGCATGGTGACTGTGCCTTCCTCTAGGTGGCCATCAGAAACTTTCACCTGCAACG |

| SEQ ID NO. | DESCRIPTION | SEQUENCE |
|---|---|---|
| | | TGGCCCATCCCGCCAGCAAGACCAAAGTGGACAAGC<br>CCGTGCCTAAAAGGGAGAATGGAAGGGTGCCAAGAC<br>CACCTGATTGCCCTAAGTGTCCAGCTCCAGAAATGCT<br>GGGAGGACCAAGCGTGTTCATCTTTCCACCCAAGCC<br>CAAAGACACACTGCTGATTGCTAGAACTCCCGAGGT<br>GACCTGCGTGGTGGTGGACCTGGATCCAGAGGACC<br>CCGAAGTGCAGATCTCCTGGTTCGTGGATGGGAAGC<br>AGATGCAGACAGCCAAAACTCAGCCTCGGGAGGAAC<br>AGTTTAACGGAACCTATAGAGTGGTGTCTGTGCTGC<br>CAATTGGACACCAGGACTGGCTGAAGGGCAAACAGT<br>TTACATGCAAGGTGAACAACAAGGCCCTGCCTAGTC<br>CAATCGAGAGGACTATTTCAAAAGCTAGGGGACAGG<br>CTCATCAGCCTTCCGTGTATGTGCTGCCTCCATCCC<br>GGGAGGAACTGTCTAAGAACACAGTGAGTCTGACTT<br>GTCTGATCAAAGATTTCTTTCCCCCTGACATTGATGT<br>GGAGTGGCAGAGCAATGGGCAGCAGGAGCCAGAAT<br>CCAAGTACAGAACCACACCACCCCAGCTGGACGAAG<br>ATGGCTCCTATTTCCTGTACAGTAAGCTGTCAGTGGA<br>CAAATCTAGGTGGCAGCGCGGGGATACCTTTATCTG<br>CGCCGTGATGCACGAGGCTCTGCACAATCATTACAC<br>ACAAGAAAGTCTGTCACATAGCCCCGGCAAG |
| 43 | Amino Acid sequence for HC-65e | ASTTAPSVFPLAPSCGSTSGSTVALACLVSGYFPEPVT<br>VSWNSGSLTSGVHTFPSVLQSSGLYSLSSMVTVPSSR<br>WPSETFTCNVAHPASKTKVDKPVPKRENGRVPRPPDC<br>PKCPAPEAAGAPSVFIFPPKPKDTLLIARTPEVTCVVVD<br>LDPEDPEVQISWFVDGKQMQTAKTQPREEQFNGTYRV<br>VSVLPIGHQDWLKGKQFTCKVNNKALPSPIERTISKARG<br>QAHQPSVYVLPPSREELSKNTVSLTCLIKDFFPPDIDVE<br>WQSNGQQEPESKYRTTPPQLDEDGSYFLYSKLSVDKS<br>RWQRGDTFICAVMHEALHNHYTQESLSHSPGK |
| 44 | Nucleic acid sequence for HC-65e | GCCTCAACAACTGCTCCTAGCGTGTTTCCCCTGGCC<br>CCTAGCTGCGGAAGTACCTCAGGCAGCACAGTGGCC<br>CTGGCTTGTCTGGTGTCTGGATATTTCCCTGAGCCA<br>GTGACCGTGAGTTGGAACAGCGGCTCTCTGACCTCC<br>GGGGTGCACACATTTCCATCTGTGCTGCAGTCTAGT<br>GGCCTGTACTCCCTGTCAAGCATGGTGACTGTGCCT<br>TCCTCTAGGTGGCCATCAGAAACTTTCACCTGCAACG<br>TGGCCCATCCCGCCAGCAAGACCAAAGTGGACAAGC<br>CCGTGCCTAAAAGGGAGAATGGAAGGGTGCCAAGAC<br>CACCTGATTGCCCTAAGTGTCCAGCTCCAGAAGCGG<br>CGGGAGCACCAAGCGTGTTCATCTTTCCACCCAAGC<br>CCAAAGACACACTGCTGATTGCTAGAACTCCCGAGG<br>TGACCTGCGTGGTGGTGGACCTGGATCCAGAGGAC<br>CCCGAAGTGCAGATCTCCTGGTTCGTGGATGGGAAG<br>CAGATGCAGACAGCCAAAACTCAGCCTCGGGAGGAA<br>CAGTTTAACGGAACCTATAGAGTGGTGTCTGTGCTG<br>CCAATTGGACACCAGGACTGGCTGAAGGGCAAACAG<br>TTTACATGCAAGGTGAACAACAAGGCCCTGCCTAGT<br>CCAATCGAGAGGACTATTTCAAAAGCTAGGGGACAG<br>GCTCATCAGCCTTCCGTGTATGTGCTGCCTCCATCC<br>CGGGAGGAACTGTCTAAGAACACAGTGAGTCTGACT<br>TGTCTGATCAAAGATTTCTTTCCCCCTGACATTGATG<br>TGGAGTGGCAGAGCAATGGGCAGCAGGAGCCAGAA<br>TCCAAGTACAGAACCACACCACCCCAGCTGGACGAA<br>GATGGCTCCTATTTCCTGTACAGTAAGCTGTCAGTGG<br>ACAAATCTAGGTGGCAGCGCGGGGATACCTTTATCT<br>GCGCCGTGATGCACGAGGCTCTGCACAATCATTACA<br>CACAAGAAAGTCTGTCACATAGCCCCGGCAAG |
| 45 | Amino Acid sequence for 13L11VL CDR1 | NIGSKD |
| 46 | Amino Acid sequence for 13L11VL CDR2 | SDS |
| 47 | Amino Acid sequence for 13L11VL CDR3 | QVWDISADAIV |
| 48 | Amino Acid sequence for 13L11VH CDR1 | GYTFTDYY |

BRIEF DESCRIPTION OF THE SEQUENCES

| SEQ ID NO. | DESCRIPTION | SEQUENCE |
|---|---|---|
| 49 | Amino Acid sequence for 13L11VH CDR1 | IDPGNGAT |
| 50 | Amino Acid sequence for 13L11VH CDR1 | APLGYVPASTSEY |
| 51 | Amino Acid sequence for 13L11VL | SYVLTQPPSVTVTLRQTAHITCGGDNIGSKDVYWYQQK PGQAPVLIIYSDSKRPTGIPERFSGSNSGNMATLTISGA LAEDEADYYCQVWDISADAIVFGGGTHLTVL |
| 52 | Amino Acid sequence for 13L11VH | EVQLVQSAAEVKKPGASVKVSCKTSGYTFTDYYMHWV QQAPGAGLNWMGRIDPGNGATRYAQKFQGRLTLTADT STSTAYMELSGLRAEDTAVYYCAPLGYVPASTSEYWG QGTLVSVSS |
| 53 | Nucleotide sequence for 13L11VL | TCCTATGTGCTGACCCAGCCACCATCAGTGACTGTG ACCCTGAGGCAGACGGCCCACATCACCTGTGGGGG AGACAACATTGGAAGTAAAGATGTTTATTGGTACCAG CAGAAGCCGGGCCAGGCCCCCGTGTTGATTATCTAT AGTGATAGCAAGAGGCCGACAGGGATCCCTGAGCG ATTCTCCGGCTCCAACTCGGGGAACATGGCCACCCT GACCATCAGTGGGGCCTTGGCGAGGATGAGGCTG ACTATTACTGCCAGGTATGGGACATCAGTGCTGATG CTATTGTGTTCGGCGGAGGCACCCATCTGACCGTCC TT |
| 54 | Nucleotide sequence for 13L11VH | GAGGTCCAGCTGGTGCAGTCTGCAGCTGAGGTTAAG AAGCCAGGGGCATCTGTAAAGGTCTCCTGCAAGACC TCTGGATACACCTTCACTGACTACTATATGCACTGGG TACAACAGGCTCCAGGAGCAGGGCTCAATTGGATGG GACGGATTGATCCTGGAAATGGTGCCACAAGGTATG CACAGAAGTTCCAGGGCAGACTCACCCTGACGGCAG ACACATCCACAAGCACAGCCTACATGGAGCTGAGCG GTCTGAGAGCTGAGGACACAGCTGTGTACTACTGTG CGCCCCTAGGGTACGTGCCTGCATCAACATCTGAGT ACTGGGGCCAGGGCACCCTGGTCAGCGTCTCGAGC |
| 55 | Amino Acid sequence for Feline 205 VL | QAVLNQPSSVSGALGQRVTISCSGSTMDIDIFGVSWYQ QIPGMAPKTIIDSDGDRPSGVPDRFSGSKSGSTGTLTIT GLQAEDEADYYCQSGDSTLGALAIFGGGTHVTVL |
| 56 | Amino Acid sequence for Feline 205 VH | DVQLVESGGDLVKPGGSLRLTCVASGFTFSTYGINWVR QAPGKGLQWVAYISSGGSSTYYADPVKGRFTISRDNAK NMLYLQMNNLKTEDTATYYCAGSRYTYAYGGGYEFHF WGQGTLVTVSS |
| 57 | Nucleotide sequence for Feline 205 VL | CAGGCGGTGCTGAACCAGCCGAGCAGCGTGAGCGG CGGCTGGGCCAGCGCGTGACCATTAGCTGCAGCG GCAGCACCATGGATATTGATATTTTTGGCGTGAGCTG GTATCAGCAGATTCCGGGCATGGCGCCGAAAACCAT TATTGATAGCGATGGCGATCGCCCGAGCGGCGTGCC GGATCGCTTTAGCGGCAGCAAAAGCGGCAGCACCG GCACCCTGACCATTACCGGCCTGCAGGCGGAAGATG AAGCGGATTATTATTGCCAGAGCGGCGATAGCACCC TGGGCGCGCTGGCGATTTTTGGCGGCGGCACCCAT GTGACCGTGCTG |
| 58 | Nucleotide sequence for Feline 205 VH | GAGGTACAACTGGTGGAATCTGGGGGAGACCTGGT GAAGCCTGGGGGATCCCTGAGACTCTCCTGTGTGGC CTCTGGATTCACCTTCAGTACCTATGGCATCAACTGG GTCCGCCAGGCTCCAGGGAAGGGGCTGCAGTGGGT CGCATACATTAGTAGTGGTGGAAGTAGCACATACTAT GCAGATCCTGTGAAGGGCCGGTTCACCATCTCCAGA GACGACGCCAAGAACATGCTGTATCTTCAGATGAAC AGCCTGAGAGCCGAGGACACGGCCATATATTACTGT GCGGGTAGTAGATATACATATGCATACGGAGGAGGA TATGAGTTTCACTTCTGGGGCCAGGGAACCCTGGTC ACCGTCTCGAGC |
| 59 | Amino acid sequence for Canine NGF [Canis lupus familiaris] AAY16195.1 | QHSLDTALRRARSAPAGAIAARVTGQTRNITVDPKLFKK RRLRSPRVLFSTHPPPVAADAQDLDLEAGSTASVNRTH RSKRSSPHPVFHRGEFSVCDSVSVWVGDKTTATDIKG KEVMVLGEVNINNSVFKQYFFETKCRDPTPVDSGCRGI |

BRIEF DESCRIPTION OF THE SEQUENCES

| SEQ ID NO. | DESCRIPTION | SEQUENCE |
|---|---|---|
| | | DSKHWNSYCTTTHTFVKALTMDGKQAAWRFIRIDTACV CVLSRKAGRRA |
| 60 | Amino acid sequence for canine lambda chain | GQPKASPSVTLFPPSSEELGANKATLVCLISDFYPSGVT VAWKADGSPVTQGVETTKPSKQSNNKYAASSYLSLTP DKWKSHSSFSCLVTHEGSTVEKKVAPAECS |
| 61 | Nucleotide sequence for canine lambda chain | GGACAACCGAAGGCCTCCCCCTCGGTCACACTCTTC CCGCCCTCCTCTGAGGAGCTCGGCGCCAACAAGGC CACCCTGGTGTGCCTCATCAGCGACTTCTACCCCAG CGGCGTGACGGTGGCCTGGAAGGCAGACGGCAGCC CCGTCACCCAGGGCGTGGAGACCACCAAGCCCTCC AAGCAGAGCAACAACAAGTACGCGGCCAGCAGCTAC CTGAGCCTGACGCCTGACAAGTGGAAATCTCACAGC AGCTTCAGCTGCCTGGTCACGCACGAGGGGAGCAC CGTGGAGAAGAAGGTGGCCCCCGCAGAGTGCTCT |
| 62 | Amino acid sequence for feline HC | ASTTAPSVFPLAPSCGTTSGATVALACLVLGYFPEPVTV SWNSGALTSGVHTFPAVLQASGLYSLSSMVTVPSSRW LSDTFTCNVAHPPSNTKVDKTVRKTDHPPGPKPCDCP KCPPPEMLGGPSIFIFPPKPKDTLSISRTPEVTCLVVDLG PDDSDVQITWFVDNTQVYTAKTSPREEQFNSTYRVVSV LPILHQDWLKGKEFKCKVNSKSLPSPIERTISKAKGQPH EPQVYVLPPAQEELSRNKVSVTCLIKSFHPPDIAVEWEI TGQPEPENNYRTTPPQLDSDGTYFVYSKLSVDRSHWQ RGNTYTCSVSHEALHSHHTQKSLTQSPGK |
| 63 | Nucleotide sequence for feline HC | GCCTCCACCACGGCCCCATCGGTGTTCCCACTGGCC CCCAGCTGCGGGACCACATCTGGCGCCACCGTGGC CCTGGCCTGCCTGGTGTTAGGCTACTTCCCTGAGCC GGTGACCGTGTCCTGGAACTCCGGCGCCCTGACCA GCGGTGTGCACACCTTCCCGGCCGTCCTGCAGGCC TCGGGGCTGTACTCTCTCAGCAGCATGGTGACAGTG CCCTCCAGCAGGTGGCTCAGTGACACCTTCACCTGC AACGTGGCCCACCCGCCCAGCAACACCAAGGTGGA CAAGACCGTGCGCAAAACAGACCACCCACCGGGAC CCAAACCCTGCGACTGTCCCAAATGCCCACCCCCTG AGATGCTTGGAGGACCGTCCATCTTCATCTTCCCCC CAAAACCCAAGGACACCCTCTCGATTTCCCGGACGC CCGAGGTCACATGCTTGGTGGTGGACTTGGGCCCAG ATGACTCCGATGTCCAGATCACATGGTTTGTGGATAA CACCCAGGTGTACACAGCCAAGACGAGTCCGCGTGA GGAGCAGTTCAACAGCACCTACCGTGTGGTCAGTGT CCTCCCCATCCTACACCAGGACTGGCTCAAGGGGAA GGAGTTCAAGTGCAAGGTCAACAGCAAATCCCTCCC CTCCCCCATCGAGAGGACCATCTCCAAGGCCAAAGG ACAGCCCCACGAGCCCCAGGTGTACGTCCTGCCTCC AGCCCAGGAGGAGCTCAGCAGGAACAAAGTCAGTGT GACCTGCCTGATCAAATCCTTCCACCCGCCTGACATT GCCGTCGAGTGGGAGATCACCGGACAGCCGGAGCC AGAGAACAACTACCGGACGACCCCGCCCCAGCTGG ACAGCGACGGGACCTACTTCGTGTACAGCAAGCTCT CGGTGGACAGGTCCCACTGGCAGAGGGGAAACACC TACACCTGCTCGGTGTCACACGAAGCTCTGCACAGC CACCACACAGAAATCCCTCACCCAGTCTCCGGGT AAA |
| 64 | Amino acid sequence for feline lambda chain | GQPKSAPSVTLFPPSNEELSANKATLVCLISDFYPSGLT VAWKADGTPITQGVETTKPSKQSNNKYAASSYLSLSPN EWKSRSRFTCQVTHEGSTVEKNVVPAECS |
| 65 | Nucleotide sequence for feline lambda chain | GGCCAGCCCAAGAGCGCTCCCTCCGTGACCCTGTTC CCCCCAAGCAACGAGGAACTGAGCGCCAACAAGGC CACCCTGGTGTGCCTGATCAGCGACTTCTACCCCAG CGGCCTGACCGTGGCCTGGAAGGCCGATGGCACCC CTATCACCCAGGGCGTGGAAACCACCAAGCCCAGCA AGCAGAGCAACAACAAATACGCCGCCAGCAGCTACC TGAGCCTGAGCCCCAACGAGTGGAAGTCCCGGTCC CGGTTCACATGCCAGGTGACACACGAGGGCAGCAC CGTGGAAAAGAACGTGGTGCCCGCCGAGTGCAGC |

BRIEF DESCRIPTION OF THE SEQUENCES

| SEQ ID NO. | DESCRIPTION | SEQUENCE |
|---|---|---|
| 66 | Amino Acid sequence for human Nerve Growth Factor (Genbank Accession No. AAL05874) | MSMLFYTLITAFLIGIQAEPHSESNVPAGHTIPQAHWTKL QHSLDTALRRARSAPAAAIAARVAGQTRNITVDPRLFKK RRLRSPRVLFSTQPPREAADTQDLDFEVGGAAPFNRT HRSKRSSSHPIFHRGEFSVCDSVSVWVGDKTTATDIKG KEVMVLGEVSINNSVFKQYFFETKCRDPNPVDSGCRGI DSKHWNSCTTTHTFVKALTMDGKQAAWRFIRIDTACM CVLSRKAVRRA |
| 67 | Amino acid sequence for can9L12VH_X92218 | EVQLVESGGGLVQPGGSLRLSCAASGFTFSSHGMSW VRQAPGKGLEWVSVINSGGSSTYYADSVKGRFTISRDN SKNTLYLQMNSLRAEDTAVYYCAKESVGGWEQLVGPH FDYWGQGTLVIVSS |
| 68 | Nucleotide sequence for can9L12VH_X92218 | GAAGTGCAGCTGGTGGAAAGCGGCGGCGGCCTGGT GCAGCCGGGCGGCAGCCTGCGCCTGAGCTGCGCG GCGAGCGGCTTTACCTTTAGCAGCCATGGCATGAGC TGGGTGCGCCAGGCGCCGGGCAAAGGCCTGGAATG GGTGAGCGTGATTAACAGCGGCGGCAGCAGCACCT ATTATGCGGATAGCGTGAAAGGCCGCTTTACCATTAG CCGCGATAACAGCAAAAACACCCTGTATCTGCAGAT GAACAGCCTGCGCGCGGAAGATACCGCGGTGTATTA TTGCGCGAAAGAAAGCGTGGGCGGCTGGGAACAGC TGGTGGGCCCGCATTTTGATTATTGGGGCCAGGGCA CCCTGGTGATTGTCTCGAGC |
| 69 | Amino acid sequence for can9L12VH_HM855939 | QVQLVESGGGVVQPGGSLRLSCAASGFTFSSHGMHW VRQAPGKGLEWVSVINSGGSSTYYADSVKGRFTISRDN SKNTLYLQMNSLRAEDTAVYYCAKESVGGWEQLVGPH FDYWGQGTLVIVSS |
| 70 | Nucleotide sequence for can9L12VH_HM855939 | CAGGTGCAGCTGGTGGAAAGCGGCGGCGGCGTGGT GCAGCCGGGCGGCAGCCTGCGCCTGAGCTGCGCG GCGAGCGGCTTTACCTTTAGCAGCCATGGCATGCAT TGGGTGCGCCAGGCGCCGGGCAAAGGCCTGGAATG GGTGAGCGTGATTAACAGCGGCGGCAGCAGCACCT ATTATGCGGATAGCGTGAAAGGCCGCTTTACCATTAG CCGCGATAACAGCAAAAACACCCTGTATCTGCAGAT GAACAGCCTGCGCGCGGAAGATACCGCGGTGTATTA TTGCGCGAAAGAAAGCGTGGGCGGCTGGGAACAGC TGGTGGGCCCGCATTTTGATTATTGGGGCCAGGGCA CCCTGGTGATTGTCTCGAGC |
| 71 | Amino acid for sequence can9L12VL_M94116 | QSVLTQPPSVSGAPGQRVTISCTGSTNNIGILGVHWYQ QLPGTAPKLLIYGNGNRPSGVPDRFSGSKSGTSASLAIT GLQAEDEADYYCQSFDTTLGAHVFGGGTHLTVL |
| 72 | Nucleotide sequence for can9L12VL_M94116 | CAGAGCGTGCTGACCCAGCCGCCGAGCGTGAGCGG CGCGCCGGGCCAGCGCGTGACCATTAGCTGCACCG GCAGCACCAACAACATTGGCATTCTGGGCGTGCATT GGTATCAGCAGCTGCCGGGCACCGCGCCGAAACTG CTGATTTATGGCAACGGCAACCGCCCGAGCGGCGTG CCGGATCGCTTTAGCGGCAGCAAAAGCGGCACCAG CGCGAGCCTGGCGATTACCGGCCTGCAGGCGGAAG ATGAAGCGGATTATTATTGCCAGAGCTTTGATACCAC CCTGGGCGCGCATGTGTTTGGCGGCGGCACCCATC TGACCGTGCTG |
| 73 | Amino acid sequence for can9L12VL_M94116_65698 | QSVLTQPTSVSGAPGQRVTISCTGSTNNIGILGVHWYQ QLPGTAPKLLIYGNGNRPSGVPDRFSGADSGDSVSLAI TGLQAEDEADYYCQSFDTTLGAHVFGGGTHLTVL |
| 74 | Nucleotide sequence for can9L12VL_M94116_65698 | CAGAGCGTGCTGACCCAGCCGACCAGCGTGAGCGG CGCGCCGGGCCAGCGCGTGACCATTAGCTGCACCG GCAGCACCAACAACATTGGCATTCTGGGCGTGCATT GGTATCAGCAGCTGCCGGGCACCGCGCCGAAACTG CTGATTTATGGCAACGGCAACCGCCCGAGCGGCGTG CCGGATCGCTTTAGCGGCGCGGATAGCGGCGATAG CGTGAGCCTGGCGATTACCGGCCTGCAGGCGGAAG ATGAAGCGGATTATTATTGCCAGAGCTTTGATACCAC CCTGGGCGCGCATGTGTTTGGCGGCGGCACCCATC TGACCGTGCTG |

BRIEF DESCRIPTION OF THE SEQUENCES

| SEQ ID NO. | DESCRIPTION | SEQUENCE |
|---|---|---|
| 75 | Amino acid for sequence can48L2VH_HM855336.1 | EVQLVESGGGLVQPGGSLRLSCAASGFTFSTYGMNWV RQAPGKGLEWVSYISSGGSSIYYADSVKGRFTISRDNA KNSLYLQMNSLRAEDTAVYYCAGSRYTYAYGGGYEFH FWGQGTLVTVSS |
| 76 | Nucleotide sequence for can48L2VH_HM855336.1 | GAAGTGCAGCTGGTGGAAAGCGGCGGCGGCCTGGT GCAGCCGGGCGGCAGCCTGCGCCTGAGCTGCGCG GCGAGCGGCTTTACCTTTAGCACCTATGGCATGAAC TGGGTGCGCCAGGCGCCGGGCAAAGGCCTGGAATG GGTGAGCTATATTAGCAGCGGCGGCAGCAGCATTTA TTATGCGGATAGCGTGAAAGGCCGCTTTACCATTAG CCGCGATAACGCGAAAAACAGCCTGTATCTGCAGAT GAACAGCCTGCGCGCGGAAGATACCGCGGTGTATTA TTGCGCGGGCAGCCGCTATACCTATGCGTATGGCGG CGGCTATGAATTTCATTTTTGGGGCCAGGGCACCCT GGTGATTGTCTCGAGC |
| 77 | Amino acid sequence for can48L2VH_HM855336.1_E46Q | EVQLVESGGGLVQPGGSLRLSCAASGFTFSTYGMNWV RQAPGKGLQWVSYISSGGSSIYYADSVKGRFTISRDNA KNSLYLQMNSLRAEDTAVYYCAGSRYTYAYGGGYEFH FWGQGTLVTVSS |
| 78 | Nucleotide sequence for can48L2VH_HM855336.1_E46Q | GAAGTGCAGCTGGTGGAAAGCGGCGGCGGCCTGGT GCAGCCGGGCGGCAGCCTGCGCCTGAGCTGCGCG GCGAGCGGCTTTACCTTTAGCACCTATGGCATGAAC TGGGTGCGCCAGGCGCCGGGCAAAGGCCTGCAGTG GGTGAGCTATATTAGCAGCGGCGGCAGCAGCATTTA TTATGCGGATAGCGTGAAAGGCCGCTTTACCATTAG CCGCGATAACGCGAAAAACAGCCTGTATCTGCAGAT GAACAGCCTGCGCGCGGAAGATACCGCGGTGTATTA TTGCGCGGGCAGCCGCTATACCTATGCGTATGGCGG CGGCTATGAATTTCATTTTTGGGGCCAGGGCACCCT GGTGATTGTCTCGAGC |
| 79 | Amino acid sequence for can48L2VH_HM855323.1 | EVQLVESGGGLVKPGGSLRLSCAASGFTFSTYGINWV RQAPGKGLEWVSYISSGGSSTYYADSVKGRFTISRDNA KNSLYLQMNSLRAEDTAVYYCAGSRYTYAYGGGYEFH FWGQGTLVTVSS |
| 80 | Nucleotide sequence for can48L2VH_HM855323.1 | GAAGTGCAGCTGGTGGAAAGCGGCGGCGGCCTGGT GAAACCGGGCGGCAGCCTGCGCCTGAGCTGCGCGG CGAGCGGCTTTACCTTTAGCACCTATGGCATTAACTG GGTGCGCCAGGCGCCGGGCAAAGGCCTGGAATGGG TGAGCTATATTAGCAGCGGCGGCAGCAGCACCTATT ATGCGGATAGCGTGAAAGGCCGCTTTACCATTAGCC GCGATAACGCGAAAAACAGCCTGTATCTGCAGATGA ACAGCCTGCGCGCGGAAGATACCGCGGTGTATTATT GCGCGGGCAGCCGCTATACCTATGCGTATGGCGGC GGCTATGAATTTCATTTTTGGGGCCAGGGCACCCTG GTGATTGTCTCGAGC |
| 81 | Amino acid sequence for can48L2VH_HM855323.1_E46Q | EVQLVESGGGLVKPGGSLRLSCAASGFTFSTYGINWV RQAPGKGLQWVSYISSGGSSTYYADSVKGRFTISRDN AKNSLYLQMNSLRAEDTAVYYCAGSRYTYAYGGGYEF HFWGQGTLVTVSS |
| 82 | Nucleotide sequence for can48L2VH_HM855323.1_E46Q | GAAGTGCAGCTGGTGGAAAGCGGCGGCGGCCTGGT GAAACCGGGCGGCAGCCTGCGCCTGAGCTGCGCGG CGAGCGGCTTTACCTTTAGCACCTATGGCATTAACTG GGTGCGCCAGGCGCCGGGCAAAGGCCTGCAGTGGG TGAGCTATATTAGCAGCGGCGGCAGCAGCACCTATT ATGCGGATAGCGTGAAAGGCCGCTTTACCATTAGCC GCGATAACGCGAAAAACAGCCTGTATCTGCAGATGA ACAGCCTGCGCGCGGAAGATACCGCGGTGTATTATT GCGCGGGCAGCCGCTATACCTATGCGTATGGCGGC GGCTATGAATTTCATTTTTGGGGCCAGGGCACCCTG GTGATTGTCTCGAGC |
| 83 | Amino acid sequence for can48L2VL_Z73654.1_P8A | QSVLTQPASASGTPGQRVTISCSGSTMDIDIFGVNWYQ QLPGTAPKLLIYSDGDRPSGVPDRFSGSKSGTSASLAIS GLQSEDEADYHCQSGDSTLGALAIFGGGTHVTV |

BRIEF DESCRIPTION OF THE SEQUENCES

| SEQ ID NO. | DESCRIPTION | SEQUENCE |
|---|---|---|
| 84 | Nucleotide sequence for can48L2VL_Z73654.1_P8A | CAGAGCGTGCTGACCCAGCCGGCGAGCGCGAGCGG CACCCCGGGCCAGCGCGTGACCATTAGCTGCAGCG GCAGCACCATGGATATTGATATTTTTGGCGTGAACTG GTATCAGCAGCTGCCGGGCACCGCGCCGAAACTGC TGATTTATAGCGATGGCGATCGCCCGAGCGGCGTGC CGGATCGCTTTAGCGGCAGCAAAAGCGGCACCAGC GCGAGCCTGGCGATTAGCGGCCTGCAGAGCGAAGA TGAAGCGGATTATCATTGCCAGAGCGGCGATAGCAC CCTGGGCGCGCTGGCGATTTTTGGCGGCGGCACCC ATGTGACCGTGCTG |
| 85 | Amino acid sequence for can48L2VL_Z73654.1_P14L | QSVLTQPPSASGTLGQRVTISCSGSTMDIDIFGVNWYQ QLPGTAPKLLIYSDGDRPSGVPDRFSGSKSGTSASLAIS GLQSEDEADYHCQSGDSTLGALAIFGGGTHVTVL |
| 86 | Nucleotide sequence for can48L2VL_Z73654.1_P14L | CAGAGCGTGCTGACCCAGCCGCCGAGCGCGAGCGG CACCCTGGGCCAGCGCGTGACCATTAGCTGCAGCG GCAGCACCATGGATATTGATATTTTTGGCGTGAACTG GTATCAGCAGCTGCCGGGCACCGCGCCGAAACTGC TGATTTATAGCGATGGCGATCGCCCGAGCGGCGTGC CGGATCGCTTTAGCGGCAGCAAAAGCGGCACCAGC GCGAGCCTGGCGATTAGCGGCCTGCAGAGCGAAGA TGAAGCGGATTATCATTGCCAGAGCGGCGATAGCAC CCTGGGCGCGCTGGCGATTTTTGGCGGCGGCACCC ATGTGACCGTGCTG |
| 87 | Amino acid sequence for can48L2VL_Z22192.1_P8A | QSVVTQPASVSGAPGQRVTISCTGSTMDIDIFGVSWYQ QLPGTAPKLLIYGDGDRPSGVPDRFSGSKSGASASLAI TGLQAEDEADYHCQSGDSTLGALAIFGGGTHVTVL |
| 88 | Nucleotide sequence for can48L2VL_Z22192.1_P8A | CAGAGCGTGGTGACCCAGCCGGCGAGCGTGAGCGG CGCGCCGGGCCAGCGCGTGACCATTAGCTGCACCG GCAGCACCATGGATATTGATATTTTTGGCGTGAGCTG GTATCAGCAGCTGCCGGGCACCGCGCCGAAACTGC TGATTTATGGCGATGGCGATCGCCCGAGCGGCGTGC CGGATCGCTTTAGCGGCAGCAAAAGCGGCGCGAGC GCGAGCCTGGCGATTACCGGCCTGCAGGCGGAAGA TGAAGCGGATTATCATTGCCAGAGCGGCGATAGCAC CCTGGGCGCGCTGGCGATTTTTGGCGGCGGCACCC ATGTGACCGTGCTG |
| 89 | Amino acid sequence for can48L2VL_Z22192.1_P14L | QSVVTQPPSVSGALGQRVTISCTGSTMDIDIFGVSWYQ QLPGTAPKLLIYGDGDRPSGVPDRFSGSKSGASASLAI TGLQAEDEADYHCQSGDSTLGALAIFGGGTHVTVL |
| 90 | Nucleotide sequence for can48L2VL_Z22192.1_P14L | CAGAGCGTGGTGACCCAGCCGCCGAGCGTGAGCGG CGCGCTGGGCCAGCGCGTGACCATTAGCTGCACCG GCAGCACCATGGATATTGATATTTTTGGCGTGAGCTG GTATCAGCAGCTGCCGGGCACCGCGCCGAAACTGC TGATTTATGGCGATGGCGATCGCCCGAGCGGCGTGC CGGATCGCTTTAGCGGCAGCAAAAGCGGCGCGAGC GCGAGCCTGGCGATTACCGGCCTGCAGGCGGAAGA TGAAGCGGATTATCATTGCCAGAGCGGCGATAGCAC CCTGGGCGCGCTGGCGATTTTTGGCGGCGGCACCC ATGTGACCGTGCTG |
| 91 | Amino acid sequence for can48L2VL_Z22192.1 | QSVVTQPPSVSGAPGQRVTISCTGSTMDIDIFGVSWYQ QLPGTAPKLLIYGDGDRPSGVPDRFSGSKSGASASLAI TGLQAEDEADYHCQSGDSTLGALAIFGGGTHVTVL |
| 92 | Nucleotide sequence for can48L2VL_Z22192.1 | CAGAGCGTGGTGACCCAGCCGCCGAGCGTGAGCGG CGCGCCGGGCCAGCGCGTGACCATTAGCTGCACCG GCAGCACCATGGATATTGATATTTTTGGCGTGAGCTG GTATCAGCAGCTGCCGGGCACCGCGCCGAAACTGC TGATTTATGGCGATGGCGATCGCCCGAGCGGCGTGC CGGATCGCTTTAGCGGCAGCAAAAGCGGCGCGAGC GCGAGCCTGGCGATTACCGGCCTGCAGGCGGAAGA TGAAGCGGATTATCATTGCCAGAGCGGCGATAGCAC CCTGGGCGCGCTGGCGATTTTTGGCGGCGGCACCC ATGTGACCGTGCTG |

DETAILED DESCRIPTION OF THE INVENTION

The invention disclosed herein provides anti-NGF antigen binding proteins that bind NGF with high affinity. The invention further provides antigen binding proteins and polypeptides that also bind to NGF that are variants of said antigen binding proteins as well as methods of making and using these antigen binding proteins. In some embodiments, the invention also provides polynucleotides encoding said antigen binding proteins and/or polypeptide. The invention disclosed herein also provides methods for preventing and/or treating pain by administration of a therapeutically effective amount of the anti-NGF antigen binding proteins of the invention.

General Techniques

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Unless otherwise defined, scientific and technical terms used in connection with the antigen binding proteins described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art and are not limited to a single description. It is well known in the art that different techniques may be substituted for what is described.

All patents and other publications identified are expressly incorporated herein by reference for the purpose of describing and disclosing, for example, the methodologies described in such publications that might be used in connection with the present invention. These publications are provided solely for their disclosure prior to the filing date of the present application Standard techniques are used for recombinant DNA, oligonucleotide synthesis, and tissue culture and transfection (ex. electroporation, lipofection). Enzymatic reactions and purification techniques are performed per manufacturer's specifications or as commonly accomplished in the art or as described herein. The foregoing techniques and procedures are generally performed according to conventional methods well known in the art and as described, but not limited to the various general and more specific references that are cited and discussed throughout the present specification, See ex. Sambrook et al. MOLECULAR CLONING: LAB. MANUAL ($3^{rd}$ ed., Cold Spring Harbor Lab. Press, Cold Spring Harbor, N.Y., 2001) and Ausubel et al. Current Protocols in Molecular Biology (New York: Greene Publishing Association J Wiley Interscience), Oligonucleotide Synthesis (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. 1. Freshney, ed. 1987); *Introduction to Cell and Tissue Culture* (1. P. Mather and P. E. Roberts, 1998) Plenum Press; *Cell and Tissue Culture: Laboratory Procedures* (A. Doyle, J. B. Griffiths, and D. G. Newell, eds., 1993-1998) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (E. Coligan et al., eds., 1991); *Short Protocols in Molecular Biology* (Wiley and Sons, 1999); *Immunobiology* (C. A. Janeway and P. Travers, 1997); Antibodies (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (Y. T. DeVita et al., eds., J.B. Lippincott Company, 1993).

Other than in the operating examples, or where otherwise indicated, all numbers expressing quantities of ingredients or reaction conditions used herein should be understood as modified in all instances by the term "about."

Definitions

Before describing the present invention in detail, several terms used in the context of the present invention will be defined. In addition to these terms, others are defined elsewhere in the specification as necessary. Unless otherwise expressly defined herein, terms of art used in this specification will have their art-recognized meanings.

As used in the specification and claims, the singular form "a", "an" and "the" includes plural references unless the context clearly dictates otherwise. For example, reference to "an antibody" includes a plurality of such antibodies.

As used herein, the term "comprising" is intended to mean that the compositions and methods include the recited elements, but not excluding others.

As used herein, the term "nerve growth factor" and "NGF" refers to nerve growth factor and variants thereof that retain at least part of the biological activity of NGF.

"NGF receptor" refers to a polypeptide that is bound by or activated by NGF. NGF receptors include the TrkA receptor and to a lesser extent the p75 receptor of canines.

"Biological activity" of NGF generally refers to the ability to bind NGF receptors and/or activate NGF receptor signaling pathways. Without limitation, a biological activity includes anyone or more of the following: the ability to bind an NGF receptor (such as TrkA and/or p75); the ability to promote TrkA receptor dimerization and/or autophosphorylation; the ability to activate an NGF receptor signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage; the ability to promote survival of mouse E13.5 trigeminal neurons; and the ability to mediate pain, including post-surgical pain.

As used herein, an "anti-NGF antigen binding protein" (interchangeably termed "anti-NGF antibody" and "anti-NGF antagonist antibody" "antigen binding fragment" "antigen binding portion" and the like) refers to an antigen binding protein which is able to bind to NGF and inhibit NGF biological activity and/or downstream pathway(s) mediated by NGF signaling. An anti-NGF antigen binding protein encompass binding proteins and antibodies that block, antagonize, suppress or reduce (including significantly) NGF biological activity, including downstream pathways mediated by NGF signaling and/or inhibit NGF from binding to its receptor trkA, such as receptor binding and/or elicitation of a cellular response to NGF. For purpose of the present invention, it will be explicitly understood that the term "anti-NGF antigen binding protein" or "anti-NGF-antagonist antibody" encompass all the previously identified terms, titles, and functional states and characteristics whereby the NGF itself, an NGF biological activity (including but not limited to its ability to ability to mediate any aspect of osteoarthritis pain, inflammatory pain, post-surgical pain, cancer pain and the like), or the consequences of the biological activity, are substantially nullified, decreased, or neutralized in any meaningful degree. In some embodiments, an anti-NGF antagonist antibody binds NGF and prevent NGF dimerization and/or binding to an NGF receptor (such as TrkA and/or p75). In other embodiments, an anti-NGF antigen binding protein binds to NGF and prevents TrkA receptor dimerization and/or TrkA autophosphorylation. Examples of anti-NGF antagonist antibodies are provided herein.

As used herein, the term "antigen binding protein", "antibody" "antigen binding protein" and the like, which may be used interchangeably, refers to a polypeptide, or fragment thereof, comprising an antigen binding site. In one embodiment of the present invention the antigen binding protein of the invention further provides an immunoglobulin capable of specific binding to a target, such as a carbohydrate, polynucleotide, lipid, polypeptide, etc., through at least one antigen recognition site located in one or more variable regions of the immunoglobulin molecule. In some embodiments, an antibody has two light and two heavy chains. Thus, an isolated intact antibody may be an isolated from a pool of polyclonal antibodies, a monoclonal antibody, a synthetic antibody, a recombinant antibody, a chimeric antibody, a heterochimeric antibody or an antibody that is considered to be speciated, as defined herein. In some embodiments, the term "antigen binding protein" "antibody" "antagonist antibody" and the like preferably refers to monoclonal antibodies and fragments thereof, and immunologic binding equivalents thereof that can bind to the NGF protein and fragments thereof. As used herein, the term encompasses not only full length (by standard definition meaning two heavy and two light chains) polyclonal or monoclonal antibodies, but also fragments thereof. For the purposes of the present invention, "antibody" and "antigen binding protein" also includes antibody fragments, unless otherwise stated. Exemplary antibody fragments include Fab, Fab', F(ab')2, Fv, scFv, Fd, dAb, diabodies, their antigen-recognizing fragments, small modular immunopharmaceuticals (SMIPs) nanobodies, IgNAR molecules and the equivalents that are recognized by one of skill in the art to be an antigen binding protein or antibody fragment and any of above mentioned fragments and their chemically or genetically manipulated counterparts, as well as other antibody fragments and mutants thereof, fusion proteins comprising an antibody portion, and any other modified configuration of the immunoglobulin molecule that comprises an antigen recognition site. Antibodies and antigen binding proteins can be made, for example, via traditional hybridoma techniques (Kohler et al., Nature 256:495-499 (1975)), recombinant DNA methods (U.S. Pat. No. 4,816,567), or phage display techniques using antibody libraries (Clackson et al., Nature 352:624-628 (1991); Marks et al., J. Mol. Biol. 222:581-597 (1991)). For various other antibody production techniques, see Antibodies: A Laboratory Manual, eds. Harlow et al., Cold Spring Harbor Laboratory, 1988 as well as other techniques that are well known to those skilled in the art.

A "monoclonal antibody" as defined herein is an antibody produced by a single clone of cells (specifically, a single clone of hybridoma cells) and therefore a single pure homogeneous type of antibody. All monoclonal antibodies produced from the same clone are identical and have the same antigen specificity. Monoclonal antibodies are a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (Fab, Fab', F(ab')2, Fv, scFv, Fd, dAb, diabodies, their antigen-recognizing fragments, small modular immunopharmaceuticals (SMIPs) nanobodies, IgNAR molecules and the like), mutants thereof, fusion proteins comprising an antibody portion, and any other modified configuration of the immunoglobulin molecule that comprises an antigen recognition site of the required specificity and the ability to bind to an antigen. It is not intended to be limited to the source of the antibody or the manner in which it is made (ex. by hybridoma, phage selection, recombinant expression, transgenic animals, etc.).

Figure 2:
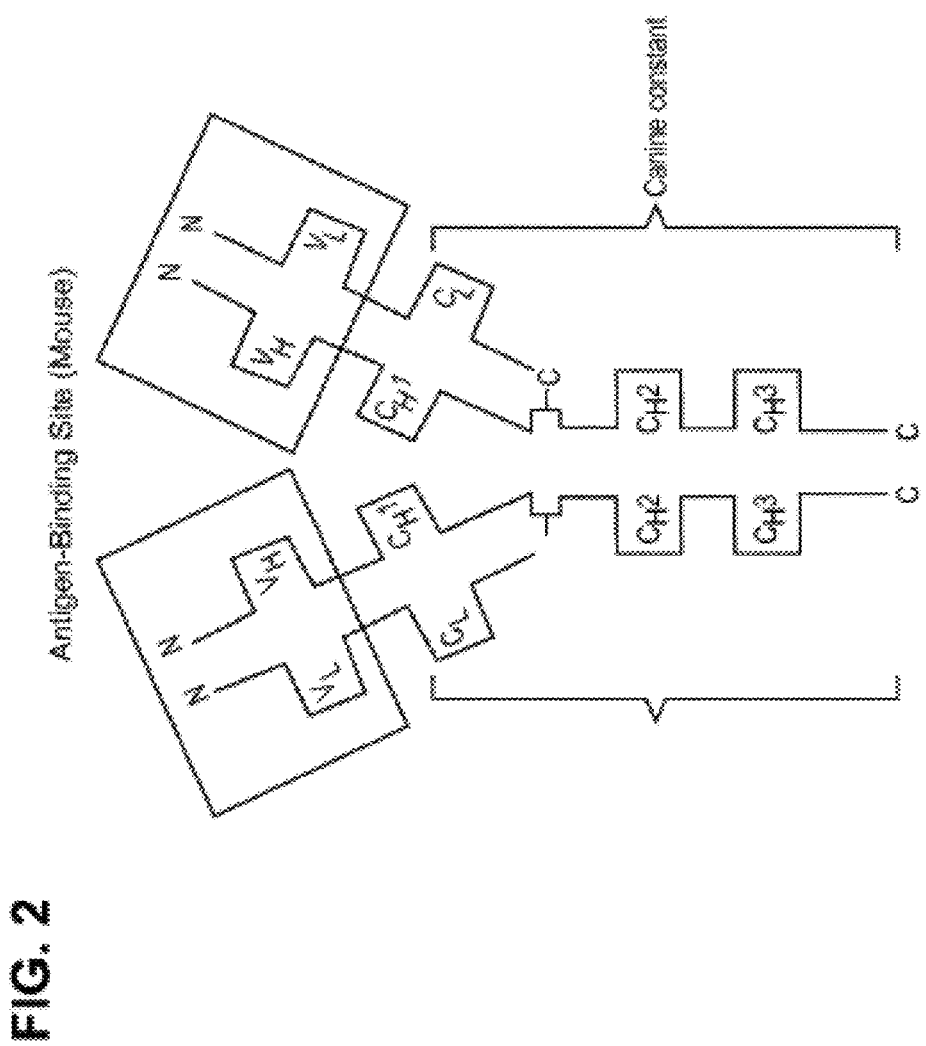
FIG. 2: is a schematic representation of the general structure of a mouse/canine chimeric IgG.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, typically by genetic engineering, from antibody variable and constant region genes belonging to different species. For example, the variable segments of the genes from a mouse monoclonal antibody may be joined to canine constant segments. FIG. 2 is a schematic representation of the general structure of one embodiment of a mouse: canine IgG. In this embodiment, the antigen binding site is derived from mouse while the Fc portion is canine.

Figure 4:
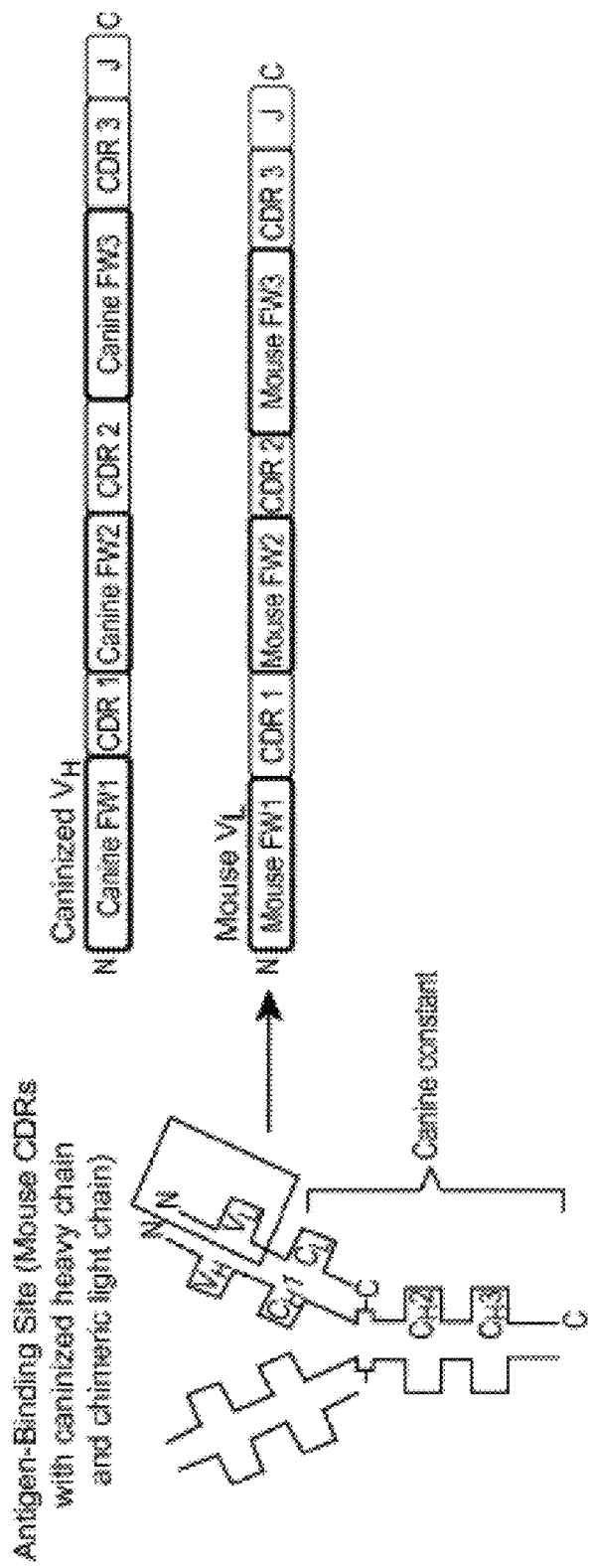
FIG. 4 is an illustration of a "heterochimeric" monoclonal antibody paring the chimeric light chain with a fully caninized heavy chain.
Figure 5:
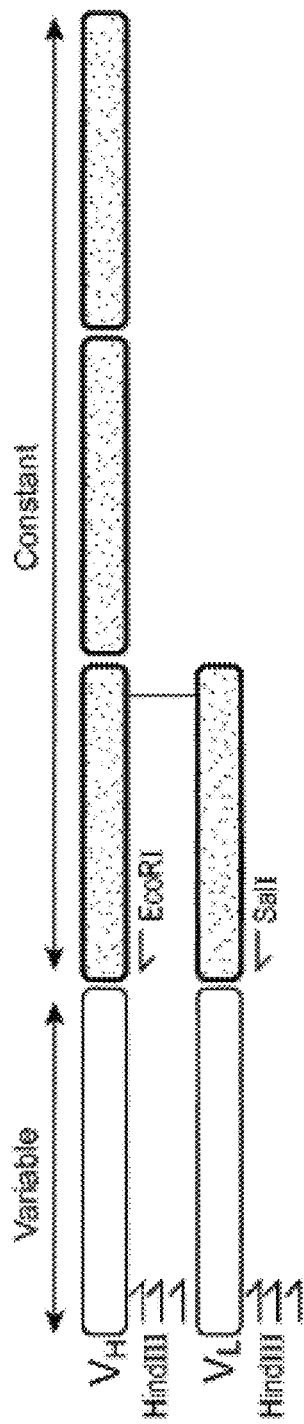
FIG. 5 is an illustration of antibody variable chains showing primers to constant regions and degenerate primers directed at mouse variable regions.

The term "heterochimeric" as defined herein, refers to an antibody in which one of the antibody chains (heavy or light) is caninized while the other is chimeric. FIG. 4 depicts one embodiment of a heterochimeric molecule. In this embodiment, a caninized variable heavy chain (where all the CDRs are mouse and all FRs are canine) is paired with a chimeric variable light chain (where all the CDRs are mouse and all FRs are mouse. In this embodiment, both the variable heavy and variable light chains are fused to a canine constant region.

Figure 3:
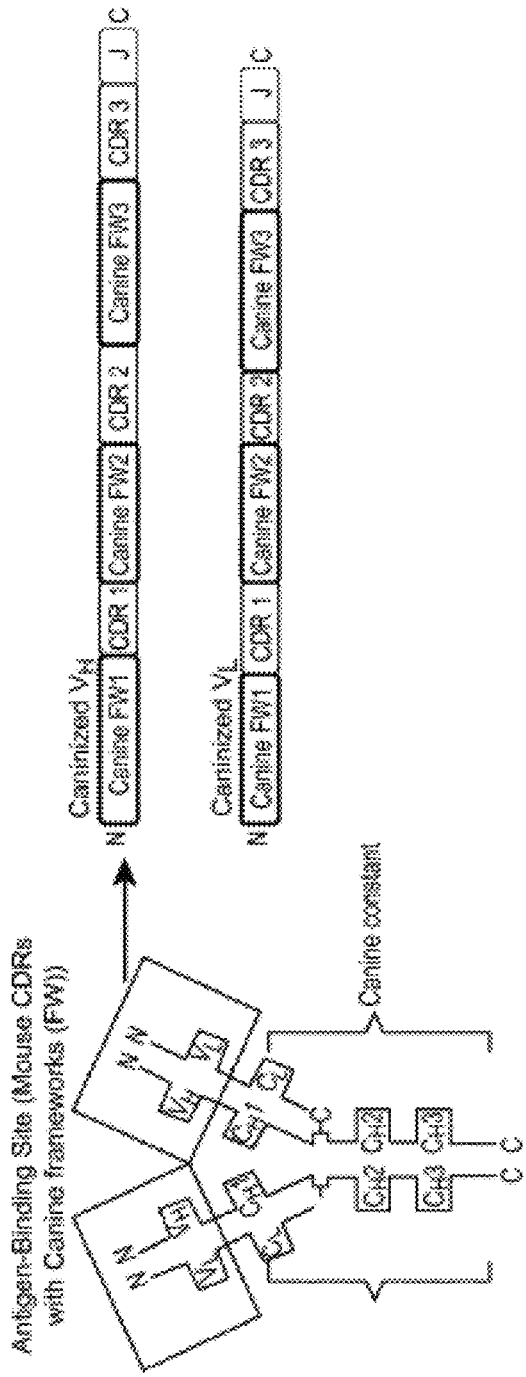
FIG. 3: is an illustration showing speciation or "caninization" of a mouse IgG, mouse CDRs are grafted onto canine frameworks. This figure also represents felinization, equinization, humanization and other speciation, as defined herein.

For the sake of simplicity, the following describes "caninized" antibodies, however the same can be applied to felinized, equinized, humanized or any other "speciated" antigen binding protein. As an example, "Caninization" is defined as a method for transferring non-canine antigen-binding information from a donor antibody to a less immunogenic canine antibody acceptor to generate treatments useful as therapeutics in dogs. Caninized antibodies are canine antibody sequences in which hypervariable region residues of the recipient are replaced by hypervariable region residues from a non-canine species (donor antibody) such as such as mouse, rat, rabbit, cat, dogs, goat, chicken, bovine, horse, llama, camel, dromedaries, sharks, non-human primates, human, humanized, recombinant sequence, or an engineered sequence having the desired properties, specificity, affinity, and capacity. Furthermore, caninized antibodies may include residues that are not found in the recipient antibody or in the donor antibody. These modifications are made to further refine antibody performance. The modifications to the hypervariable regions and/or the framework regions, as described herein, are determined for each separately engineered speciated (caninized) antibody based on experimentation known to those in the art yet cannot be predicted prior to said experimentation. The caninized antibody optionally may comprise a complete, or at least a portion of an immunoglobulin constant region (Fc), typically that of a canine immunoglobulin. FIG. 3 is an illustration of one embodiment showing speciation or caninization of a mouse IgG. All descriptions of caninization of an antigen binding protein and that of a caninized antigen binding protein can be applicable, in concept, to any speciated antibody, whether it is caninization, felinization, equinization, humanization etc.

The phrase "recombinant canine antibody", "recombinant feline antibody", "recombinant equine antibody", "recombinant human antibody" and the like all include speciated antibodies that are prepared, expressed, created or isolated by recombinant means, such as antibodies expressed using a recombinant expression vector transfected into a host cell, antibodies isolated from a recombinant, combinatorial canine (or feline, human etc.) antibody library, antibodies isolated from an animal (ex. a mouse) that is transgenic for canine immunoglobulin genes (see ex. Taylor, L. D., et al. (1992) Nucl. Acids Res. 20:6287-6295) or antibodies prepared, expressed, created or isolated by any other means that involves splicing of canine (or feline, human etc.) immunoglobulin gene sequences to other DNA sequences.

The term "canine antibody", "feline antibody", "equine antibody", "human antibody" and the like, as used herein, refers to an antibody (antigen binding protein) that is generated against a target and antibodies isolated from lymphocytes from within the target species. These antibodies, as described herein, have been recombinantly modified in vitro to include specific constant regions of the target species. Additionally, the antibodies as described herein were identified, isolated, modified to alter the antibody constant region followed by an expression and isolation from in vitro cell culture systems known and used routinely by those of skill in the art.

"Native antibodies" and "native immunoglobulins" are usually heterotetrameric glycoproteins of about 150,000 Daltons, composed of two identical light (l) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. FIG. 1 is an example of the general structure of a native mouse immunoglobulin G (IgG) highlighting the antigen binding site.

The "parent" antibody herein is one that is encoded by an amino acid sequence used for the preparation of the variant. Preferably, the parent antibody has a canine framework region and, if present, has canine antibody constant region(s). For example, the parent antibody may be a caninized or canine antibody.

Depending on the amino acid sequence of the constant domain of the heavy chains of antibodies, immunoglobulins can be assigned to different classes. Presently there are five major classes of immunoglobulins: IgA, IgD, IgE, IgG, and IgM, and several of these may be further divided into subclasses (isotypes), ex. $IgG_1$, $IgG_2$, $IgG_3$, $IgG_4$, IgA, and $IgA_2$ (as defined by mouse and human designation). The heavy-chain constant domains that correspond to the different classes of immunoglobulins are called alpha, delta, epsilon, gamma, and mu, respectively. The subunit structures and three-dimensional configurations of different classes of immunoglobulins are well known in multiple species. The prevalence of individual isotypes and functional activities associated with these constant domains are species-specific and must be experimentally defined.

The "light chains" of antibodies (immunoglobulins) from any vertebrate species can be assigned to one of two clearly distinct types, called kappa (K) and lambda (λ), based on the amino acid sequences of their constant domains.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (I) an approach based on cross-species sequence variability (i.e., Kabat et al. *Sequences of Proteins of Immunological Interest*, (5th ed., 1991, National Institutes of Health, Bethesda Md.)); and (2) an approach based on crystallographic studies of antigen-antibody complexes (Chothia et al. (1989) *Nature* 342:877; A-lazikani et al (1997) *J. Molec. Biol.* 273:927-948)). As used herein, a CDR may refer to CDRs defined by either approach or by a combination of both approaches.

The term "hypervariable region" when used herein refers to the amino acid residues of an antibody which are responsible for antigen binding. The hypervariable region comprises amino acid residues from a "complementarity determining region" or "CDR" (Kabat, et al. (1991), above) and/or those residues from a "hypervariable loop" (Chothia and Lesk J. Mol. Biol. 196:901-917 (1987). "Framework" or "FR" residues are those variable domain residues other than the hypervariable region residues as herein defined.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues.

A "functional Fc region" possesses at least one effector function of a native sequence Fc region. Exemplary "effector functions" include C1q binding; complement dependent cytotoxicity (CDC); Fc receptor binding; neonatal receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" or a "mutated" or "mutant" Fc region comprises an amino acid sequence which differs from that of a native sequence Fc region by virtue of at least one amino acid modification, and may or may not retain at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith. A variant or mutated Fc region may also essentially eliminate the function of the Fc region of the antibody. For example, Fc region mutations may eliminate effector function of the antibody. In one embodiment of the invention the antibody of the invention comprises a mutated Fc region.

As used herein, "Fc receptor" and "FcR" describe a receptor that binds to the Fc region of an antibody. The preferred FcR is a native sequence FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; and de Haas et al., 1995, *J. Lab. Clin. Med.*, 126:330-41. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, for example, in an animal model such as that disclosed in Clynes et al., 1998, PNAS (USA), 95:652-656.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab') 2 antibody fragments originally were produced as pairs of Fab' fragments which have hinge cysteines between them. Other chemical couplings of antibody fragments are also known.

"Fv' is the minimum antibody fragment that contains a complete antigen-recognition and binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

An "antigen", as used herein, refers to the antigenic determinant recognized by the CDRs of the antigen binding protein or antibody as described herein. In other words, epitope refers to that portion of any molecule capable of being recognized by, and bound by, an antibody. Unless indicated otherwise, the term "epitope" as used herein, refers to the region of NGF to which an anti-NGF antigen binding protein/antibody/agent binds.

The term "antigen binding domain," "active fragments of an antibody" or the like refers to the part of an antibody or antigen binding protein that comprises the area specifically binding to or complementary to a part or all of an antigen. Where an antigen is large, an antibody may only bind to a particular part of the antigen. The "epitope," "active fragments of an epitope," or "antigenic determinant" or the like is a portion of an antigen molecule that is responsible for specific interactions with the antigen binding domain of an antibody. An antigen binding domain may be provided by one or more antibody variable domains (for example a so-called Fd antibody fragment consisting of a VH domain). An antigen binding domain may comprise an antibody light chain variable domain (VL) and an antibody heavy chain variable domain (VH) (U.S. Pat. No. 5,565,332).

The terms "binding portion" of an antibody (or "antibody portion") or antigen-binding polypeptide or the like includes one or more complete domains, for example, a pair of complete domains, as well as fragments of an antibody that retain the ability to specifically bind to an antigen, for example, NGF. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab') 2, F(abc), Fd, dAb, Fv, single chains, single-chain antibodies, for example, scFv, and single domain antibodies (Muyldermans et al., 2001, 26:230-5), and an isolated complementarity determining region (CDR). Fab fragment is a monovalent fragment consisting of the VL, VH, CL and CH1 domains. F(ab')2 fragment is a bivalent fragment comprising two Fab fragments linked by a disulfide bridge at the hinge region. Fd fragment consists of the VH and CH1 domains, and Fv fragment consists of the VL and VH domains of a single arm of an antibody. A dAb fragment consists of a VH domain (Ward et al., (1989) Nature 341:544-546). While the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv) (Bird et al., 1988, Science 242:423-426). Such single chain antibodies are also intended to be encompassed within the term "binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see for example, Holliger, et al., 1993, *Proc. Natl. Acad. Sci. USA* 90:6444-6448). An antibody or binding portion thereof also may be part of a larger immunoadhesion molecules formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Binding fragments such as Fab and F(ab') 2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein and as known in the art. Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. A bispecific antibody can also include two antigen binding regions with an intervening constant region. Bispecific antibodies can be produced by a variety of methods including fusion of hybridomas or linking of Fab' fragments. See, for example, Songsivilai et al., Clin. Exp. Immunol. 79:315-321, 1990; Kostelny et al., 1992, J. Immunol. 148, 1547-1553.

The term "backmutation" refers to a process in which some or all of the somatically mutated amino acids of a canine antibody are replaced with the corresponding germline residues from a homologous germline antibody sequence. The heavy and light chain sequences of the canine antibody of the invention are aligned separately with the germline sequences to identify the sequences with the highest homology. Differences in the canine antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the canine antibody should not be included in the final canine antibody; as an example, activity enhancing amino acids identified by the selective mutagenesis approach will not be subject to backmutation. To minimize the number of amino acids subject to backmutation those amino acid positions found to be different from the closest germline sequence but identical to the corresponding amino acid in a second germline sequence can remain, provided that the second germline sequence is identical and co-linear to the sequence of the canine antibody of the invention. Back mutation of selected target framework residues to the corresponding donor residues might be required to restore and or improved affinity.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins). An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an NGF epitope is an antibody that binds this epitope with greater affinity, avidity, more readily, and/or with greater duration than it binds to other NGF epitopes or non-NGF epitopes. It is also understood by reading this definition that, for example, an antibody (or moiety or epitope) that specifically or preferentially binds to a first target mayor may not specifically or preferentially bind to a second target. As such, "specific binding" or "preferential binding" does not necessarily require (although it can include) exclusive binding. Generally, but not necessarily, reference to binding means preferential binding.

The term "specifically" in the context of antibody binding, refers to high avidity and/or high affinity binding of an antibody to a specific antigen, i.e., a polypeptide, or epitope. Antibody specifically binding an antigen is stronger than binding of the same antibody to other antigens. Antibodies which bind specifically to a polypeptide may be capable of binding other polypeptides at a weak, yet detectable level (for example, 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a $K_d$ of $10^{-7}$ M or less, $10^{-8}$ M or less $10^{-9}$ M or less, $10^{-10}$ M or less, $10^{-11}$ M or less, $10^{-12}$ M or less, or $10^{-13}$ M or less etc.

As used herein, the term "affinity" refers to the strength of the binding of a single antigen-combining site with an antigenic determinant. Affinity depends on the closeness of stereochemical fit between antibody or antigen binding protein combining sites and antigen determinants, on the size of the area of contact between them, on the distribution of charged and hydrophobic groups, etc. Antibody affinity can be measured by equilibrium analysis or by the Surface Plasmon Resonance "SPR" method (for example BIA-CORE™) The SPR method relies on the phenomenon of surface plasmon resonance (SPR), which occurs when surface plasmon waves are excited at a metal/liquid interface. Light is directed at, and reflected from, the side of the surface not in contact with sample, and SPR causes a reduction in the reflected light intensity at a specific combination of angle and wavelength. Bimolecular binding events cause changes in the refractive index at the surface layer, which are detected as changes in the SPR signal.

The term "$K_D$", as used herein, is intended to refer to the dissociation constant of an antibody-antigen interaction. The dissociation constant, $K_D$, and the association constant, $K_a$, are quantitative measures of affinity. At equilibrium, free antigen (Ag) and free antibody (Ab) are in equilibrium with antigen-antibody complex (Ag-Ab), and the rate constants, $k_a$ and $k_d$, quantitate the rates of the individual reactions. At equilibrium, ka [Ab][Ag]=kd [Ag-Ab]. The dissociation constant, $K_d$, is given by: Kd=kd/ka=[Ag][Ab]/[Ag–Ab]. $K_D$ has units of concentration, most typically M, mM, µM, nM, pM, etc. When comparing antibody affinities expressed as $K_D$, having greater affinity for NGF is indicated by a lower value. The association constant, $K_a$, is given by: Ka=ka/kd=[Ag–Ab]/[Ag][Ab]. $K_a$ has units of inverse concentration, most typically $M^{-1}$, $mM^{-1}$, $\mu \cdot M^{-1}$, $nM^{-1}$, $pM^{-1}$, etc. As used herein, the term "avidity" refers to the strength of the antigen-antibody bond after formation of reversible complexes. Anti-NGF antibodies may be characterized in terms of the $K_D$ for their binding to a NGF protein, as binding "with a dissociation constant ($K_D$) in the range of from about (lower $K_D$ value) to about (upper $K_D$ value)."

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also, included within the definition are, for example, polypeptides containing one or more analogs of an amino acid (including, for example, un-natural amino acids, etc.), as well as other modifications known in the art. It is understood that, because the polypeptides of this invention are based upon an antibody, the polypeptides can occur as single chains or associated chains.

The term 'conservative amino acid substitution" indicates any amino acid substitution for a given amino acid residue, where the substitute residue is so chemically similar to that of the given residue that no substantial decrease in polypeptide function (for example, enzymatic activity) results. Conservative amino acid substitutions are commonly known in the art and examples thereof are described, ex., in U.S. Pat. Nos. 6,790,639, 6,774,107, 6,194,167, or 5,350,576. In a preferred embodiment, a conservative amino acid substitution will be anyone that occurs within one of the following six groups:

Small aliphatic, substantially non-polar residues: Ala, Gly, Pro, Ser, and Thr;
Large aliphatic, non-polar residues: lie, Leu, and Val; Met;
Polar, negatively charged residues and their amides: Asp and Glu;
Amides of polar, negatively charged residues: Asn and Gin; His;
Polar, positively charged residues: Arg and Lys; His; and
Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gin; His); Asp (Glu); Gin (Asn); Glu (Asp); Gly (Pro); His (Asn; Gln); Ile (Leu; Val); Leu (Ile; Val); Lys (Arg; Gin; Glu); Met (Leu; Ile); Phe (Met; Leu; Tyr); Ser (Thr); Thr (Ser); Trp (Tyr); Tyr (Trp; Phe); and Val (lie; Leu).

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns, a DNA molecule (ex. cDNA), an RNA molecule (ex. mRNA), recombinant nucleic acids, plasmids, and other vectors, primers and probes. Both 5' to 3' (sense) and 3' to 5' (antisense) polynucleotides are included. The nucleotides can be deoxyribonucleotides, ribonucleotides, modified nucleotides or bases, and/or their analogs, or any substrate that can be incorporated into a polymer by DNA or RNA polymerase. A poly-nucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (for example, methyl phosphonates, phosphotriesters, phosphoamidates, carbamates, etc.) and with charged linkages (ex. phosphorothioates, phosphorodithioates, etc.), those containing pendant moieties, such as, for example, proteins (ex. nucleases, toxins, antibodies, signal peptides, poly-L-lysine, etc.), those with intercalators (ex. acridine, psoralen, etc.), those containing chelators (ex., metals, radioactive metals, boron, oxidative metals, etc.), those containing alkylators, those with modified linkages (ex. alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Vectors, as described herein, have expression control sequences meaning that a nucleic acid sequence that directs transcription of a nucleic acid. An expression control sequence can be a promoter, such as a constitutive or an inducible promoter, or an enhancer. The expression control sequence is 'operably linked' to the nucleic acid sequence to be transcribed. A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Just as a polypeptide may contain conservative amino acid substitution(s), a polynucleotide thereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, for example, a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

A "variant" anti-NGF antigen binding protein refers herein to a molecule which differs in amino acid sequence from a "parent" anti-NGF antibody amino acid sequence by virtue of addition, deletion, and/or substitution of one or more amino acid residue(s) in the parent antibody sequence and retains at least one desired activity of the parent anti-NGF-antibody. The variant anti-NGF may comprise conservative amino acid substitutions in the hypervariable region of the antibody, as described herein. Desired activities can include the ability to bind the antigen specifically, the ability to reduce, inhibit or neutralize NGF activity in an animal. In one embodiment, the variant comprises one or more amino acid substitution(s) in one or more hypervariable and/or framework region(s) of the parent antibody. For example, the variant may comprise at least one, e.g. from about one to about ten, and preferably from about two to about five, substitutions in one or more hypervariable and/or framework regions of the parent antibody. Ordinarily, the variant will have an amino acid sequence having at least 50% amino acid sequence identity with the parent antibody heavy or light chain variable domain sequences, more preferably at least about between 60%, 65%, 70%, 75%, 80% 85% 90% 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind NGF and preferably has desired activities which are equal to or superior to those of the parent antibody. For example, the variant may have a stronger binding affinity, enhanced ability to reduce, inhibit or neutralize NGF activity in an animal, and/or enhanced ability to inhibit NGF binding to TrkA and p75.

TrkA, considered the high affinity NGF receptor is a member of the neurotrophic tyrosine kinase receptor (NTKR) family. This kinase is a membrane-bound receptor that, upon neurotrophin binding, phosphorylates itself (autophosphorylation) and members of the MAPK pathway. The presence of this kinase leads to cell differentiation and may play a role in specifying sensory neuron subtypes. The p75 receptor is considered the low affinity NGF receptor.

A 'variant' nucleic acid, refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

The term "isolated" means that the material (for example, antigen binding protein as described herein or nucleic acid) is separated and/or recovered from a component of its natural environment. Contaminant components of its natural environment are materials that would interfere with diagnostic or therapeutic uses for the material, and may include enzymes, hormones, and other proteinaceous or non-proteinaceous solutes. With respect to nucleic acid, an isolated nucleic acid may include one that is separated from the 5' to 3' sequences with which it is normally associated in the chromosome. In preferred embodiments, the material will be purified to greater than 95% by weight of the material, and most preferably more than 99% by weight. Isolated material includes the material in situ within recombinant cells since at least one component of the material's natural environment will not be present. Ordinarily, however, isolated material will be prepared by at least one purification step.

As used herein, the terms "cell", "cell line", and "cell culture" may be used interchangeably. These terms also include their progeny, which are all subsequent generations. It is understood that all progeny may not be identical due to deliberate or inadvertent mutations. In the context of expressing a heterologous nucleic acid sequence, "host cell" refers to a prokaryotic or eukaryotic cell (for example, bacterial cells, yeast cells, mammalian cells, and insect cells) whether located in vitro or in vivo. For example, host cells may be located in a transgenic animal. Host cell can be used as a recipient for vectors and may include any transformable organism that is capable of replicating a vector and/or expressing a heterologous nucleic acid encoded by a vector.

The word "label" when used herein refers to a detectable compound or composition that is conjugated directly or indirectly to the antibody or nucleic acid. The label may itself be detectable by itself (for example, radioisotope labels or fluorescent labels) or, in the case of an enzymatic label, may catalyze chemical alteration of a substrate compound or composition that is detectable.

A "subject" or "patient" refers to an animal in need of treatment that can be affected by molecules of the invention. Animals that can be treated in accordance with the invention include vertebrates, with mammals such as canine being particularly preferred examples.

A "composition" is intended to mean a combination of active agent, whether chemical composition, biological composition or biotherapeutic (particularly antigen binding proteins as described herein) and another compound or composition which can be inert (for example, a label), or active, such as an adjuvant.

As defined herein, "pharmaceutically acceptable carriers" suitable for use in the invention are well known to those of skill in the art. Such carriers include, without limitation, water, saline, buffered saline, phosphate buffer, alcohol/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, citrates, ascorbic acid, gluconic acid, histidine-Hel, carbonic acid, tartaric acid, succinic acid, acetic acid, or phthalic acid, Tris, trimethanamine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (ex. EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, for example, texts such as Remington: The Science and Practice of Pharmacy, 20th ed, Lippincott Williams & Wilkins, publ., 2000; and The Handbook of Pharmaceutical Excipients, 4.sup.th edit., eds. R. C. Rowe et al, APhA Publications, 2003.

A "therapeutically effective amount" (or "effective amount") refers to an amount of an active ingredient, for example, an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated NGF related condition sufficient to effect beneficial or desired results including clinical results such as alleviation or reduction in pain sensation. An effective amount can be administered in one or more administrations.

For purposes of this invention, an effective amount of drug, compound, or pharmaceutical composition is an amount sufficient to treat, ameliorate, reduce the intensity of and/or prevent pain, including post-surgical pain, rheumatoid arthritis pain, and/or osteoarthritis pain. In some embodiments, the "effective amount" may reduce pain at rest (resting pain) or mechanically-induced pain (including pain following movement), or both, and it may be administered before, during or after a painful stimulus. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. Of course, the therapeutically effective amount will vary depending upon the particular subject and condition being treated, the weight and age of the subject, the severity of the condition, the particular compound chosen, the dosing regimen to be followed, timing of administration, the manner of administration and the like, all of which can readily be determined by one of ordinary skill in the art.

As used herein, the term "therapeutic" encompasses the full spectrum of treatments for a disease, condition or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

In a further aspect, the invention features veterinary compositions in which antibodies of the present invention are provided for therapeutic or prophylactic uses. The invention features a method for treating a dog subject having a particular antigen, for example, one associated with a disease or condition. The method includes administering a therapeutically effective amount of a recombinant antibody specific for the particular antigen, with the recombinant antibody described herein.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. The route of administration of the antibody or antigen-binding moiety of the invention may be oral, parenteral, by inhalation or topical. In a preferred embodiment, the route of administration is parenteral. The term parenteral as used herein includes intravenous, intramuscular, subcutaneous, rectal, vaginal or intraperitoneal administration.

"Pain" as used herein refers to pain of any etiology, including acute and chronic pain, and any pain with an inflammatory component. Examples of pain include including inflammatory pain, post-operative incision pain, neuropathic pain, fracture pain, osteoporotic fracture pain, postherpetic neuralgia, cancer pain, pain resulting from burns, pain associated with burn or wound, pain associated with trauma (including traumatic head injury), neuropathic pain, pain associated with musculoskeletal disorders such as rheumatoid arthritis, osteoarthritis, ankylosing spondylitis, seronegative (non-rheumatoid) arthropathies, non-articular rheumatism and periarticular disorders, and pain associated with cancer (including "break-through pain" and pain associated with terminal cancer), peripheral neuropathy and post-herpetic neuralgia.

As used herein, "treatment" is an approach for obtaining beneficial or desired clinical results. For purposes of this invention, beneficial or desired clinical results include, but are not limited to, one or more of the following: improvement or alleviation of any aspect of pain, including acute, chronic, inflammatory, neuropathic, post-surgical pain, rheumatoid arthritis pain, or osteoarthritis pain. For purposes of this invention, beneficial or desired clinical results include, but are not limited to, one or more of the following: including lessening severity, alleviation of one or more symptoms associated with pain including any aspect of pain (such as shortening duration of pain, reduction of pain sensitivity or sensation).

NGF Related Disorder, as described herein, refers to a disorder including cardiovascular diseases, atherosclerosis, obesity, type 2 diabetes, metabolic syndrome, pain and inflammation. In some embodiments of the present invention an NGF related disorder refers to pain, in particular chronic pain, inflammatory pain, post-operative incision pain, neuropathic pain, fracture pain, osteoporotic fracture pain, post-herpetic neuralgia, cancer pain, pain resulting from burns, pain associated with burn or wound, pain associated with trauma (including traumatic head injury), neuropathic pain, pain associated with musculoskeletal disorders such as rheumatoid arthritis, osteoarthritis, ankylosing spondylitis, seronegative (non-rheumatoid) arthropathies, non-articular rheumatism and periarticular disorders, and pain associated with cancer (including "break-through pain" and pain associated with terminal cancer), peripheral neuropathy and post-herpetic neuralgia.

"Reducing incidence" of pain means any of reducing severity (which can include reducing need for and/or amount of (ex: exposure to) other drugs and/or therapies generally used for this conditions, including, for example, opiates), duration, and/or frequency (including, for example, delaying or increasing time to post-surgical pain in an individual). As is understood by those skilled in the art, individuals may vary in terms of their response to treatment, and, as such, for example, a "method of reducing incidence of rheumatoid arthritis pain or osteoarthritis pain in an individual" reflects administering the anti-NGF antagonist antibody based on a reasonable expectation that such administration may likely cause such a reduction in incidence in that particular individual.

"Ameliorating" a pain or one or more symptoms of a pain (such as rheumatoid arthritis pain or osteoarthritis pain) means a lessening or improvement of one or more symptoms of a pain as compared to not administering an anti-NGF antagonist antibody. "Ameliorating" also includes shortening or reduction in duration of a symptom.

"Palliating" a pain or one or more symptoms of a pain (such as rheumatoid arthritis pain or osteoarthritis pain) means lessening the extent of one or more undesirable clinical manifestations of post-surgical pain in an individual or population of individuals treated with an anti-NGF antagonist antibody in accordance with the invention.

As used therein, "delaying" the development of pain means to defer, hinder, slow, retard, stabilize, and/or postpone progression of pain, such as post-surgical pain, rheumatoid arthritis pain, or osteoarthritis pain. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, post-surgical pain does not include pain that occurs (arises or originates) without an external physical trauma. In some embodiments, post-surgical pain is internal or external (including peripheral) pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain. The pain can be primary or secondary pain, as is well-known in the art.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

The invention disclosed herein concerns antigen binding proteins (used interchangeably with the terms "antibodies", "antagonist antibodies" "antibody fragments" and the like, as described herein), that specifically bind to Nerve Growth Factor (NGF) and in particular antibodies, whether it be canine, feline, equine, murine, bovine, human or any other species, caninized, felinized, bovinized, equinized, humanized or any other speciated antibodies produced by recombinant methods, hybridoma technologies or phage display technology or fully "caninized" (speciated) monoclonal antibodies that specifically bind to NGF and thus prevent NGF from binding to canine TrkA and to a lesser extent canine p75 receptors, thus serving as an antagonist in that the signaling pathway is prevented from being activated by NGF.

NGF was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne et al. (1994) Nature 368:246-249; Crowley et al. (1994) Cell 76:1001-1011). NGF upregulates expression of neuropeptides in sensory neurons (Lindsay et al. (1989) Nature 337:362-364) and its activity is mediated through two different membrane-bound receptors, the TrkA receptor and what is considered the low affinity p75 common neurotrophin receptor.

NGF has been shown to be elevated in NGF related disorders in which an elevated amount of NGF is present in injured or diseased tissues. An NGF related disorder, can be defined as an increase in pain due to the elevation of NGF in an injured, diseased or damaged tissue. Pain, as used herein, is defined as described herein, refers to a disorder including chronic pain, inflammatory pain, post-operative incision pain, neuropathic pain, fracture pain, osteoporotic fracture pain, post-herpetic neuralgia, cancer pain, pain resulting from burns, pain associated with burn or wound, pain associated with trauma (including traumatic head injury), neuropathic pain, pain associated with musculoskeletal disorders such as chronic pain, rheumatoid arthritis, osteoarthritis, ankylosing spondylitis, seronegative (non-rheumatoid) arthropathies, non-articular rheumatism and periarticular disorders, and pain associated with cancer (including "break-through pain" and pain associated with terminal cancer), peripheral neuropathy and post-herpetic neuralgia.

In an embodiment of the present invention, an NGF disorder is defined as osteoarthritis in a subject (canines, felines, equines, humans etc). Osteoarthritis (OA) is a slowly-progressive degenerative joint disease characterized by a loss of joint cartilage and the subsequent exposure of subchondral bone in canines. This eventually results in a self-perpetuating insidious disorder characterized by joint pain. New bone formation occurs in response to the chronic inflammation, and local tissue damage in an attempt to limit both movement and pain. Macroscopically, there is loss of joint cartilage, a narrowing of the joint space, sclerosis of subchondral bone, and the production of joint osteophytes (Veterinary Focus: Vol 17 No 3; 2007)

In different species, such as canines, felines, equines and the like, the onset of primary OA depends on breed. For canines, for example, the onset mean age is 3.5 years in Rottweilers and 9.5 years in Poodles for examples, with a wide range of onset for other breeds as well as mixed breeds. The developmental orthopedic diseases and associated osteoarthritis are the most common articular diseases in dogs, they account for some 70% of medical visits for articular disease and related problems within the appendicular skeleton. Twenty two percent of cases were dogs aged one year or under. The incidence of OA is increased by trauma as well as obesity, aging and genetic abnormalities. In particular, age can be a factor in OA incidence wherein >50% of arthritis cases are observed in dogs aged between 8-13 years. The musculoskeletal diseases are very common in geriatric patients, and nearly 20% of elderly dogs show orthopedic disorders. In Labrador Retrievers aged >8 years, OA in several joints (elbow, shoulder, hip, knee) is typical. Additionally, the size of the canine plays a role in OA onset as well. 45% of dogs with arthritis are large breed dogs. Among these, >50% are giant breed dogs, while only 28% are medium breed dogs and 27% are small breed dogs. The need for pharmaceutical intervention for the alleviation of OA pain in canines is very high.

As stated herein, elevated levels of NGF are indicative of a NGF related disorder, particularly in OA. Elevated levels of NGF have been reported in transgenic arthritic mice along with an increase in the number of mast cells (Aloe, et al., Int. J. Tissue Reactions-Exp. Clin. Aspects 15:139-143 (1993)). PCT Publication No. WO 02/096458 discloses use of anti NGF antibodies of certain properties in treating various NGF related disorders such as inflammatory condition (for example, rheumatoid arthritis). It has been reported that a purified anti-NGF antibody injected into arthritic transgenic mice carrying the human tumor necrosis factor gene caused reduction in the number of mast cells, as well as a decrease in histamine and substance P levels within the synovium of arthritis mice (Aloe et al., Rheumatol. Int. 14: 249-252 (1995)). It has been shown that exogenous administration of an NGF antibody reduced the enhanced level of TNFα, occurring in arthritic mice (Marmi et al., Rheumatol. Int. 18: 97-102 (1998)). Rodent anti-NGF antagonist antibodies have been reported. See, ex. Hongo et al., Hybridoma (2000) 19(3): 215-227; Ruberti et al. (1993) Cell. Molec. Neurobiol. 13(5): 559-568. However, when rodent antibodies are used therapeutically in non-murine mammals, an anti-murine antibody response develops in significant numbers of treated individuals. Thus, there is a serious need for anti-NGF antagonist antigen binding proteins, including anti-NGF antagonist antibodies of the present invention for canine use particularly for use in treating OA.

While the properties of antibodies make them very attractive therapeutic agents, there are a number of limitations. The vast majority of monoclonal antibodies (mAbs) are of rodent origin, as previously noted. When such antibodies are administered in a different species, patients can mount their own antibody response to such xenogenic antibodies. Such response may result in the eventual neutralization and elimination of the antibody. As described above mice are used extensively in the production of monoclonal antibodies. One problem in the using of antibodies produced by a particular species, generally initially in the mouse, is that a non-murine subject being treated with said antibodies react to the mouse antibodies as if they were a foreign substance thus creating a new set of antibodies to the mouse antibodies. Mouse antibodies are "seen" by the non-murine, for example canine, immune system as foreign, and the subject then mounts an immune response against the molecule. Those skilled in the field will recognize the need to be able to treat a subject with an antigen specific antibody, but have that antibody species specific. Part of the reaction generated from cross species antibody administration, for example a mouse monoclonal antibody being administered to a canine, can range from a mild form, like a rash, to a more extreme and life-threatening response, such as renal failure. This immune response can also decrease the effectiveness of the treatment, or create a future reaction if the subject is given a subsequent treatment containing mouse antibodies. Accordingly, we set forth to overcome this disadvantage by "caninization" of an antibody. In particular, this process focuses on the framework regions of the immunoglobulin variable domain, but could also include the compliment determinant regions (CDR's) of the variable domain. The enabling steps and reduction to practice for this process are described in this disclosure.

The process of modifying a monoclonal antibody (antigen binding protein, antagonist antibody etc as described herein and terms used interchangeably) from an animal to render it less immunogenic for therapeutic administration to species has been aggressively pursued and has been described in a number of publications (e.g. Antibody Engineering: A practical Guide. Carl A. K. Borrebaeck ed. W.H. Freeman and Company, 1992). However, this process has not been applied for the development of therapeutic or diagnostics for non-humans, particularly canines, until recently. In fact, very little has been published with regard to canine variable domains at all. Wasserman and Capra, Biochem. 6, 3160 (1977), determined the amino acid sequence of the variable regions of both a canine IgM and a canine IgA heavy chain. Wasserman and Capra, *Immunochem.* 15, 303 (1978), determined the amino acid sequence of the K light chain from a canine IgA. McCumber and Capra, *Mol. Immunol.* 16, 565 (1979), disclose the complete amino-acid sequence of a canine mu chain. Tang et al., *Vet. Immunology Immunopathology* 80, 259 (2001), discloses a single canine IgG-A γ chain cDNA and four canine IgG-A γ chain protein sequences. It describes PCR amplification of a canine spleen cDNA library with a degenerate oligonucleotide primer designed from the conserved regions of human, mouse, pig, and bovine IgGs. The paucity of information available on canine antibodies has prevented their development as therapeutics for the treatment canine disease.

These noted limitations have prompted the development of engineering technologies known as "speciation" and is well known to those in the art in terms of "humanization" of therapeutic antibodies. Caninized antibodies, as an example of speciated molecules can be generated as chimeric antibodies or fragments thereof which contain minimal sequence derived from non-canine immunoglobulin. For the most part, caninized antibodies are canine antibodies (i.e. "recipient antibody" or "target species antibody") in which residues from a complementarity determining region (CDR) of the recipient are replaced by residues from a CDR of a non-canine species (i.e. "donor antibody" or "originating species antibody") such as mouse, having the desired properties such as specificity, affinity, and potency. In some instances, framework region (FR) residues of the canine immunoglobulin are replaced by corresponding non-canine residues. This caninization strategy is referred to as "CDR grafting". Back mutation of selected target framework residues to the corresponding donor residues might be required to restore and or improved affinity. Structure-based methods may also be employed for caninization and affinity maturation. as described in U.S. Pat. No. 7,261,890.

The approaches described above utilize essentially entire framework regions from one or more antibody variable heavy chains or variable light chains of the target species which are engineered to receive CDRs from the donor species. This approach is also utilized when felinizing an antibody to make it less antigenic when administered to felines, in the same fashion as caninization. In some cases, back mutation of selected residues in the variable region is used to enhance presentation of the CDRs. Designing antibodies that minimize immunogenic reaction in a subject to non-native sequences in the antibody, while at the same time preserving antigen binding regions of the antibody sufficiently to maintain efficacy, has proven challenging.

Another challenge for developing therapeutic antibodies targeting proteins is that epitopes on the homologous protein in a different species are frequently different, and the potential for cross-reactivity with other proteins is also different. As a consequence, antibodies have to be made, tested and developed for the specific target in the particular species to be treated.

Antibodies target an antigen through its binding of a specific epitope on an antigen by the interaction with the variable region of the antibody molecule. Furthermore, antibodies have the ability to mediate, inhibit (as in the case of the antagonistic anti-NGF antigen binding protein of the present invention) and/or initiate a variety of biological activities. There are a wide range of functions for therapeutic antibodies, for example, antibodies can modulate receptor-ligand interactions as agonists or antagonists. Antibody binding can initiate intracellular signaling to stimulate cell growth, cytokine production, or apoptosis. Antibodies can deliver agents bound to the Fc region to specific sites. Antibodies also elicit antibody-mediated cytotoxicity (ADCC), complement-mediated cytotoxicity (CDC), and phagocytosis. There are also antibodies that have been altered where the ADCC, CDC, C1q binding and phagocytosis functions have been eliminated. In one embodiment of the present invention the antibody of the present invention comprises alterations in the Fc region of the antibody that alters effector function of said antibody.

Caninization and Felinization

As used herein, "caninized antibody" means an antibody having an amino acid sequence corresponding to that of an antibody produced by a canine and/or has been made using any of the techniques known in the art or disclosed herein. The same process is undertaken for the felinization process and should be applied to the description herewith. For the sake of simplicity caninization will primarily be used as the example, however these examples are not limited only to canine. The same concepts and designs apply to the speciation of other antigen binding proteins, for example feline, equine, human and the like). This definition of a caninized antibody includes antibodies comprising at least one canine heavy chain polypeptide or at least one canine light chain polypeptide. "Speciation", per se, of antibodies, and in particular the humanization of antibodies is a field of study well known to one skilled in the art. It has been unknown until recently whether the speciation of antibodies beyond humanization would yield a therapeutic antibody that could be efficacious in any other species. The present invention exemplifies the caninization and felinization of an anti-NGF antigen binding protein for therapeutic use in dogs and cats respectively.

Chimeric antibodies comprise sequences from at least two different species. As one example, recombinant cloning techniques may be used to include variable regions, which contain the antigen-binding sites, from a non-recipient antibody (i.e., an antibody prepared in a donor species immunized with the antigen) and constant regions derived from a recipient immunoglobulin.

Speciated (caninized, felinized and the like) antibodies are a type of chimeric antibody wherein variable region residues responsible for antigen binding (i.e., residues of a complementarity determining region, abbreviated complementarity determining region, or any other residues that participate in antigen binding) are derived from a non-canine (or non-feline) species, while the remaining variable region residues (i.e., residues of the framework regions) and constant regions are derived, at least in part, from canine (or feline) antibody sequences. A subset of framework region residues and constant region residues of a speciated antibody may be derived from non-canine (or feline) sources. Variable regions of a speciated antibody are also described as speciated (i.e., a speciated light or heavy chain variable region). The non-speciated species is typically that used for immunization with antigen, such as mouse, rat, rabbit, non-human primate, or other non-canine or non-feline mammalian species.

Complementarity determining regions (CDRs) are residues of antibody variable regions that participate in antigen binding. Several numbering systems for identifying CDRs are in common use. The Kabat definition is based on sequence variability, and the Clothia definition is based on the location of the structural loop regions. The AbM definition is a compromise between the Kabat and Clothia approaches. A speciated antibody of the invention may be constructed to comprise one or more CDRs. Still further, CDRs may be used separately or in combination in synthetic molecules such as SMIPs and small antibody mimetics.

Framework residues are those residues of antibody variable regions other than hypervariable or CDR residues. Framework residues may be derived from a naturally occurring canine (for example, but applicable in concept with other species such as feline, equine, human etc. For the sake of simplicity canine will be used as the representative species but the examples are not limited to canine as such) antibody, such as a canine framework that is substantially similar to a framework region of the antibody of the invention. Artificial framework sequences that represent a consensus among individual sequences may also be used. When selecting a framework region for caninization, sequences that are widely represented in canines may be preferred over less populous sequences. Additional mutations of the canine framework acceptor sequences may be made to restore murine residues believed to be involved in antigen contacts and/or residues involved in the structural integrity of the antigen-binding site, or to improve antibody expression.

Grafting of CDRs is performed by replacing one or more CDRs of an acceptor antibody (ex., a caninized antibody or other antibody comprising desired framework residues) with CDRs of a donor antibody (ex, a non-canine antibody). Acceptor antibodies may be selected based on similarity of framework residues between a candidate acceptor antibody and a donor antibody. For example, canine framework regions are identified as having substantial sequence homology to each framework region of the relevant non-canine antibody, and CDRs of the non-canine antibody are grafted onto the composite of the different canine framework regions.

Analysis of the three-dimensional structures of antibody-antigen complexes, combined with analysis of the available amino acid sequence data may be used to model sequence variability based on structural dissimilarity of amino acid residues that occur at each position within the CDR. CDRs of the present invention can also be utilized in small antibody mimetics, which comprise two CDR regions and a framework region (Qui et al. Nature Biotechnology Vol 25; 921-929; August 2007).

Acceptor frameworks for grafting of CDRs or abbreviated CDRs may be further modified to introduce desired residues. For example, acceptor frameworks may comprise a heavy chain variable region of a canine consensus sequence, optionally with non-canine donor residues at one or more of positions. Following grafting, additional changes may be made in the donor and/or acceptor sequences to optimize antibody binding and functionality. See ex., International Publication No. WO 91/09967.

The present invention further provides cells and cell lines expressing antibodies of the invention. Representative host cells include bacterial, yeast, mammalian and human cells, such as CHO cells, HEK-293 cells, HeLa cells, CV-1 cells, and COS cells. Methods for generating a stable cell line following transformation of a heterologous construct into a host cell are known in the art. Representative non-mammalian host cells include insect cells (Potter et al. (1993) Int. Rev. Immunol. 10(2-3):103-112). Antibodies may also be produced in transgenic animals (Houdebine (2002) Curr. Opin. Biotechnol. 13(6):625-629) and transgenic plants (Schillberg et al. (2003) Cell Mol. Life Sci. 60(3):433-45).

As discussed above, monoclonal, chimeric, species specific and speciated antibodies, which have been modified by, ex., deleting, adding, or substituting other portions of the antibody, ex. the constant region, are also within the scope of the invention. For example, an antibody can be modified as follows: (i) by deleting the constant region; (ii) by replacing the constant region with another constant region, ex., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others. In one embodiment of the present invention the antibody of the invention comprises an altered Fc region that alters effector function of the antibody. In some embodiments of the present invention the Fc region of the antigen binding protein of the invention has been replaced, modified or removed.

Methods for altering an antibody constant region are known in the art. Antibodies with altered function, e.g. altered affinity for an effector ligand, such as FcR on a cell, or the C component of complement can be produced by replacing at least one amino acid residue in the constant portion of the antibody with a different residue (see ex., EP 388,151 A1, U.S. Pat. Nos. 5,624,821 and 5,648,260, the contents of all of which are hereby incorporated by reference).

For example, it is possible to alter the affinity of an Fc region of an antibody for an FcR (ex. Fc.gamma R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see ex., U.S. Pat. No. 5,624,821). The antibody or binding fragment thereof may be conjugated with a cytotoxin, a therapeutic agent, or a radioactive metal ion. In one embodiment, the protein that is conjugated is an antibody or fragment thereof. A cytotoxin or cytotoxic agent includes any agent that is detrimental to cells. Non-limiting examples include, calicheamicin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, and analogs, or homologs thereof. Therapeutic agents include, but are not limited to, antimetabolites (ex., methotrexate, 6-mercaptopurine, 6-thioguanine, cytarabine, and 5-fluorouracil decarbazine), alkylating agents (ex., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP), cisplatin), anthracyclines (ex., daunorubicin and doxorubicin), antibiotics (ex., dactinomycin, bleomycin, mithramycin, and anthramycin), and anti-mitotic agents (ex., vincristine and vinblastine). Techniques for conjugating such moieties to proteins are well known in the art.

Compositions, Derived Compositions, and Methods of Making the Compositions

This invention encompasses compositions, including pharmaceutical compositions, comprising antigen binding proteins ("antibodies", "antibody fragments", "antagonist antibodies" and the like as used interchangeably herein), polypeptides and polynucleotides comprising sequences encoding antigen binding proteins or polypeptides of the invention.

As used herein, compositions comprise one or more antibodies, antigen binding proteins or polypeptides (which may or may not be an antibody) that bind to NGF, and/or one or more polynucleotides comprising sequences encoding one or more antibodies or polypeptides that bind to NGF. These compositions may further comprise suitable excipients, such as pharmaceutically/veterinary acceptable excipients including buffers, which are well known in the art. The invention also encompasses isolated antibody, polypeptide and polynucleotide embodiments. The invention also encompasses substantially pure antibody, polypeptide and polynucleotide embodiments.

In one or more embodiment, the present invention provides for novel antigen binding proteins that specifically bind to NGF. In one or more embodiments, the antigen binding protein is defined as an antibody or antibody fragment. In one or more embodiments, the antigen binding protein is fully canine, fully feline, feline bovine, fully equine, fully human, caninized, felinized, equinized or humanized. In one or more embodiments, the antigen binding protein of the present invention binds to canine, feline, equine or human NGF. In one embodiment, the antigen binding protein is a monoclonal antibody. In one embodiment, a monoclonal antibody of the invention binds to NGF and prevents its binding to, and activation of, its receptors Trk A and to a lesser extent p75, thus preventing the signaling cascade as described herein. The antigen binding protein of the present invention are identified herein as ZTS-841

In one or more embodiments, the present invention provides an isolated and recombinant antigen binding protein, "ZTS-841, wherein the variable heavy chain comprises amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 4 ("0ZTS-841" VH CDR1), amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 5 ("ZTS-841" VH CDR2), amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 6 ("ZTS-841" VH CDR3); and wherein the variable light chain comprises amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 1 ("ZTS-841" VL CDR1), amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 2 ("ZTS-841" VL CDR2), and amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 3 ("ZTS-841" VL CDR3); and any variants thereof having one or more conservative amino acid substitutions in at least one of CDR1, CDR2 or CDR3 within any of the variable light or variable heavy chains of said antigen binding protein.

In one or more embodiments, the present invention provides an isolated and recombinant antigen binding protein, "ZTS-842, wherein the variable heavy chain comprises amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 24 ("0ZTS-842" VH CDR1), amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 25 ("ZTS-842" VH CDR2), amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 26 ("ZTS-842" VH CDR3); and wherein the variable light chain comprises amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 21 1 ("ZTS-842" VL CDR1), amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 22 ("ZTS-842" VL CDR2), and amino acid sequence having at least about 85%, 86%, 87%, 88%, 89%, 90%, 91%, 92%, 93%, 94%, 95%, 96%, 97%, 98% or 99% sequence identity to the amino acid sequence comprising SEQ ID NO. 23 ("ZTS-842" VL CDR3); and any variants thereof having one or more conservative amino acid substitutions in at least one of CDR1, CDR2 or CDR3 within any of the variable light or variable heavy chains of said antigen binding protein.

The present invention provides for recombinant antigen binding proteins, in some embodiments described herein, monoclonal antibodies, and antibody fragments and their uses in clinical administrations and scientific procedures, including diagnostic procedures. With the use of methods of molecular biology and recombinant technology, it is possible to produce an antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric (H2L2) structures with affinity for specific epitopes and antigenic determinants. This has permitted the ready production of antibodies having sequences characteristic of neutralizing antibodies from different species and sources.

Regardless of the source of the antibodies, how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3-dimensional structure. This structure is often given as H2L2 and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or 'V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others. In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

The present invention further provides a vector including at least one of the nucleic acids described above. Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual encoding sequence can be estimated by considering abnormal base pairing relationships and the frequency with which a particular codon is actually used (to encode a particular amino acid) in eukaryotic or prokaryotic cells expressing an anti-NGF antibody or portion. Such "codon usage rules" are disclosed by Lathe, et al., 183 J. Molec. Biol. 1-12 (1985). Using the "codon usage rules" of Lathe, a single nucleotide sequence, or a set of nucleotide sequences that contains a theoretical "most probable" nucleotide sequence capable of encoding anti-NGF sequences can be identified. It is also intended that the antibody coding regions for use in the present invention could also be provided by altering existing antibody genes using standard molecular biological techniques that result in variants (agonists) of the antibodies and peptides described herein. Such variants include, but are not limited to deletions, additions and substitutions in the amino acid sequence of the anti-NGF antibodies or peptides.

For example, one class of substitutions is conservative amino acid substitutions. Such substitutions are those that substitute a given amino acid in an anti-NGF antibody peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gin, exchange of the basic residues Lys and Arg, replacements among the aromatic residues Phe, Tyr, and the like. Guidance concerning which amino acid changes are likely to be phenotypically silent is found in Bowie et al., 247 Science 1306-10 (1990).

Variant anti-NGF antigen binding proteins or antibody fragments may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in the art and have been described in great detail in the scientific literature. Several particularly common modifications, glycosylation, lipid attachment, sulfation, gamma-carboxylation of glutamic acid residues, hydroxylation and ADP ribosylation, for instance, are described in most basic texts, such as Proteins-Structure and Molecular Properties (2nd ed., T. E. Creighton, W.H. Freeman & Co., NY, 1993). Many detailed reviews are available on this subject, such as by Wold, Posttranslational Covalent Modification of proteins, 1-12 (Johnson, ed., Academic Press, N Y, 1983); Seifter et al. 182 Meth. Enzymol. 626-46 (1990); and Rattan et al. 663 Ann. NY Acad. Sci. 48-62 (1992).

Accordingly, the antibodies and peptides of the present invention also encompass derivatives or analogs in which a substituted amino acid residue is not one encoded by the genetic code. Similarly, the additions and substitutions in the amino acid sequence as well as variations, and modifications just described may be equally applicable to the amino acid sequence of the NGF antigen and/or epitope or peptides thereof, and are thus encompassed by the present invention. As mentioned above, the genes encoding a monoclonal antibody according to the present invention is specifically effective in the recognition of NGF.

Antibody Derivatives

Included within the scope of this invention are antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine (251,1311), carbon (4C), sulfur (35S), indium, tritium ($H^3$) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemiluminescent agents (such as acridine esters) or fluorescent agents (such as phycobiliproteins).

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (ex., by lengthening the time to clearance from the blood stream. Such techniques include, for example, adding PEG moieties (also termed pegilation), and are well-known in the art. See U.S. Patent. Appl. Pub. No. 20030031671.

Recombinant Expression of Antibodies

In some embodiments, the nucleic acids encoding a subject monoclonal antibody are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing. Traditionally, monoclonal antibodies have been produced as native molecules in murine hybridoma lines. In addition to that technology, the present invention provides for recombinant DNA expression of monoclonal antibodies. This allows the production of caninized antibodies, as well as a spectrum of antibody derivatives and fusion proteins in a host species of choice.

A nucleic acid sequence encoding at least one anti-NGF antibody, portion or polypeptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, ex. by Maniatis et al., MOLECULAR CLONING, LAB. MANUAL, (Cold Spring Harbor Lab. Press, N Y, 1982 and 1989), and Ausubel et al. 1993 supra, may be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-NGF peptides or antibody portions in recoverable amounts. The precise nature of the regulatory regions needed for gene expression may vary from organism to organism, as is well known in the analogous art. See, ex. Sambrook et al., 2001 supra; Ausubel et al., 1993 supra.

The present invention accordingly encompasses the expression of an anti-NGF antibody or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

In one embodiment, the nucleotide sequence of the invention will be incorporated into a plasmid or viral vector capable of autonomous replication in the recipient host. Any of a wide variety of vectors may be employed for this purpose. See, ex., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli* (such as but not limited to, for example, pBR322, ColE1, pSC101, pACYC 184, and the like). Such plasmids are, for example, disclosed by Maniatis et al., 1989 supra; Ausubel et al, 1993 supra. *Bacillus* plasmids include pC194, pC221, pT127, etc. Such plasmids are disclosed by Gryczan, in THE MOLEC. BIO. OF THE BACILLI 307-329 (Academic Press, N Y, 1982). Suitable *Streptomyces* plasmids include plJ101 (Kendall et al., 169 J. Bacteriol. 4177-83 (1987), and *Streptomyces* bacteriophages such as phLC31 (Chater et al., in SIXTH INT'L SYMPOSIUM ON ACTINOMYCETALES BIO. 45-54 (Akademiai Kaido, Budapest, Hungary 1986). *Pseudomonas* plasmids are reviewed in John et al., 8 Rev. Infect. Dis. 693-704 (1986); Izaki, 33 Jpn. J. Bacteriol. 729-42 (1978); and Ausubel et al., 1993 supra.

Alternatively, gene expression elements useful for the expression of cDNA encoding anti-NGF antibodies or peptides include, but are not limited to (a) viral transcription promoters and their enhancer elements, such as the SV40 early promoter (Okayama et al., 3 Mol. Cell. Biol. 280 (1983), Rous sarcoma virus LTR (Gorman et al., 79 Proc. Natl. Acad. Sci., USA 6777 (1982), and Moloney murine leukemia virus LTR (Grosschedl et al., 41 Cell 885 (1985); (b) splice regions and polyadenylation sites such as those derived from the SV40 late region (Okayarea et al., 1983), and (c) polyadenylation sites such as in SV40 (Okayama et al., 1983).

Immunoglobulin cDNA genes can be expressed as described by Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements. For immunoglobulin genes comprised of part cDNA, part genomic DNA (Whittle et al., 1 Protein Engin. 499 (1987»), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the chimeric immunoglobulin chain gene product are then transfected singly with an anti-NGF peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-NGF peptide or chimeric H and L chains, or portions thereof are assembled in separate expression vectors that are then used to co-transfect a recipient cell. Alternatively, the fused genes encoding the chimeric H and L chains can be assembled on the same expression vector. For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of human or nonhuman origin, hybridoma cells of human or non-human origin, or interspecies heterohybridoma cells.

The expression vector carrying a chimeric, caninized antibody construct or anti-NGF polypeptide of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et at, 240 Science 1538 (1988).

Yeast can provide substantial advantages over bacteria for the production of immunoglobulin H and L chains. Yeasts carry out post-translational peptide modifications including glycosylation. Several recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molec. Biol. (Montpelier, France, 1982).

Yeast gene expression systems can be routinely evaluated for the levels of production, secretion and the stability of anti-NGF peptides, antibody and assembled murine and chimeric, heterochimeric, caninized, antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. Several approaches can be taken for evaluating optimal expression plasmids for the expression of cloned immunoglobulin cDNAs in yeast. See Vol. II DNA Cloning, 45-66, (Glover, ed.) IRL Press, Oxford, U K 1985).

Bacterial strains can also be utilized as hosts to produce antibody molecules or peptides described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine, chimeric, heterochimeric, caninized antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. *Current Protocols in Immunology*, John Wiley & Sons, NY, NY (1994-2001); Colligan et al., eds. Current Protocols in Protein Science, John Wiley & Sons, NY, NY (1997-2001).

Host mammalian cells may be grown in vitro or in vivo. Mammalian cells provide posttranslational modifications to immunoglobulin protein molecules including leader peptide removal, folding and assembly of Hand L chains, glycosylation of the antibody molecules, and secretion of functional antibody protein. Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Many vector systems are available for the expression of cloned anti-NGF peptides Hand L chain genes in mammalian cells (see Glover, 1985 supra). Different approaches can be followed to obtain complete H2L2 antibodies. It is possible to co-express Hand L chains in the same cells to achieve intracellular association and linkage of Hand L chains into complete tetrameric H2L2 antibodies and/or anti-NGF peptides. The co-expression can occur by using either the same or different plasmids in the same host. Genes for both Hand L chains and/or anti-NGF peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. cell lines producing anti-NGF peptides and/or H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody of the invention has been produced, it may be purified by any method known in the art for purification of an immunoglobulin molecule, for example, by chromatography (ex. ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Pharmaceutical and Veterinary Applications

The anti-NGF antigen binding protein or antibody fragments as described herein of the present invention can be used for example in the treatment of NGF related disorders in dogs and cats. More specifically, the invention further provides for a pharmaceutical composition comprising a pharmaceutically acceptable carrier or diluent and, as active ingredient, an antibody or antibody fragment per the invention. The antibody can be a chimeric, heterochimeric, caninized, felinized, equinized, humanized or speciated to accommodate a different species. Intact immunoglobulins or their binding fragments, such as Fab, are also envisioned. The antibody and pharmaceutical compositions thereof of this invention are useful for parenteral administration, ex., subcutaneously, intramuscularly or intravenously.

Anti-NGF antibodies and/or peptides of the present invention can be administered either as individual therapeutic agents or in combination with other therapeutic agents. They can be administered alone, but are generally administered with a pharmaceutical carrier selected on the basis of the chosen route of administration and standard pharmaceutical practice. Administration of the antibodies disclosed herein may be carried out by any suitable means, including parenteral injection (such as intraperitoneal, subcutaneous, or intramuscular injection), orally, or by topical administration of the antibodies (typically carried in a pharmaceutical formulation) to an airway surface. Topical administration to an airway surface can be carried out by intranasal administration (ex., by use of dropper, swab, or inhaler). Topical administration of the antibodies to an airway surface can also be carried out by inhalation administration, such as by creating respirable particles of a pharmaceutical formulation (including both solid and liquid particles) containing the antibodies as an aerosol suspension, and then causing the subject to inhale the respirable particles. Methods and apparatus for administering respirable particles of pharmaceutical formulations are well known, and any conventional technique can be employed.

In some desired embodiments, the antibodies are administered by parenteral injection. For parenteral administration, anti-NGF antibodies or peptides can be formulated as a solution, suspension, emulsion or lyophilized powder in association with a pharmaceutically acceptable parenteral vehicle. For example, the vehicle may be a solution of the antibody or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (ex., sodium chloride, mannitol) and chemical stability (ex., buffers and preservatives). The formulation is sterilized by commonly used techniques. Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss and that use levels may have to be adjusted to compensate. The compositions containing the present antibodies or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art. In therapeutic application, compositions are administered to a subject already suffering from a disease, in an amount sufficient to cure or at least partially arrest or alleviate the disease and its complications. An amount adequate to accomplish this is defined as a "therapeutically effective dose" or a "therapeutically effective amount". Amounts effective for this use will depend upon the severity of the disease and the general state of the subject's own immune system, but generally range from about 0.1 mg antibody per kg body weight to about 10 mg antibody per kg body weight, preferably about 0.3 mg antibody per kg of body weight to about 5 mg of antibody per kg of body weight. In view of the minimization of extraneous substances and the lower probability of "foreign substance" rejections which are achieved by the present canine-like and antibodies of this invention, it may be possible to administer substantial excesses of these antibodies.

The dosage administered will, of course, vary depending upon known factors such as the pharmacodynamic characteristics of the particular agent, and its mode and route of administration; age, health, and weight of the recipient; nature and extent of symptoms kind of concurrent treatment, frequency of treatment, and the effect desired.

As a non-limiting example, treatment of NGF-related pathologies in dogs and cats can be provided as a biweekly or monthly dosage of anti-NGF antibodies of the present invention in the dosage range as needed. Example antibodies for canine therapeutic use are high affinity (these may also be high avidity) antibodies, and fragments, regions and derivatives thereof having potent in vivo anti-NGF activity, according to the present invention. Single or multiple administrations of the compositions can be carried out with dose levels and pattern being selected by the treating veterinarian. In any event, the pharmaceutical formulations should provide a quantity of the antibody(ies) of this invention sufficient to effectively treat the subject.

Diagnostic Applications

The present invention also provides the above anti-NGF antibodies and peptides for use in diagnostic methods for detecting NGF in species, particularly canines and felines, known to be or suspected of having an NGF related disorder. In an embodiment of the invention the NGF related disorder is pain. In another embodiment, the NGF related disorder is osteoarthritis. Anti-NGF antibodies and/or peptides of the present invention are useful for immunoassays which detect or quantitate NGF, or anti-NGF antibodies, in a sample. An immunoassay for NGF typically comprises incubating a clinical or biological sample in the presence of a detectably labeled high affinity (or high avidity) anti-NGF antibody or polypeptide of the present invention capable of selectively binding to NGF, and detecting the labeled peptide or antibody which is bound in a sample. Various clinical assay procedures are well known in the art. See, ex. IMMUNO-ASSAYS FOR THE 80'S (Voller et al., eds., Univ. Park, 1981). Such samples include tissue biopsy, blood, serum, and fecal samples, or liquids collected from animal subjects and subjected to ELISA analysis as described below. Thus, an anti-NGF antibody or polypeptide can be fixed to nitrocellulose, or another solid support which is capable of immobilizing cells, cell particles or soluble proteins. The support can then be washed with suitable buffers followed by treatment with the detectably labeled NGF specific peptide, antibody or antigen binding protein. The solid phase support can then be washed with the buffer a second time to remove unbound peptide or antibody. The amount of bound label on the solid support can then be detected by known method steps.

"Solid phase support" or "carrier" refers to any support capable of binding peptide, antigen, or antibody. Well-known supports or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to NGF or an anti-NGF antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation. Well known method steps can determine binding activity of a given lot of anti-NGF peptide and/or antibody or antigen binding protein. Those skilled in the art can determine operative and optimal assay conditions by routine experimentation.

Detectably labeling an NGF-specific peptide and/or antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the NGF-specific antibodies of the present invention include, but are not limited to, malate dehydrogenase, staphylococcal nuclease, delta5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. By radioactively labeling the NGF-specific antibodies, it is possible to detect NGF through the use of a radioimmunoassay (RIA). See Work et al., LAB. TECHNIQUES & BIOCHEM. IN MOLEC. BIO (No. Holland Pub. Co., NY, 1978). The radioactive isotope can be detected by such means as the use of a gamma counter or a scintillation counter or by autoradiography. Isotopes which are particularly useful for the purpose of the present invention include: $^3$H, $^{125}$I, $^{131}$I, $^{35}$S and $^{14}$C.

It is also possible to label the NGF-specific antibodies with a fluorescent compound. When the fluorescent labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The NGF-specific antibodies or antigen binding proteins can also be delectably labeled using fluorescence-emitting metals such a $^{125}$Eu, or others of the lanthanide series. These metals can be attached to the NGF specific antibody using such metal chelating groups as diethylenetriaminepentaacetic acid (DTPA) or ethylenediamine-tetraacetic acid (EDTA).

The NGF-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the NGF-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the NGF-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

For the purposes of the present invention, the NGF which is detected by the above assays can be present in a biological sample. Any sample containing NGF may be used. For example, the sample is a biological fluid such as, for example, blood, serum, lymph, urine, feces, inflammatory exudate, cerebrospinal fluid, amniotic fluid, a tissue extract or homogenate, and the like. The invention is not limited to assays using only these samples, however, it being possible for one of ordinary skill in the art, in light of the present specification, to determine suitable conditions which allow the use of other samples.

In situ detection can be accomplished by removing a histological specimen from an animal subject, and providing the combination of labeled antibodies of the present invention to such a specimen. The antibody (or portion thereof) may be provided by applying or by overlaying the labeled antibody (or portion) to a biological sample. Through the use of such a procedure, it is possible to determine not only the presence of NGF but also the distribution of NGF in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid phase antibody, antigen, and labeled antibody.

The antibodies may be used to quantitatively or qualitatively detect the NGF in a sample or to detect presence of cells that express the NGF. This can be accomplished by immunofluorescence techniques employing a fluorescently labeled antibody (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the antibody, such as antibodies specific for canine immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art. Importantly, the antibodies of the present invention may be helpful in diagnosing an NGF related disorder in canines. More specifically, the antibody of the present invention may identify the overexpression of NGF in companion animals. Thus, the antibody of the present invention may provide an important immunohistochemistry tool. The antibodies of the present invention may be used on antibody arrays, highly suitable for measuring gene expression profiles.

Kits

Also included within the scope of the present invention are kits for practicing the subject methods. The kits at least include one or more of the antibodies of the present invention, a nucleic acid encoding the same, or a cell containing the same. An antibody of the present invention may be provided, usually in a lyophilized form, in a container. The antibodies, which may be conjugated to a label or toxin, or unconjugated, are typically included in the kits with buffers, such as Tris, phosphate, carbonate, etc., stabilizers, biocides, inert proteins, ex., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about, 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use.

The invention will now be described further by the non-limiting examples below.

EXAMPLES

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

Example 1

Synthesis and Purification of Canine NGF (cNGF)

PCR primers were designed with appropriate restriction sites to amplify canine pre-pro-ß-NGF (SEQ ID NO:59). The ß-NGF gene was cloned into plasmid pCTV927 (Chromos targeting plasmid) via EcoRV/KpnI sites. The pCTV927/ß-NGF plasmid was co-transfected, along with the plasmid encoding the Chromos system integrase pSIO343, using Lipofectamine 2000 transfection reagent into CHOK1SV cells. Individual stable clones were analyzed for expression and a high expressing clone was chosen for expansion and expression for subsequent purification. Canine β-NGF (cNGF) produced from these transfections was purified using ion exchange chromatography. Initial cleanup was performed in flow-through batch mode over Q Sepharose FF (GE Healthcare #17-0510-01). The clarified supernatant was diluted 1:1 with water and pH adjusted to 8.5 with 1 M Tris. The diluted sample was mixed with Q Sepharose FF, at a ratio of 150:1, for >1.5 hours. The resin was allowed to settle and the unbound portion collected. cNGF was further purified by cation exchange chromatography; it was diluted again 1:1 with water and loaded onto SP-Sepharose FF (GE Healthcare #17-0729-01) pre-equilibrated with 20 mM Tris, pH 8.5. After loading, the column was washed and then eluted via a linear gradient from 0 to 210 mM NaCl (each in 20 mM Tris, pH 8.5) over 20 column volumes. Fractions were analyzed by SDS-PAGE, pooled, dialyzed (3.5K mwco) against PBS at 4° C. The dialysate was collected, sterile filtered, and concentration measured via absorbance at 280 nm (1 mg/mL=1.48 $A_{280}$).

Example 2

Canine Immunizations

Immunizations of canines can be done by methods known in the art and are not limited to any one method. In one example, canine NGF (as described in Example 1) is administered directly into dogs with an adjuvant to stimulate immune response. To obtain optimal anti-antigen responses, canines were administered boost injections and serum samples were collected regularly. The antibody immune response from immunized dogs was monitored and determined using standard antigen direct binding enzyme linked immunosorbent assay (ELISA) methods, as well known to one of skill in the art and described below.

Example 3

Primary Antigen Binding and B-Cell Activation

To evaluate the titers of canine anti-NGF antibodies 100 uL of recombinant canine NGF (10 ug/mL) was coated overnight in Immunolon 2Hb plates at 4 degrees C. Wells were washed PBS-T (PBS+0.1% Tween) three times and non-specific binding was blocked using 200 uL of PBS+5% non-fat skim milk incubated for 1 hour at room temperature. After three plate washes with 300 uL PBD-T serial dilutions of canine sera were incubated for one hour. The binding of canine anti-NGF IgGs was detected using a cocktail 100 uL of Bethyl anti Dog IgG1 (A40-120P) and anti-Dog IgG2 (A40-121P) at 0.2 ug/mL. Following addition of a chromogenic substrate (SureBlue Reserve TMB 1-Component Microwell Peroxidase Substrate, KPL 53-00-01) and a ten-minute incubation at RT the reaction was stopped with the addition of 100 µL 0.1 N HCl. The absorbance of each well was determined at an optical density (OD) of 450 nm.

Activation Protocol for Canine Memory B Cells

Peripheral Blood Mononuclear Cells (PBMCs) were isolated using Ficoll™ gradient separation by centrifugation. After isolation of the PBMCs from the sample a specific selection of antibody secreting cells was performed based on expression of specific antibody cell surface markers well known to one of skill in the art and as described in US 2014/0287402 and Callard and Kotowicz "Cytokine Cell Biology: A practical approach" Oxford University Press, 2000, pg 17-31, herein incorporated by reference. Prior to depositing the B cells on to sorting chips, the cells were activated in vitro. After isolation and freezing, the cells (PBMCs, approx. $10^7$ cells/vial) were removed from liquid nitrogen and thawed rapidly in a water bath. The cells were transferred to 15 ml centrifuge tubes and 12 ml complete medium was added dropwise. After centrifuging the cells at 1000 rpm for 10 min, the pellet was resuspended in 10 ml of complete medium and centrifuged again at 1000 rpm for 10 min. Finally, the cells were resuspended in 4 mis medium.

Example 4

DNA Sequences Encoding 9L12 (ZTS-841), 48L2 (ZTS-842) and 13L11 Antibodies

The single cells of interest were retrieved from microarrays by micromanipulation and deposited into microtubes containing lysis buffer and magnetic beads for mRNA capture. cDNA was prepared from total RNA with a mix of gene specific primers hybridizing in the early constant domains of gamma HC, kappa LC and lambda LC. The terminal deoxynucleotidyl Transferase (TdT) enzyme was used for 3' end tailing of the first strand cDNA product. For the subsequent first PCR, a mix of gene specific reverse primers and a universal primer forward primer is used. Subsequently, nested PCRs were carried out separately for each VH and VL chain to amplify the antibody variable regions. The reverse primers used for this are located in the HC or LC constant domain together with a universal forward primer. Fragments amplified from the PCR were separated by gel electrophoresis on an agarose gel. The full length VH and VL amplicons isolated from a single cell were cloned into expression vectors containing the constant parts of corresponding HC or LC. Canine variable domain sequences were as follows: 9L12 (841) variable light chain (SEQ ID NO: 7), corresponding nucleotide sequence (SEQ ID NO: 17); 9L12 (841) variable heavy chain (SEQ ID NO: 8), corresponding nucleotide sequence (SEQ ID NO: 18); 48L2 (842) variable light chain (SEQ ID NO: 27), corresponding nucleotide sequence (SEQ ID NO: 37); 48L2 (842) variable heavy chain (SEQ ID NO: 28), corresponding nucleotide sequence (SEQ ID NO: 38); 13L11 variable light chain (SEQ ID NO: 51), corresponding nucleotide sequence (SEQ ID NO: 53); 13L11 variable heavy chain (SEQ ID NO: 52), corresponding nucleotide sequence (SEQ ID NO: 54).

The constant regions of the isolated antibodies isolated as described above were not used in the subsequent construction of the antibodies of the invention. The Fc region of the recombinant antibodies of the invention comprise a modified version of canine IgGB (Bergeron et al., Vet Immunol Immunopathol Jan. 15, 2014:157 (1-2): 31-41) and was chosen for its half-life, biophysical properties and lack of effector functions. As reported in Bergeron et al., canine IgGB has good affinity to canine FcRn and biophysical properties suitable for downstream processing. Differential Scanning Calorimetry (DSC) done on the canine Fc region alone indicated thermal stabilities of the constant regions were approximately 70° C. and 83° C. These melting temperatures are similar or higher than those reported for marketed humanized mAbs.

Three point mutations were made to the CH2 domain of canine IgGB to ablate ADCC and CDC activity. The mutated Fc is referred to herein as IgGB(e-) (SEQ ID NO. 43). Although NGF is a soluble target, effector functions were eliminated from the anti-NGF antibody to protect against any potential non-specific target or effector-function associated adverse effects. These mutations did not appear to influence immunogenicity of this mAb. Additionally, mutations to the Fc region to eliminate effector functions did not affect FcRn or Protein A binding. Decreased binding to canine FcγRI and FcγRIII were observed as well as a reduction in ADCC activity. C1q protein is the first protein in the complement cascade and is required for cells to undergo Complement Dependent Cytotoxicity (CDC). IgGB (e-) has been shown to lack binding to C1q protein. The amino acid sequence of canine constant HC-65, as described, is represented as SEQ ID NO: 41, and its corresponding nucleotide sequence is represented as SEQ ID NO: 42. The amino acid sequence of canine constant lambda is represented as SEQ ID NO: 60, and its corresponding nucleotide sequence is represented as SEQ ID NO: 61.

Example 5

Antigen Binding Affinity Determination

Antibody binding affinities of the antibodies against canine NGF were determined by surface plasmon resonance (SPR) on a Biacore system (Biocore Life Sciences (GE Healthcare), Uppsala, Sweden). Immobilization of canine and rat NGF were obtained by amine coupling 5 µg/mL NGF using N-hydroxysuccinimide (NHS)/1-Ethyl-3-(3-dimethylaminopropyl) carbodiimide (EDC) chemistry. Chips were quenched with ethanolamine and the affinity with which all candidate mAbs bound to the immobilized NGF was evaluated. Various concentrations of canine and felinized anti-NGF antibodies were injected over the NGF surfaces while the association of the antibody to the antigen and the dissociation of the formed complex were monitored in real time. Kinetic analysis was performed to obtain the equilibrium dissociation constant (KD). The results are shown in Table 1 below.

TABLE 1

Canine and rat NGF Binding Kinetics Summary

| Antigen | Name | ZTS | ka (M − 1 s − 1) | kd (s − 1) | KD (M) |
| --- | --- | --- | --- | --- | --- |
| canine NGF | 48L2 | ZTS-842 | 7.03E+05 ± 2.72E+05 | 2.27E−05 ± 5.30E−05 | 2.17E−11 ± 5.13E−11 |
| canine NGF | 9L12 | ZTS-841 | 5.27E+05 ± 1.44E+05 | 2.36E−05 ± 2.84E−05 | 5.06E−11 ± 6.73E−11 |
| canine NGF | fel48L2 1.1 | ZTS-205 | 4.26E+05 ± 2.21E+05 | 8.93E−05 ± 2.14E−04 | 1.11E−10 ± 2.56E−10 |
| canine NGF | fel48L2 1.2 | ZTS-206 | 4.22E+05 ± 2.10E+05 | 8.64E−05 ± 2.04E−04 | 1.13E−10 ± 2.55E−10 |
| canine NGF | fel48L2 chimera | | 4.71E+05 ± 1.26E+05 | 2.64E−06 ± 1.71E−06 | 6.25E−12 ± 5.40E−12 |
| rat NGF | 48L2 | ZTS-842 | 5.73E+05 ± 2.65E+05 | 1.42E−06 ± 1.45E−06 | 3.25E−12 ± 3.43E−12 |
| rat NGF | 9L12 | ZTS-841 | 5.87E+05 ± 2.32E+05 | 4.61E−05 ± 4.69E−05 | 1.08E−10 ± 1.21E−10 |
| rat NGF | fel48L2 1.1 | ZTS-205 | 6.72E+05 ± 3.41E+05 | 2.9E−04 ± 5.01E−04 | 2.77E−10 ± 4.77E−10 |
| rat NGF | fel48L2 1.2 | ZTS-206 | 6.42E+05 ± 3.13E+05 | 2.91E−04 ± 4.83E−04 | 3.09E−10 ± 4.80E−10 |
| rat NGF | fel48L2 chimera | | 3.87E+05 | 1.10E−07 | 2.85E−13 |

Example 6

Construction of 9L12 (841) and 48L2 (842) Chimeric Antibodies

Antibody variable domains are responsible for antigen binding. Antibodies consist of a homodimer pairing of two heterodimeric proteins. Each protein chain (one heavy and one light) of the heterodimer consists of a variable domain and a constant domain. Each variable domain contains three complementary determining regions (CDRs) which contribute to antigen binding. CDRs are separated in the variable domain by framework regions which provide a scaffold for proper spatial presentation of the binding sites on the antibody. Together the CDR and framework regions contribute to the antibodies ability to bind its cognate antigen. Grafting of the full variable domain onto respective constant region is expected to have little or no impact on the antibody's ability to bind NGF. To simultaneously confirm that the correct sequence of the heavy and light chain variable regions was identified and to produce homogenous material, expression vectors were designed to produce recombinant chimeric or canine antibodies in mammalian expression systems. Chimeric antibodies described here consist of the variable sequence (both CDR and framework) from the host species antibody grafted onto the respective heavy and light constant regions of a canine IgG molecule. The chimeric antibody described herein consists of the variable segment (both CDR and framework) from the canine molecule grafted onto the respective heavy and light constant regions of a feline IgG molecule. As the variable domain is responsible for antigen binding, grafting of the fully canine variable domain onto a feline constant domain is expected to have little or no impact on the antibody's ability to bind NGF. The chimeric variable domain sequences were as follows: canfel_chimera 9L12 (841) variable light chain (SEQ ID NO: 9), corresponding nucleotide sequence (SEQ ID NO: 19); canfel_chimera 9L12 (841) variable heavy chain (SEQ ID NO: 10), corresponding nucleotide sequence (SEQ ID NO: 21); canfel_chimera 48L2 (842) variable light chain (SEQ ID NO: 29), corresponding nucleotide sequence (SEQ ID NO: 39); canfel_chimera 48L2 (842) heavy chain (SEQ ID NO: 30), corresponding nucleotide sequence (SEQ ID NO: 40). Each variable segment was cloned into a mammalian expression plasmid containing either the feline IgG heavy or light chain. The amino acid sequence of the feline heavy constant region is represented as SEQ ID NO: 62 and its corresponding nucleotide sequence is represented as SEQ ID NO: 63. The amino acid sequence of the feline light constant is represented as SEQ ID NO: 64, and its corresponding nucleotide sequence is represented as SEQ ID NO: 65.

Example 7

Felinization of 48L2 and 9L12 Antibodies

The generation of anti-drug antibodies (ADAs) can be associated with loss of efficacy for any biotherapeutic protein including monoclonal antibodies. Comprehensive evaluation of the literature has shown that speciation of monoclonal antibodies can reduce the propensity for mAbs to be immunogenic. To help mitigate risks associated with ADA formation for the canine anti-NGF monoclonal antibodies provided herein, a felinization strategy was employed for the ultimate use of the antibodies in felines. This felinization strategy is based on identifying the most appropriate feline germline antibody sequence to be used for CDR grafting. Following extensive analysis of all available feline germline sequences for both, heavy and light chain, germline candidates were selected based on their homology to the canine mAbs, and the CDRs from the canine progenitor segments were used to replace native feline CDRs. Felinized mAbs were expressed and characterized for their ability to bind NGF. The objective was to retain high affinity and cell-based activity using feline antibody frameworks to minimize the potential of immunogenicity in vivo. Synthetic constructs representing the felinized variable heavy and light chains of mAb 48L2 (ZTS-842) using SEQ ID NOs 21-26 and 9L12 (ZTS-841) using SEQ ID NOs 1-6 were made. Following subcloning of each variable chain into plasmids containing the feline constant heavy (SEQ ID NO:62) and feline constant light (SEQ ID NO:64) regions, plasmids were co-transfected for antibody expression in HEK293 cells. Chimeric, heterochimeric and felinized versions of mAb 48L2 and 9L12 were expressed and characterized for their ability to bind NGF via SPR.

Example 8

Production of Antibodies from Glutamine Synthetase (GS) Plasmids

The genes encoding the canine and felinized 9L12 and 48L2 (ZTS-841 and ZTS-842 respectively), as described herein, and felinized 9L12 heavy and light chains were cloned into GS plasmids pEE 6.4 and pEE 12.4 (Lonza, Basel, Switzerland) according to standard molecular biology techniques well known to those of skill in the art. The resulting individual plasmids were digested per the manufacturer's protocol and ligated together to form a single mammalian expression plasmid. To demonstrate transient production of each antibody, each plasmid was used to transfect HEK 293 cells and expression was carried out in various size cultures. Protein was isolated from conditioned HEK medium using Protein A affinity chromatography per standard protein purification methods. Medium was loaded onto chromatographic resin and eluted by pH shift. Eluted protein was pH adjusted, dialyzed, and sterile filtered prior to use. Antibodies were tested for affinity and potency.

For generation of a stable cell line producing candidate antibodies, the GS plasmid was linearized prior to transfection with the restriction enzyme, PvuI, which cuts at a single site in the plasmid backbone. GS-CHOK1SV (clone 144E12) cells were transfected with linearized plasmid DNA via electroporation. Following transfection, cells were plated in 48-well plates (48WP) in order to generate stable pools. When pools were at least 50% confluent in the 48WPs, 100 µl of supernatant was analyzed for IgG expression using the ForteBio Octet and protein A biosensors (Pall ForteBio, Fremont, CA). The best expressing clones were scaled up into 6 well-plates (6 WP) and then into 125 mL shake flasks (SF). Once cells adapted to suspension culture in 125 mL flasks, 2 vials of each cell line pool were banked for LN storage. Since manufacturing cell lines must be clonal, the top 3 highest expressing pools were subcloned by limiting dilution in 96-well culture plates. To prove clonality and avoid a second round of limiting dilution, 96-well plates were imaged using Molecular Devices Clone-Select Imager (CSI) (Molecular Devices LLC, San Jose, CA) which captures images of single-cells and their subsequent growth. Clones were selected based on successful CSI images, growth and production in 96WPs.

To assess cell culture growth and productivity, the top expressing pools were further evaluated in a 14-day fed batch in 125 mL SFs. Cells were seeded in platform media and feeds consisting of Life Technologies' CD CHO plus 4 amino acids, proprietary feed CDF v6.2, and 10% glucose. Following the 14-day Fed-Batch, pools were centrifuged and the CD CHO produced mAb was isolated by filtering the supernatant via a 0.20 µm polyethersulfone (PES) membrane prior to purification.

A typical purification consists of two liters of conditioned medium (from CHO cell culture, 0.2 µm filtered) loaded onto a 235 mL column of MabSelect (GE healthcare, cat #17-5199-02). The column had been pre-equilibrated with PBS. The sample was loaded at a residence time of >2.5 minutes. Following load, the column was washed again with PBS, and then with 25 mM sodium acetate, pH ~neutral. The column was eluted with 25 mM acetic acid, pH 3.6, and then stripped with 250 mM acetic acid, 250 mM sodium chloride, pH ~2.2. Fractions (50 mL) were collected during the elution and strip steps. UV absorbance at A280 was monitored throughout. Peak fractions were pooled, pH adjusted to ~5.5 with the addition of 20 mM sodium acetate, and then dialyzed against three exchanges of buffer. The dialysate was collected, sterile filtered, and stored at 4° C.

Example 9

Neutralization of Canine NGF Biological Activity In Vitro

Figure 6:
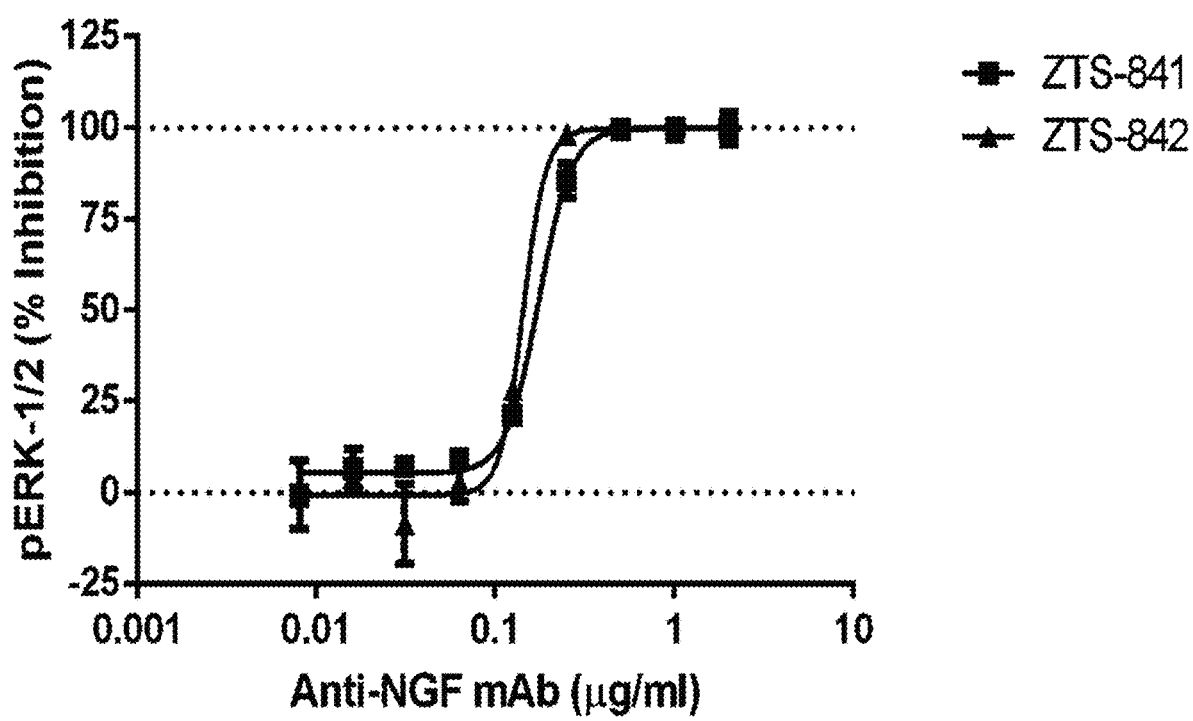
FIG. 6. is a representation of the effect of anti-NGF mAbs ZTS-841 and ZTS-842 on canine NGF induced pERK-1/2 signaling in caTrkA-CHO cells.
Figure 7:
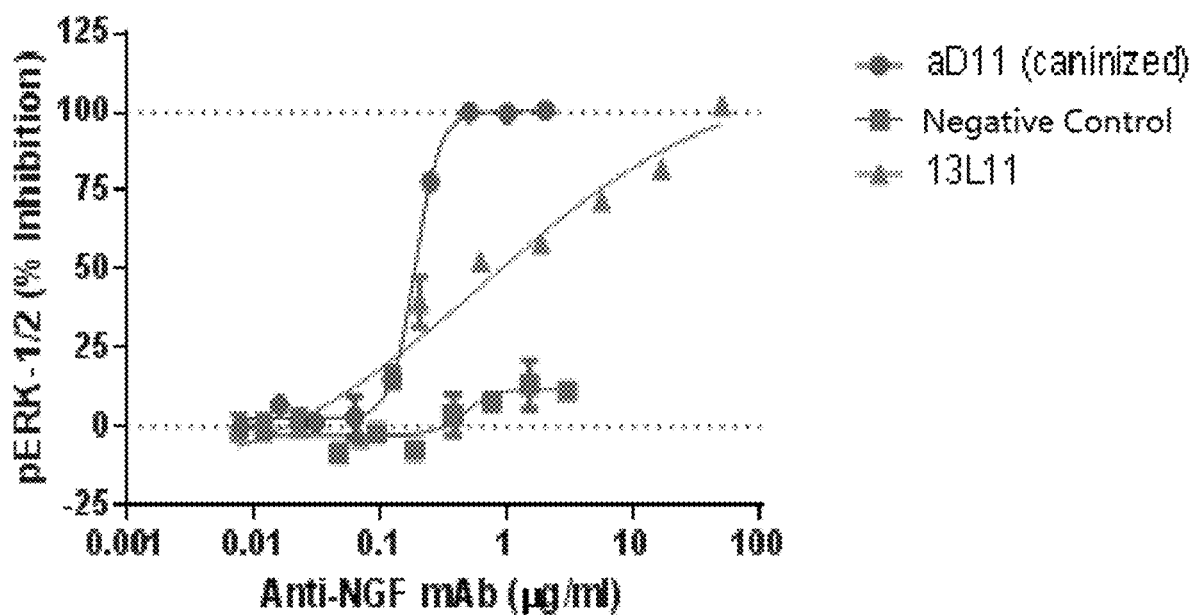
FIG. 7 is a representation of the caninized version of the aD11 mAb, a negative control and the 13L11 mAb on canine NGF induced pERK-1/2 signaling in caTrkA-CHO cells.

Affinities of each canine and felinized anti-NGF antibody to canine NGF were measured using SPR (Surface Plasmon Resonance) on a Biacore system (Biocore Life Sciences (GE Healthcare), Uppsala, Sweden) as described in Example 5. In addition, a functional in vitro assay was developed to measure inhibition constants for the mAbs ability to inhibit binding of NGF to TrkA. To determine if the anti-NGF mAbs of the invention blocked downstream cellular signaling as a result of inhibiting NGF binding to TrkA, purified antibodies were evaluated in an assay measuring canine NGF-induced phosphorylation of extracellular signal-regulated kinase 1 and 2 (pERK 1/2). Cells used in the assay were CHO-K1 expressing canine TrkA (Life Technologies) that were grown in DMEM/F12+GlutaMAX™-1 medium (Life technologies) supplemented with 10% dialyzed FBS, 20 mM HEPES, 500 µg/ml geneticin, and 1× antibiotic-antimycotic µg/ml (Life Technologies) at 37° C. in a humidified 5% CO2, 95% air incubator. For the pERK 1/2 assay, cells were seeded at $5.0 \times 10^4$ cells per well in 96-well tissue culture plates (Costar) and incubated overnight at 37° C. to allow for adherence. Cells were then serum-starved for 2 hours in HBSS containing calcium and magnesium chloride (Life Technologies). Anti-NGF antibodies were serially diluted in HBSS and pre-incubated with recombinant canine NGF diluted in HBSS/0.1% BSA at room temperature for 1 hour before adding to the cells. Final concentration of canine NGF and BSA in the assay was 15 ng/ml (EC90) and 0.025%, respectively. Cells were stimulated for 10 minutes at 37° C. before removing assay mixtures and adding 100 µl of cell lysis buffer provided with pERK 1/2 AlphaLISA® SureFire® Ultra assay kit (PerkinElmer). Cell lysates were than processed according manufacturer's instructions and plates read on an EnSpire® plate reader (PerkinElmer). Maximal response in the assay is defined as measured ERK 1/2 phosphorylation in the presence of canine NGF only (no mAb). Minimal response is defined as the basal levels of ERK 1/2 phosphorylation (no stimulation). Calculated inhibition values for anti-NGF antibodies are expressed as a percentage of minimal and maximal responses. Resulting percent inhibition data was plotted with GraphPad Prism 5 for IC50 determination (4-parameter curve fit). Please refer to FIG. 6-7

TF-1 Cellular Proliferation Assay

TF-1 cells (ATCC) were routinely grown in ATCC modified RPMI 1640 medium (Life Technologies) supplemented with 10% FBS and 2 ng/ml recombinant human GM-CSF (R & D Systems Inc.). TF-1 proliferation assay medium was RPMI 1640 supplemented with 10% BIT 9500 (Stemcell Technologies) and 10 µg/ml gentamicin. The TF-1 proliferation was performed in 96-well microplates (Costar) by incubating 15,000 cells per well with canine and felinized anti-NGF antibodies at concentrations indicated and 2 ng/ml recombinant canine NGF. After a 65-hour culture period, a CellTiter-GLO luminescent assay kit (Promega) was employed to evaluate the effects of anti-NGF antibodies on canine NGF induced cellular proliferation. Maximal response in the assay is defined proliferation in the presence of canine NGF only (no antibody). Minimal response is defined as measured proliferation without canine NGF.

Figure 8:
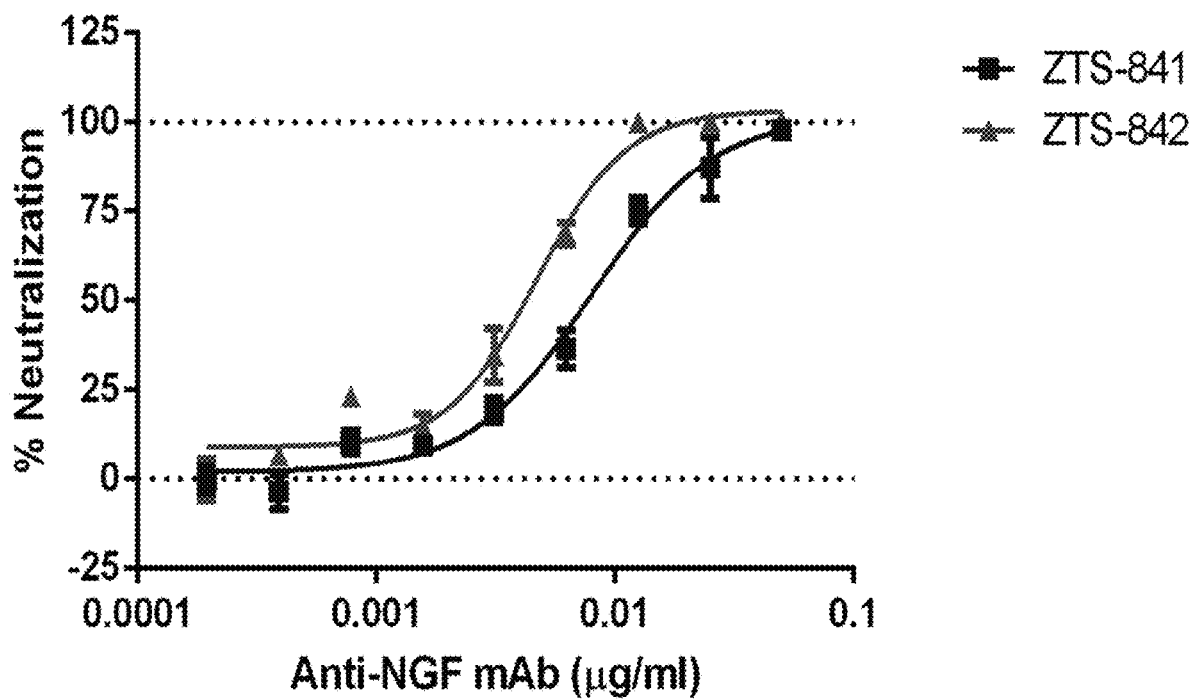
FIG. 8 is a representation of Anti-NGF mAbs on canine NGF induced TF-1 cell proliferation of ZTS-841 and ZTS-842 mAbs.
Figure 9:
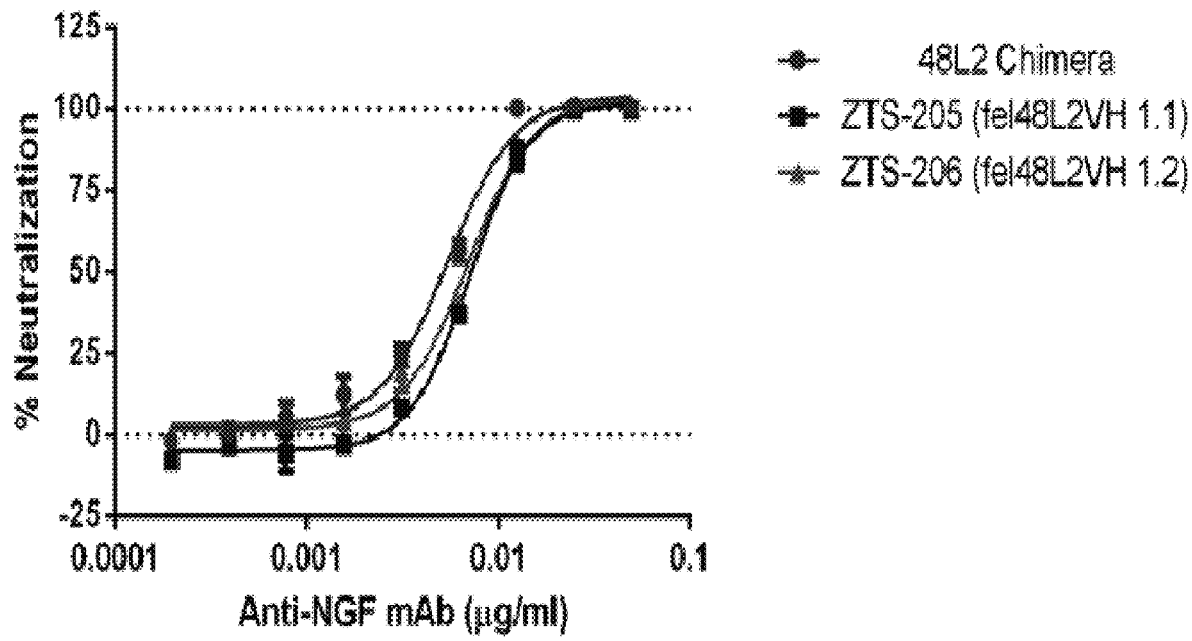
FIG. 9 is a representation of Anti-NGF mAbs on canine NGF induced TF-1 proliferation using the 48L2 chimera, the fel48L2VH1.1 and fel48L2VH1.2 mAbs.

Calculated inhibition (NGF neutralization) values for anti-NGF antibodies are expressed as a percentage of minimal and maximal responses. Resulting percent inhibition data was plotted with GraphPad Prism 5 for IC50 determination (4-parameter curve fit). Please refer to FIGS. 8-9.

Example 10

Pharmacokinetics

Figure 10:
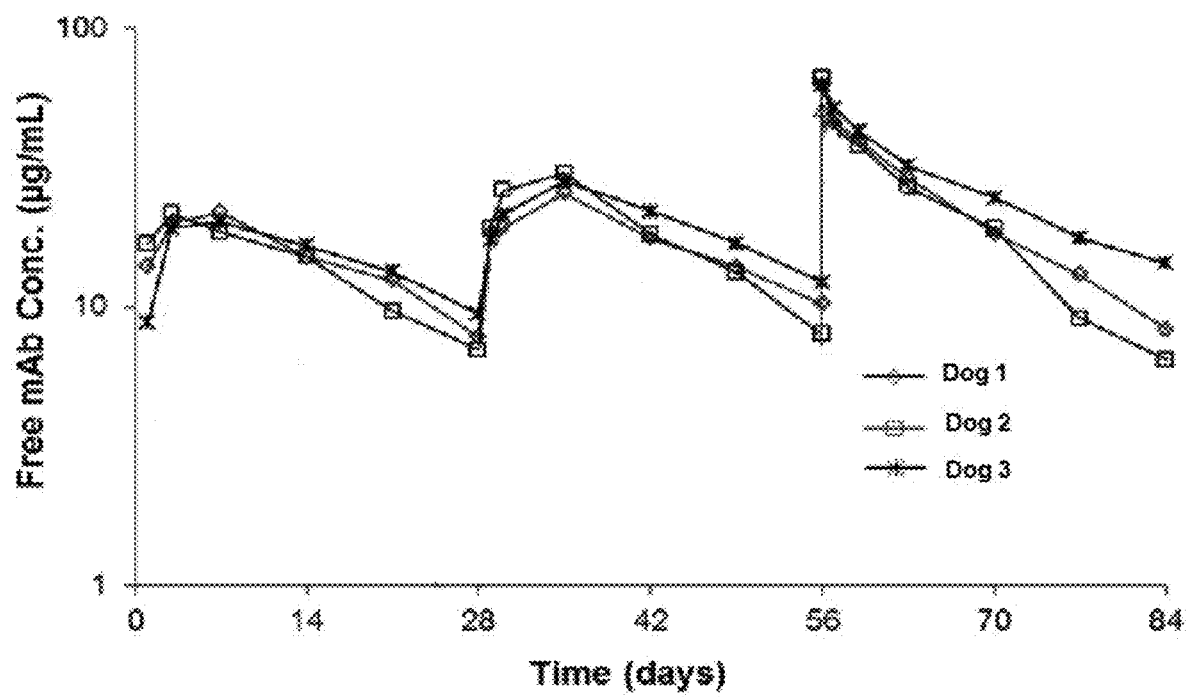
FIG. 10 is a representation of Anti-NGF mAb ZTS 841 dosed SC/SC/IV at 2.0 mg/kg for pharmacokinetic studies.
Figure 11:
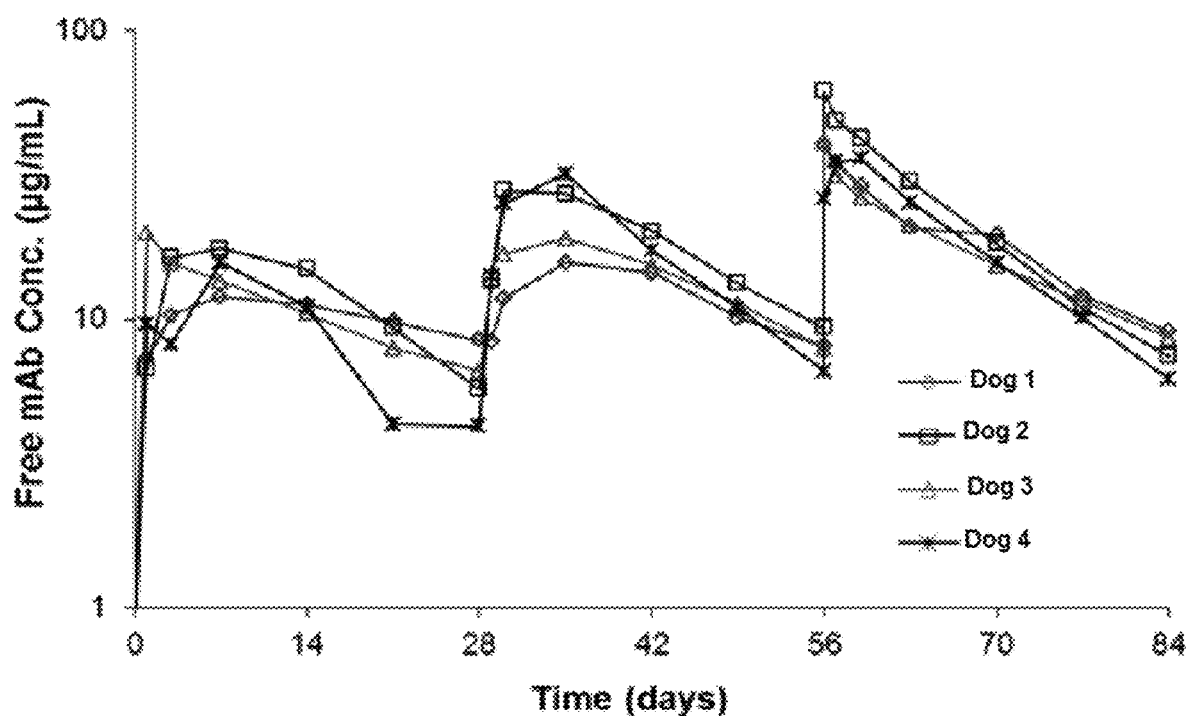
FIG. 11 is a representation of Anti-NGF mAb ZTS 842 dosed SC/SC/IV at 2.0 mg/kg for pharmacokinetic studies.

The pharmacokinetics (PK) of both canine anti-NGF mAb 48L2 (ZTS-842) and 9L12 (ZTS-841). Studies were undertaken in dogs following two subcutaneous (SC) and one intravenous (IV) dose of 2.0 mg/kg administered at 28 day intervals. The IV data demonstrated that the half-life was 13.3±3.4 days (mean±standard deviation) and the clearance was slow, 3.9±0.2 mL/day/kg. Following SC administration, peak serum concentrations were observed at 1-7 days after dosing. The SC absolute bioavailability averaged 88%±41%. In vivo binding to NGF was confirmed using a highly sensitive Total NGF (free+NGF-mAb complex) assay. Prior to dosing 48L2 (ZTS-842), NGF concentrations were less than the lower limit of quantitation, 10 μg/mL. After 48L2 (ZTS-842) administration, total NGF concentrations increased in all animals, averaging 1300±500 μg/mL on day 84 of the study. 48L2 (ZTS-842) concentrations were in large excess throughout the study, averaging 7.8±1.3 μg/mL on day 84, 28 days after the last dose, suggesting that even smaller doses would be adequate to capture endogenous NGF for at least one month after dosing. Although immunogenicity was not directly evaluated, there was no indication from the 48L2 (ZTS-842) concentration-time data that any anti-drug antibodies were induced in the four dogs during the three dose, 84-day study. Please refer to FIG. 11. Additionally, ZTS-841 was also studied using the same parameters as described above; dosed SC/SC/IV, 28 days apart at 20 mg/kg showing a half-life of 11.8+4.1 days. SC bioavailability of 94%+12%. Please refer to FIGS. 10-11.

The PK of felinized anti-NGF mAb fel48L21.1 (ZTS-205) were studied in 3 male and 3 female cats following two subcutaneous (SC) and one intravenous (IV) dose of 1.5 mg/kg administered at 28 day intervals. The IV data demonstrated that the half-life was 10.8±2.5 days (mean±standard deviation) and the clearance was slow, 3.0±1.0 mL/day/kg. Following SC administration, peak serum concentrations were observed at 2-7 days after dosing. The SC absolute bioavailability averaged 88%±17%. fel48L21.1 (ZTS-205) concentrations were in high throughout the study, averaging 7.2±4.0 μg/mL on day 84, 28 days after the last dose, suggesting that even smaller doses would be adequate to capture endogenous NGF for at least one month after dosing. Although immunogenicity was not directly evaluated, there was no indication from the ZTS-842 concentration-time data that any anti-drug antibodies were induced in the six cats during the three dose, 84-day study.

Bioanalytical Assay Methodology

A free 48L2 (ZTS-842) ligand binding assay was developed based on capture of free mAb by biotinylated canine NGF on a streptavidin Gyrolab™ disk and fluorescence detection after addition of AlexaFluor™-labeled murine anti-canine IgG monoclonal antibody. A free fel48L21.1 (ZTS-205) ligand binding assay was developed based on capture of free mAb by biotinylated canine NGF on a streptavidin Gyrolab™ disk and fluorescence detection after addition of AlexaFluor™-labeled goat anti-feline IgG polyclonal antibody.

Example 11

Evaluation of Canine and Felinized Anti-NGF Antibody in Rat MIA Model

Osteoarthritis (OA) is a degenerative joint disease characterized by joint pain and a progressive loss of articular cartilage. Intra-articular injection of MIA induces loss of articular cartilage with progression of subchondral bone lesions that mimic those of OA. This model offers a rapid and minimally invasive method to reproduce OA-like lesions in rodent species.

Figure 12:
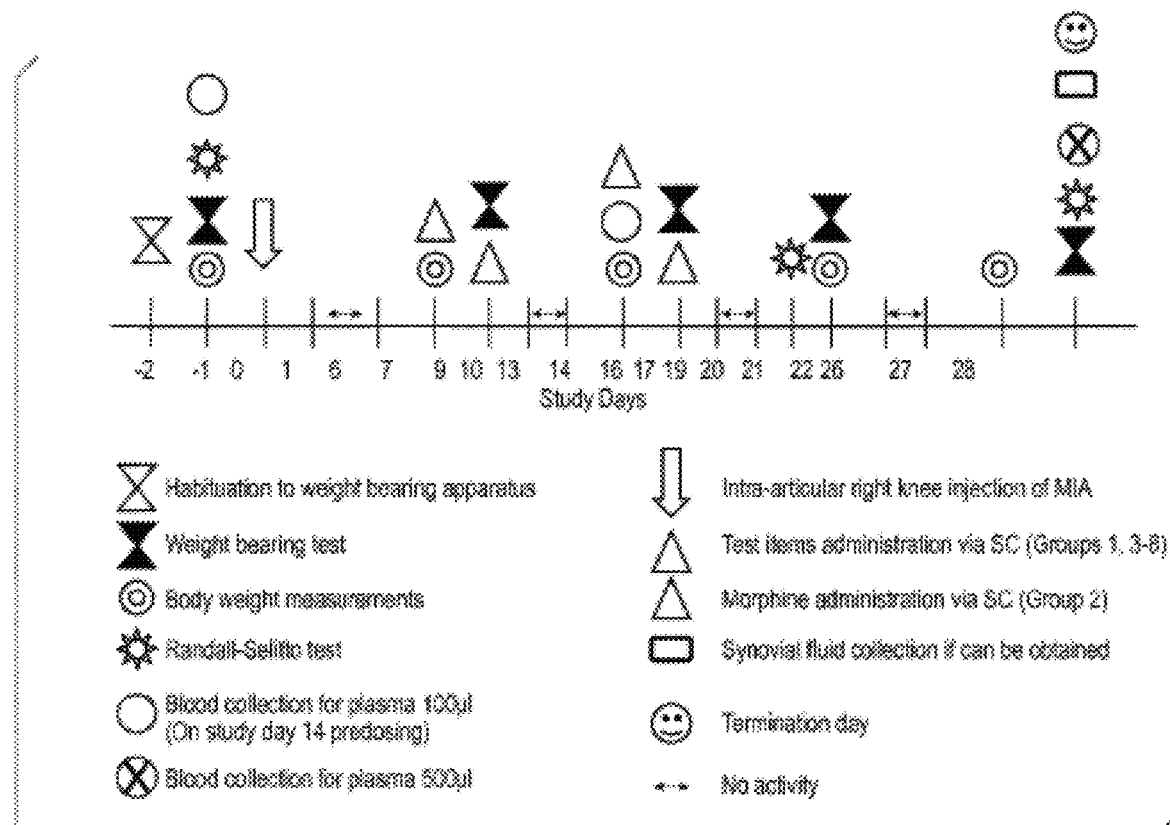
FIG. 12 is a schematic representation of the rat MIA assay.

The analgesic effect of speciated (example caninized, felinized and the like) anti-NGF antibodies at one dose of MIA in the rat MIA model of osteoarthritis were demonstrated by separately dosing monoclonal antibodies ZTS-841, ZTS-842 during the study on study day 7 and study day 14. Pain was assessed using weight bearing test for sustained pain and joint compression (Randall Selitto) test for mechanical hyperalgesiatest using an analgesimeter (Ugo Basile). The test was performed by applying a pressure to the hind paw. By pressing a pedal that activated a motor, the force increased at a constant rate on the linear scale. When pain was displayed withdrawal of the paw or vocalization is noted, the pedal was immediately released and the nociceptive threshold read on a scale. The cut-off of 400 g was used to avoid potential injury. Randall-Selitto test was performed on study days-1 (baseline), 20 and 28. See FIG. 12 for a schematic of the rat MIA procedure.

Loss of cartilage is induced via administration of the metabolic inhibitor, monoiodoacetate (MIA). Rats were anesthetized with isoflurane (3-5% in 100% 02). Once the animals were fully anesthetized, a 50 ul injection of 40 mg of MIA per milliliter of saline is injected into the intra-articular space of the left hind stifle using a 1 cc syringe fitted with a 27G needle. The animal was removed from the isoflurane and allowed to fully recover and then returned to their home cage.

To evaluate the effect of anti-NGF mAbs of the invention in these animals, the animals were assessed for weight bearing using an Incapacitance Tester. Animals were placed in the acrylic test chamber and when it is in the correct position an evaluation of force is taken. Three evaluations are taken at each time point. The percent weight bearing score (WBS) is calculated for each evaluation using the following formula:

$$\% \ WBS = \left[\frac{\text{weight on left leg}}{\text{weight on left leg} + \text{weight on right leg}}\right] * 100$$

The mean of the 3 WBS were taken as the WBS for that timepoint. On day-21, a WBS was calculated prior to MIA induction, MIA was instilled into the left stifle at a dose of 2 mg/0.05 mL. A WBS was measured on day-1 for randomization. On day 0, an anti-NGF mAb or placebo was administered and then weight bearing was assessed on days 7, 14, 21 and 28. Body weights were recorded weekly on the day of weight bearing assessment.

Figure 13:
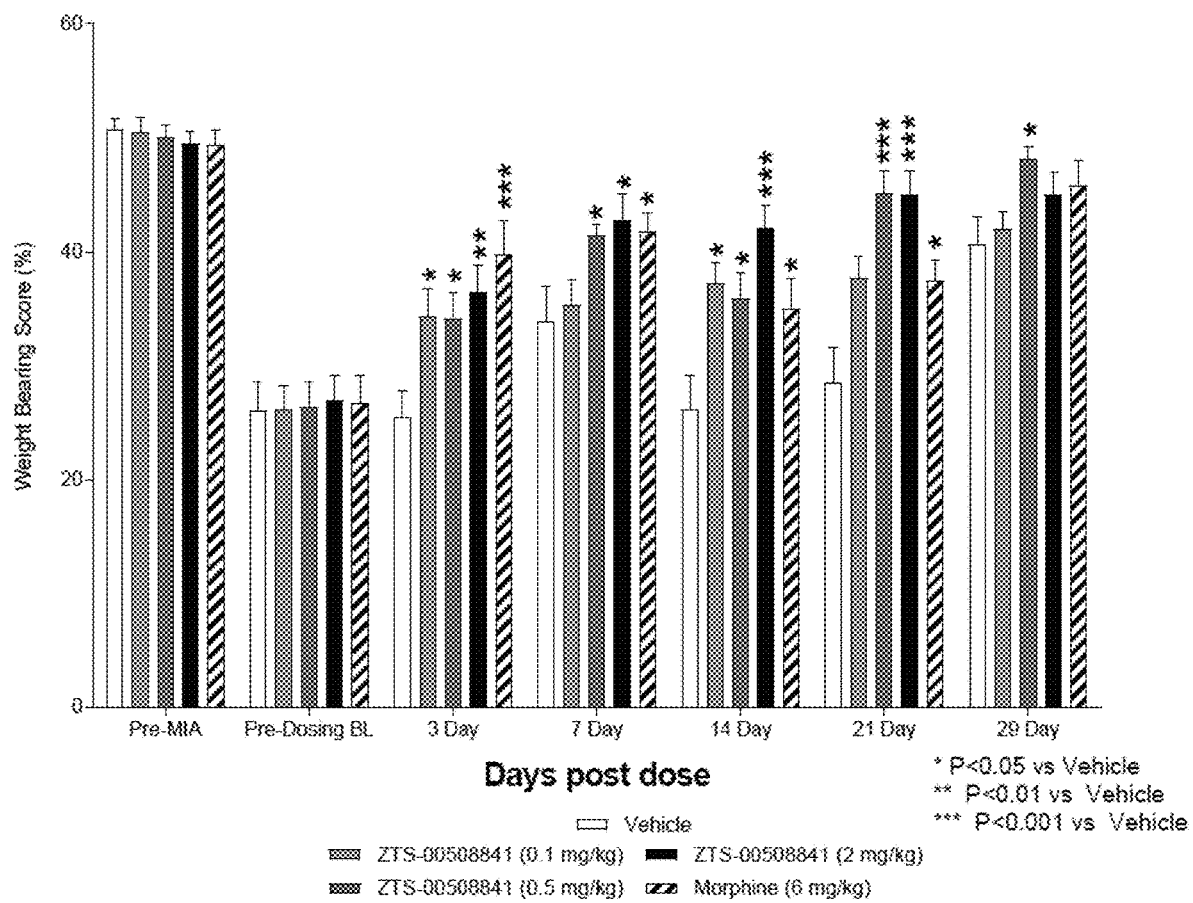
FIG. 13 is a graphical representation of mAb 841 at doses ranging from 0.1-2 mg/kg in the rat MIA assay.
Figure 14:
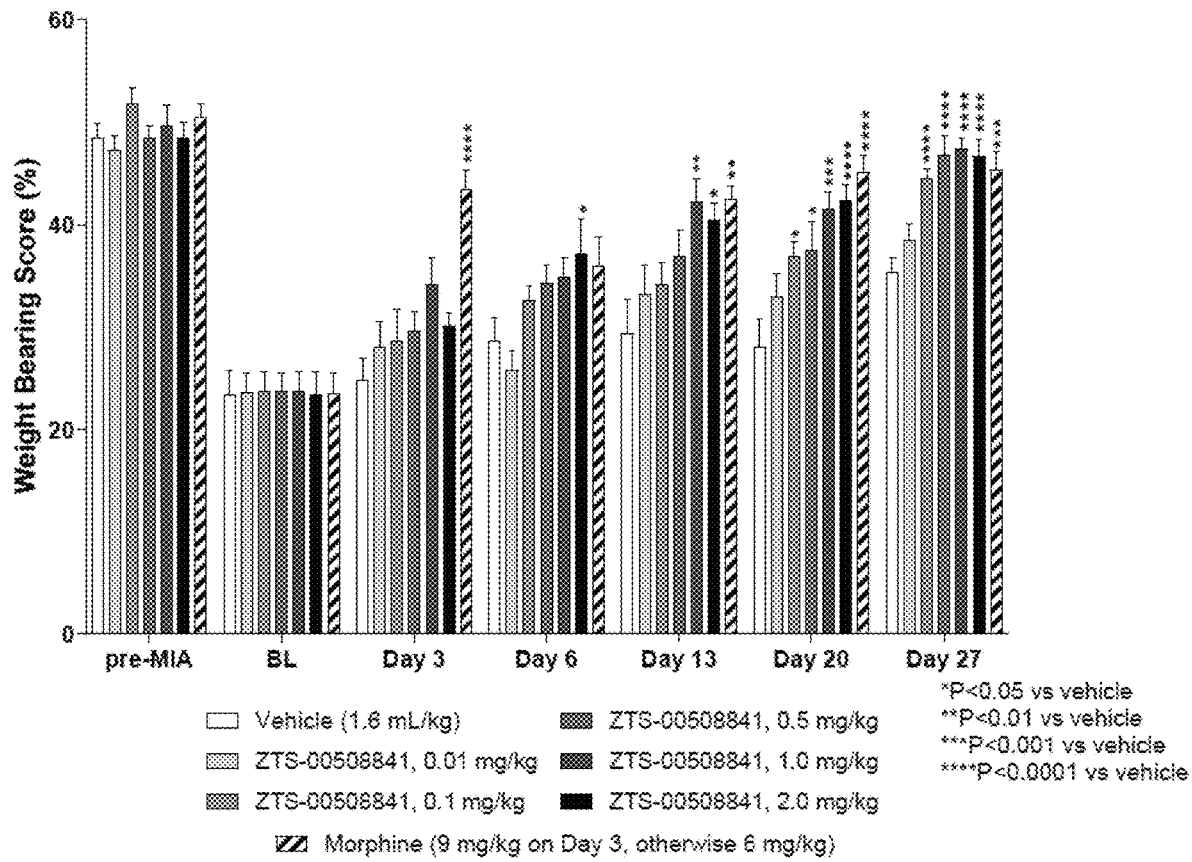
FIG. 14 is a graphical representation of mAb 841 at doses ranging from 0.01-2.0 mg/kg in the rat MIA assay.
Figure 15:
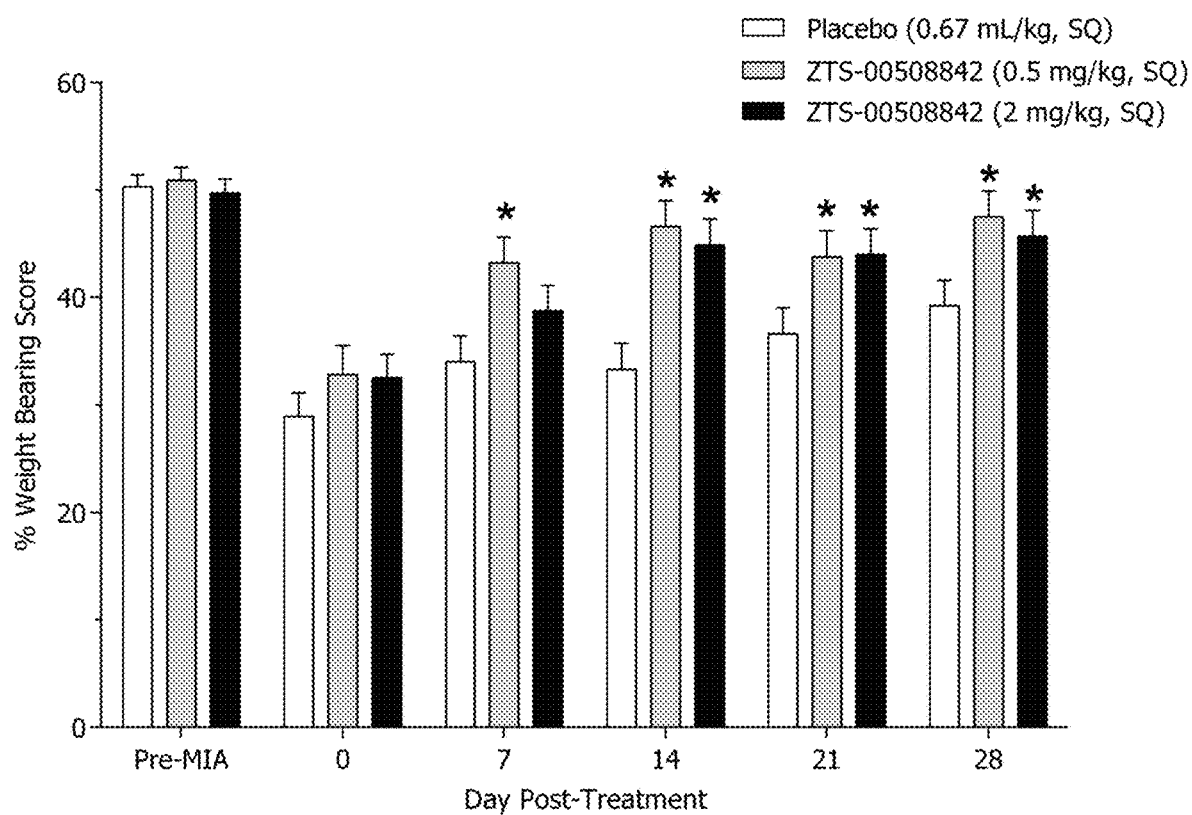
FIG. 15 is a graphical representation of mAb 842 at doses 0.5 and 2 mg/kg in the rat MIA assay.

Serum samples were collected on day 28 post dose administration via a terminal cardiac puncture. After euthanasia via CO2 asphyxiation, whole blood was collected from a cardiac puncture and placed into serum separator tubes, allowed to clot at room temperature, then centrifuged (3500 rpm, 15 min) and transferred into 96-well plates in two aliquots of 300 ul each as listed in the table below. Samples were frozen at ≤−10° C. until analyzed. Please refer to FIGS. 13-15 for a graphical representation of ZTS-841 and ZTS-842 as tested in the rat MIA assay.

Example 12

Effects on Lameness: Evaluation of Caninized Antibody in the Dog Synovitis Model Inflammatory processes in soft tissue are well recognized as one significant component of osteoarthritis. In the synovitis pain model, transient inflammation of the synovial membrane in a single stifle is induced via intra-articular injection of bacterial lipopolysaccharide (LPS). Quantifiable lameness occurs within 2 h of synovitis induction, peaks at 3-4 h, is waning by 6 h and is fully resolved after 24 h. This model has routinely been used to investigate targets for pain control.

A 5 mg/kg dose of ZTS-841 by intravenous injection administered once to intact male beagles reduced lameness, as compared to saline placebo, in a canine LPS synovitis model. As can be seen in Table 2 below, ZTS-841 demonstrated efficacy at 3 and hours post LPS synovitis induction.

Figure 16:
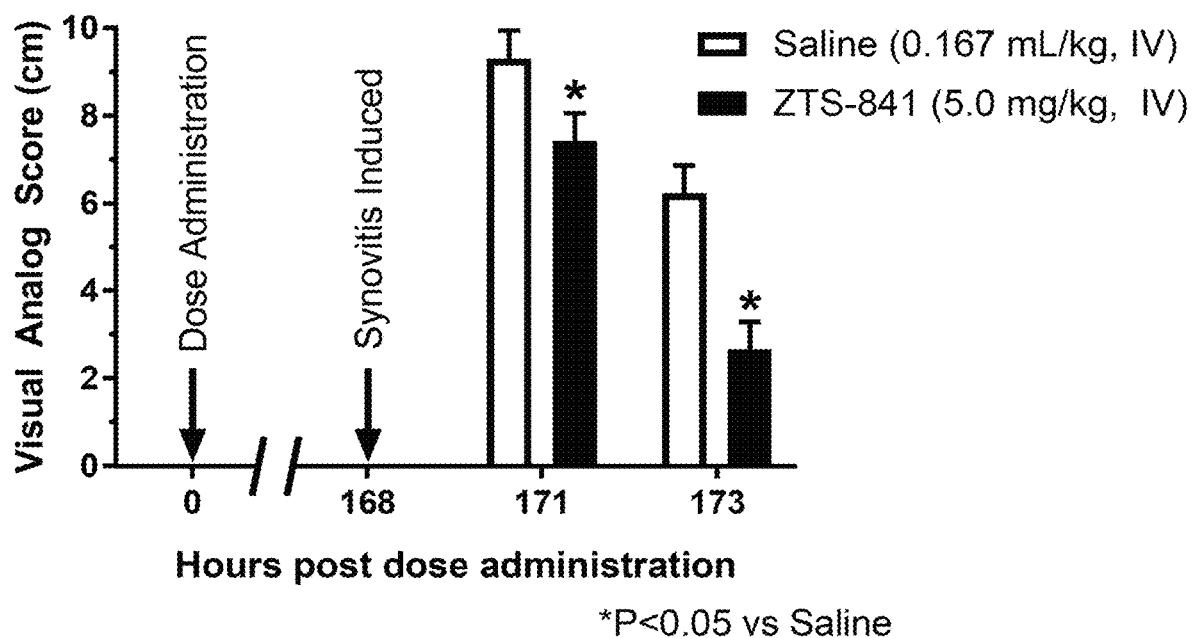
FIG. 16 is a graphical representation of mAb 841 lameness VAS for treatment groups at three, and five-hours post synovitis induction in the LPS synovitis model.

Table 2 and FIG. 16 represents least squares means (with standard error) for lameness VAS for treatment groups at three, and five-hours post synovitis induction. Differences between 5 mg/kg ZTS-841 and placebo were statistically significant.

TABLE 2

| Visual Analog Scores (cm) | | | |
|---|---|---|---|
| | | Hours post dose administration | |
| Treatment | Animal | 171 | 173 |
| Saline (0.167 mL/kg, IV) | 1 | 8.2 | 6.4 |
| | 2 | 9.8 | 4.1 |
| | 3 | 9.8 | 2.7 |
| | 4 | 6.2 | 1.0 |
| | 5 | 9.6 | 8.6 |
| | 6 | 9.4 | 8.3 |
| | 7 | 9.6 | 8.3 |
| | 8 | 9.4 | 4.6 |
| | 9 | 9.7 | 6.1 |
| | 10 | 9.7 | 4.5 |
| | 11 | 9.8 | 8.3 |
| | 12 | 9.8 | 9.7 |
| | 13 | 9.9 | 8.4 |
| ZTS-841 (5.0 mg/kg, IV) | 14 | 6.6 | 1.6 |
| | 15 | 8.8 | 4.9 |

TABLE 2-continued

| Visual Analog Scores (cm) | | | |
|---|---|---|---|
| | | Hours post dose administration | |
| Treatment | Animal | 171 | 173 |
| | 16 | 9.5 | 8.4 |
| | 17 | 9.7 | 0.7 |
| | 18 | 3.3 | 1.4 |
| | 19 | 8.6 | 4.5 |
| | 20 | 3.4 | 1.8 |
| | 21 | 2.7 | 1.4 |
| | 22 | 9.8 | 0.4 |
| | 23 | 9.8 | 4.1 |
| | 24 | 5.9 | 0.8 |
| | 25 | 9.6 | 0.4 |
| | 26 | 8.7 | 4.0 |

Example 13

Humanization of Antibody 48L2 (ZTS-842) and 9L12 (ZTS-841)

Similar to the felinization strategy described, and well known to one of skill in the art, appropriate germline antibody sequences were identified from all available human sequences for CDR grafting from mAb 48L2 and 9L12. Variable light chains and variable heavy chains were selected based on the highest homology to their respective canine frameworks. The CDRs of the native human segments were removed and replaced with parent canine CDRs. Recombinant humanized 48L2 and 9L12 were produced using the selected variable regions joined to their respective canine constant heavy IgG chain sequences. The antibodies were produced from HEK cells, purified as previously described, and then assessed for their ability to bind to human NGF, as shown in Table 3 below. Synthetic constructs representing the humanized variable heavy and light chains of mAb 48L2 (ZTS-842) and 9L12 (ZTS-841) were constructed. Different combinations of variable heavy and light chains within both sets were synthesized and assayed for binding (see below). CDR sequences were not changed during construction, only framework sequences were changed.

Antibody binding affinities of the antibodies against human NGF (SEQ ID NO. 66) were determined by surface plasmon resonance (SPR). Human NGF was immobilized on the surface of a BIACORE chip by direct amine coupling. Various concentrations of the described humanized anti-NGF antibodies were injected over the human NGF surfaces while the association of the antibody to the antigen and the dissociation of the formed complex were monitored in real time. Kinetic analysis was performed to obtain the equilibrium dissociation constant (KD). The results are shown in Table 3 below.

TABLE 3

| Humanized mAbs | | | | |
|---|---|---|---|---|
| Heavy chain variable region amino acid sequence | Light chain variable region amino acid sequence | ka (M − 1 s − 1) | kd (s − 1) | KD (M) |
| can9L12VH_HM855939 (SEQ ID NO. 69) | can9L12VL (SEQ ID NO. 7) | 3.90E+05 | 1.61E−03 | 4.12E−09 |
| can9L12VH_X92218 (SEQ ID NO. 67) | can9L12VL (SEQ ID NO. 7) | 3.01E+05 | 3.78E−05 | 1.26E−10 |
| can9L12VH (SEQ ID NO. 8) | can9L12VL_M94116_65698 (SEQ ID NO. 73) | 2.14E+05 | 1.97E−03 | 9.19E−09 |

TABLE 3-continued

| Humanized mAbs | | | | |
|---|---|---|---|---|
| Heavy chain variable region amino acid sequence | Light chain variable region amino acid sequence | ka (M − 1 s − 1) | kd (s − 1) | KD (M) |
| can48L2VH_HM855323.1 (SEQ ID NO. 79) | can48L2VL_Z22192.1 (SEQ ID NO. 91) | 1.67E+05 | 2.56E−04 | 1.54E−09 |
| can48L2VH_HM855323.1 (SEQ ID NO. 79) | can48L2VL_Z22192.1_P8A (SEQ ID NO. 87) | 2.05E+05 | 3.15E−04 | 1.54E−09 |
| can48L2VH_HM855323.1 (SEQ ID NO. 79) | can48L2VL_Z22192.1_P14L (SEQ ID NO. 89) | 1.44E+05 | 1.46E−07 | 1.02E−12 |
| can48L2VH_HM855336.1 (SEQ ID NO. 75) | can48L2VL_Z22192.1 (SEQ ID NO. 91) | 2.69E+05 | 3.37E−04 | 1.25E−09 |
| can48L2VH_HM855336.1 (SEQ ID NO. 75) | can48L2VL_Z22192.1_P8A (SEQ ID NO. 87) | 2.52E+05 | 2.12E−04 | 8.41E−10 |
| can48L2VH_HM855336.1 (SEQ ID NO. 75) | can48L2VL_Z22192.1_P14L (SEQ ID NO. 89) | 2.83E+05 | 4.22E−04 | 1.49E−09 |

Example 14

Paratope Scanning Mutagenesis of Antibody 48L2 9L12 (ZTS-841) and 48L2 (ZTS-842)

The region of an antibody responsible for antigen recognition represents the paratope. A paratope is created by a combination of amino acids in the complementarity determining regions (CDRs) of both the heavy and light chain variable regions. The binding between antibody and antigen is often mediated by side chains of CDR residues with side chains or carbohydrate moieties of the antigen. To help define critical side chains involved in antibody recognition alanine scanning mutagenesis was performed on each CDR residue in both the heavy and light chain, the technique as described by Cunningham and Wells (1989) Science, Vol. 244, Issue 4908, pp. 1081-1085. These mutants were then individually tested for the ability to NGF using the Biacore. The binding affinity to human NGF (hN below), canine NGF (cN below) and rat NGF (rN below) was measured and KD values were generated by the same protocols as described in Examples 5 and 9 above. Values were then compared to the wild type antibodies and are represented in the tables as a percent of wild type binding. The data presented in Tables 4 and 5 below are shown as a "percent similarity score" compared to wild type.

To determine the relative affinity of the alanine scanning mutant mAbs to the parent mAb binding profiles to NGF coated chips was determined at 100 nM using a Biacore T200. The mean response unit of four replicates of the parent mAb+/−3 standard deviations was used to generate parameters to define a threshold of response units comprising both the on- and off-rates antibody binding. The percentage of data points for each mutant fell within this threshold was then used to define a "% similarity score". The similarity score resulting from the substitution of alanine at each heavy and light chain CDR position of ZTS-841 and ZTS-842 for the heavy and light chain are shown as "percent inhibition relative to parent" in Tables 4 and 5 respectively. Results from substitution of alanine at each CDR position The sequences in Table 4 are directed towards alanine mutagenesis of the variable heavy and variable light chain CDR amino acid sequences of ZTS-841 (9L12). Table 5 is directed towards the alanine substitutions of the variable heavy and light chain CDR amino acid sequences of ZTS-842 (48L2) The amino acids mutated are described in the table according to the wild-type numbering of both the variable heavy and variable light chain sequences as previously described and included below. Amino acid positions 1, 25, 50, 75 and 100 are marked below. In the "sample name" column either the heavy or light variable sequence is listed with the numbered amino acid position alanine substitution.

ZTS-841 VH: SEQ ID NO. 8:

E$_1$VQLVESGGDLVKPGGSLRLSCVAS$_{25}$GFTFSSHGMHWVRQSPGKGL

QWVAV$_{50}$INSGGSSTYYTDAVKGRFTISRDNA$_{75}$KNTVYLQMNSLRAE

DTAMYYCAKES$_{100}$VGGWEQLVGPHFDYWGQGTLVIVSS$_{125}$

ZTS-841 VL: SEQ ID NO. 7:

Q$_1$SVLTQPTSVSGSLGQRVTISCSGS$_{25}$TNNIGILGASWYQLFPGKA

PKLLVY$_{50}$GNGNRPSGVPDRFSGADSGDSVTLT$_{75}$ITGLQAEDEADY

YCQSFDTTLGAHV$_{100}$FGGGTHLTVL$_{114}$

TABLE 4

| | Percent Similarity Score (%) | | |
|---|---|---|---|
| Sample name | KD on hN | KD on cN | KD on rN |
| can9L12VH_D113A | 99.99 | 100 | 99.98 |
| can9L12VH_E105A | 98.4 | 100 | 99.99 |
| can9L12VH_E99A | 81.97 | 97.72 | 80.5 |
| can9L12VH_F112A | 8 | 28.28 | 11.8 |
| can9L12VH_F27A | 100 | 100 | 99.97 |
| can9L12VH_F29A | 100 | 100 | 99.94 |
| can9L12VH_G102A | 3.4 | 11.04 | 4.7 |
| can9L12VH_G103A | 38.2 | 99.81 | 62.48 |
| can9L12VH_G109A | 40.05 | 99.96 | 62.02 |
| can9L12VH_G26A | 97.44 | 99.97 | 94.8 |
| can9L12VH_G33A | 99.99 | 100 | 99.91 |
| can9L12VH_G54A | 96.2 | 100 | 93.78 |
| can9L12VH_G55A | 99.97 | 100 | 99.34 |
| can9L12VH_H111A | 2.79 | 10.1 | 3.25 |
| can9L12VH_H32A | 13.81 | 38.24 | 51.46 |
| can9L12VH_I50A | 96.56 | 99.95 | 92.04 |
| can9L12VH_K98A | 8.58 | 22.75 | 7.92 |
| can9L12VH_L107A | 1.82 | 5.45 | 2 |
| can9L12VH_N52A | 38.2 | 85.83 | 19.7 |
| can9L12VH_P110A | 2.1 | 6.48 | 2.6 |
| can9L12VH_Q106A | 100 | 100 | 99.94 |
| can9L12VH_S100A | 42.09 | 76.22 | 51.57 |

TABLE 4-continued

| Sample name | KD on hN | KD on cN | KD on rN |
|---|---|---|---|
| can9L12VH_S30A | 31.19 | 94.71 | 99.93 |
| can9L12VH_S31A | 99.88 | 99.99 | 99.98 |
| can9L12VH_S53A | 100 | 100 | 99.94 |
| can9L12VH_S56A | 40.45 | 96.76 | 96 |
| can9L12VH_S57A | 33.41 | 89.87 | 99.95 |
| can9L12VH_T28A | 96.58 | 99.96 | 99.96 |
| can9L12VH_T58A | 100 | 99.98 | 99.93 |
| can9L12VH_V101A | 5.29 | 13.61 | 4.27 |
| can9L12VH_V108A | 56.34 | 93.15 | 61.98 |
| can9L12VH_W104A | 5.2 | 19.21 | 8.2 |
| can9L12VH_Y114A | 99.86 | 100 | 99.19 |
| can9L12VL_D93A | 3.3 | 11 | 3.7 |
| can9L12VL_F92A | 2.7 | 7.2 | 2.3 |
| can9L12VL_G30A | 16.2 | 53.9 | 13.8 |
| can9L12VL_G33A | 2.3 | 7.5 | 2.9 |
| can9L12VL_G51A | 100 | 100 | 99.94 |
| can9L12VL_G53A | 10 | 34.2 | 11.7 |
| can9L12VL_G97A | 43.32 | 98.9 | 35.93 |
| can9L12VL_H99A | 56.91 | 99.99 | 43.73 |
| can9L12VL_I29A | 1.5 | 4.4 | 1.6 |
| can9L12VL_I31A | 11.4 | 41.21 | 12.6 |
| can9L12VL_L32A | 1.5 | 4.4 | 1.7 |
| can9L12VL_L96A | 34.25 | 96.97 | 37 |
| can9L12VL_N27A | 100 | 100 | 99.94 |
| can9L12VL_N28A | 2.1 | 6.6 | 2.5 |
| can9L12VL_N52A | 100 | 100 | 99.95 |
| can9L12VL_Q90A | 19.34 | 79.24 | 24.2 |
| can9L12VL_S91A | 11.6 | 39.3 | 14.5 |
| can9L12VL_T26A | 99.99 | 100 | 99.17 |
| can9L12VL_T94A | 52.48 | 99.99 | 40.02 |
| can9L12VL_T95A | 100 | 99.95 | 99.93 |
| can9L12VL_V100A | 15.7 | 58.2 | 20.2 |

For Table 5:

ZTS-842 VH: SEQ ID NO. 28
EVQLVESGGDLVKPGGSLRLSCVASGFTFSTYGINWVRQAPGKGL

QWVAYISSGGSSTYYADPVKGRFTISRDDAKNMLYLQMNSLRAE

DTAIYYCAGSRYTYAYGGGYEFHFWGQGTLVTVSS

ZTS-842 VL: SEQ ID NO. 27
QAVLNQPASVSGALGQKVTISCSGSTMDIDIFGVSWYQQLPGKAPK

LLVDSDGDRPSGIPDRFSGSRSGNSGTLTITGLQAEDEADYHCQS

GDSTLGALAIFGGGTHVTVL

TABLE 5

| Sample name | KD on hN | KD on cN | KD on rN |
|---|---|---|---|
| can48L2VL_T26A | 99.8 | 97.31 | 98.02 |
| can48L2VL_M27A | 72.11 | 28 | 37.9 |
| can48L2VL_D28A | 99.63 | 96.95 | 97.7 |
| can48L2VL_I29A | 97.83 | 47 | 57.2 |
| can48L2VL_D30A | 99.69 | 98.28 | 98.67 |
| can48L2VL_I31A | 86.16 | 32.9 | 39.9 |
| can48L2VL_F32A | 44.32 | 19.6 | 66.01 |
| can48L2VL_G33A | 56.61 | 17.5 | 21.2 |
| can48L2VL_S51A | 100 | 100 | 100 |
| can48L2VL_D52A | 100 | 99.7 | 99.9 |
| can48L2VL_G53A | 100 | 99.98 | 99.99 |
| can48L2VL_Q90A | 99.88 | 94.42 | 98.67 |
| can48L2VL_S91A | 97.52 | 59.6 | 76.68 |
| can48L2VL_G92A | 99.27 | 93.63 | 97.05 |
| can48L2VL_D93A | 99.93 | 98.68 | 99.51 |
| can48L2VL_S94A | 99.96 | 97.79 | 99.32 |
| can48L2VL_T95A | 99.6 | 94.87 | 99.44 |
| can48L2VL_L96A | 99.88 | 89.98 | 93.23 |
| can48L2VL_G97A | 99.97 | 92.43 | 99.59 |
| can48L2VL_A98L | 99.82 | 97.34 | 98.43 |
| can48L2VL_L99A | 99.8 | 96.85 | 98.39 |
| can48L2VL_A100L | 99.88 | 97.79 | 98.26 |
| can48L2VL_I101A | 99.99 | 97.27 | 99.6 |
| can48L2VH_T31A | 99.9 | 99.58 | 99.86 |
| can48L2VH_I51A | 81.81 | 24.2 | 37.2 |
| can48L2VH_S52A | 100 | 99.37 | 99.75 |
| can48L2VH_S53A | 99.96 | 97.84 | 99.4 |
| can48L2VH_G54A | 99.95 | 98.11 | 99.3 |
| can48L2VH_G55A | 99.97 | 99.26 | 99.71 |
| can48L2VH_S56A | 99.94 | 99.31 | 99.8 |
| can48L2VH_S57A | 99.98 | 98.37 | 99.72 |
| can48L2VH_T58A | 99.91 | 99.13 | 99.66 |
| can48L2VH_H112A | 51.2 | 40.31 | 98.46 |
| can48L2VH_F113A | 98.52 | 33.7 | 32.2 |
| can48L2VL_T26A | 99.8 | 97.31 | 98.02 |
| can48L2VL_M27A | 72.11 | 28 | 37.9 |
| can48L2VL_D28A | 99.63 | 96.95 | 97.7 |
| can48L2VL_I29A | 97.83 | 47 | 57.2 |
| can48L2VL_D30A | 99.69 | 98.28 | 98.67 |
| can48L2VL_I31A | 86.16 | 32.9 | 39.9 |
| can48L2VL_F32A | 44.32 | 19.6 | 66.01 |
| can48L2VL_G33A | 56.61 | 17.5 | 21.2 |
| can48L2VL_S51A | 100 | 100 | 100 |
| can48L2VL_D52A | 100 | 99.7 | 99.9 |
| can48L2VL_G53A | 100 | 99.98 | 99.99 |
| can48L2VL_Q90A | 99.88 | 94.42 | 98.67 |
| can48L2VL_S91A | 97.52 | 59.6 | 76.68 |
| can48L2VL_G92A | 99.27 | 93.63 | 97.05 |
| can48L2VL_D93A | 99.93 | 98.68 | 99.51 |
| can48L2VL_S94A | 99.96 | 97.79 | 99.32 |
| can48L2VL_T95A | 99.6 | 94.87 | 99.44 |
| can48L2VL_L96A | 99.88 | 89.98 | 93.23 |
| can48L2VL_G97A | 99.97 | 92.43 | 99.59 |
| can48L2VL_A98L | 99.82 | 97.34 | 98.43 |
| can48L2VL_L99A | 99.8 | 96.85 | 98.39 |

Values generated in Tables 4 and 5 having a percent similarity less than 50% suggest amino acid positions essential to the binding of the antibody paratope to NGF. The mutation of the wild type amino acid at the noted position with an alanine leading to a reduced, or overall lack of binding to, NGF suggests which amino acids are required for binding and which amino acids might be substituted with, at a minimum, conservative amino acid substitutions.

What is claimed is:

1. An isolated nucleic acid molecule encoding a canine antibody or antigen-binding fragment thereof that specifically binds to nerve growth factor (NGF), wherein the antibody or antigen-binding fragment comprises a light chain variable region encoded by a nucleic acid molecule comprising SEQ ID NO. 37 and a heavy chain variable region encoded by a nucleic acid molecule comprising SEQ ID NO. 38.

2. An isolated nucleic acid molecule encoding a canine anti-NGF antibody or antigen-binding fragment thereof that specifically binds to NGF which comprises three light chain variable region Complementarity Determining Regions (CDRs) contained within the light chain variable region encoded by nucleic acid molecule comprising SEQ ID NOs: 31-33 and three heavy chain variable region Complementarity Determining Regions (CDRs) contained within the heavy chain variable region encoded by nucleic acid molecule comprising SEQ ID NOs: 34-36.

3. An expression vector comprising the nucleic acid molecule of claim 1 or claim 2.

4. A host cell comprising the vector according to claim 3.

5. A method of producing a canine anti-NGF antibody or antigen-binding fragment comprising introducing the expression vector of claim 3 into an isolated host cell, growing the cell under conditions permitting production of the antibody or antibody fragment, and recovering the antibody or antibody fragment so produced.

* * * * *